US006248787B1

(12) United States Patent
Bianchi et al.

(10) Patent No.: US 6,248,787 B1
(45) Date of Patent: Jun. 19, 2001

(54) GUANYLHYDRAZONES AND THEIR USE TO TREAT INFLAMMATORY CONDITIONS

(75) Inventors: Marina Bianchi, Milan (IT); Anthony Cerami, Shelter Island, NY (US); Kevin J. Tracey, Old Greenwich, CT (US); Peter Ulrich, Old Tappan, NJ (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 08/479,050

(22) Filed: Jun. 6, 1995

Related U.S. Application Data

(60) Division of application No. 08/463,568, filed on Jun. 5, 1995, which is a continuation-in-part of application No. 08/315,170, filed on Sep. 29, 1994, now Pat. No. 5,599,984, which is a continuation-in-part of application No. 08/184,540, filed on Jan. 21, 1994, now abandoned.

(51) Int. Cl.$^7$ .......................... A61K 31/16; A61K 31/17; A61K 31/155
(52) U.S. Cl. ........................ 514/615; 514/596; 514/597; 514/614; 514/616; 514/632; 514/634; 514/636
(58) Field of Search ................................... 514/357, 596, 514/597, 616, 632, 634, 636, 674, 615, 614

(56) References Cited

U.S. PATENT DOCUMENTS

| 3,143,461 | 8/1964 | Berg ..................................... 514/597 |
| 3,560,557 | * 2/1971 | Marxer et al. ......................... 562/114 |
| 3,799,988 | 3/1974 | Hashimoto et al. .................. 564/157 |
| 5,380,945 | 1/1995 | Murad et al. ......................... 564/108 |

FOREIGN PATENT DOCUMENTS

| 2884404 | 5/1979 | (DE) . |
| 222266 | 7/1968 | (SU) . |

OTHER PUBLICATIONS

Berger et al., 1991, "Hydroxylation of Pentamidine by Rat Liver Microsomes" *The Journal of Pharmacology and Experimental Therapeutics 256*: 883–889.
Beutler and Cerami, 1988, "The Common Mediator of Shock, Cachexia and Tumor Necrosis", *Advances in Immunology 42*: 213–231.
Billiar et al., 1990, "Modulation of Nitrogen Oxide Synthesis In Vivo: $N^G$–Monomethyl–L–Arginine Inhibits Endotoxin–Induced Nitrite/Nitrate Biosynthesis While Promoting Hepatic Damage", *Journal of Leukocyte Biology 48*: 565–569.
Bouskela and Rubanyi, 1994 "Effects of $N_\gamma$–Nitro–L–Arginine and Dexamethasone on Early Events Following Lipopolysaccharide Injection : Observations in the Hamster Cheek Pouch Microcirculation" *Shock 1*: 347–353.

Brennan, M. F., 1981, "Total Parenteral Nutrition in the Cancer Patient", *The New England Journal of Medicine 305*: 375–382.
Cobb et al., 1992, "$N^\omega$Amino–L–Arginine, an Inhibitor of Nitric Oxide Synthase, Raises Vascular Resistance but Increases Mortality Rates in Awake Canines Challenged with Endotoxin", *J. Exp. Med. 176*: 1175–1182.
Darling et al., 1990, "Cachectic Effects of Recombinant Human Tumor Necrosis Factor in Rats", *Cancer Research 50*: 4008–4013.
Denny et al., 1979, "Potential Antitumor Agents. 31. Quantitative Structure–Activity Relationships for the Antileukemic Bis(guanylhydrazones)", *Journal of Medicianl Chemistry 22*:1234–1238.
Detsky et al., 1987, "Perioperative Parenteral Nutrition: A Meta–Analysis",*Annals of Internal Medicine 107*: 195–203.
Ding et al., 1988, "Release of Reactive Nitrogen Intermediates and Reactive Oxygen Intermediates from Mouse Peritoneal Macrophages", *The Journal of Immunology 141*: 2407–2412.
Granger et al., 1990, "Metabolic Fate of L–Arginine in Relation to Microbiostatic Capability of Murine Macrophages", *J. Clin. Invest. 85*: 264–273.
Hibbs et al., 1987, "Macrophage Cytotoxicity: Role for L–Arginine Deiminase and Imino Nitrogen Oxidation to Nitrite", *Science 235*:: 473–476.
Kemp and Petrakis, 1981, "Synthesis and Conformational Analysis of cis,cis–1,3,5–Trimethylcyclohexane–1,3,5–tricarboxylic Acid", *J. Org. Chem. 46*: 5140–5143.
Kilbourn et al., 1980, "Reversal of Endotoxin–Mediated Shock by $N^G$–Methyl–L–Arginine, An Inhibitor of Nitric Oxide Synthesis", *Biochemical and Biophysical Research Communications 172*: 1132–1138.
Koretz, R. L., 1984, "Parenteral Nutrition, Is it Oncologically Logical?" *Jornal of Clincial Oncology 2*: 534–538.
Korytnyk et al., 1978, "Guanylhydrazones with Potential Antileukemic Activity. 2. Synthesis and Structure–Activity Relationships of Analogues of 4,4'–Diacetyl–N, N'–diphenylurea Bis(guanylhydrazone)$^{1,2}$", *Journal of Medicinal Chemistry 21*: 507–513.

(List continued on next page.)

Primary Examiner—Shailendra Kumar
(74) Attorney, Agent, or Firm—Jeffrey B. Oster

(57) ABSTRACT

This invention concerns new methods and compositions that are useful in preventing and ameliorating cachexia, the clinical syndrome of poor nutritional status and bodily wasting associated with cancer and other chronic diseases. More particularly, the invention relates to aromatic guanylhydrazone (more properly termed amidinohydrazone) compositions and their use to inhibit the uptake of arginine by macrophages and/or its conversion to urea. These compositions and methods are also useful in preventing the generation of nitric oxide (NO) by cells, and so to prevent NO-mediated inflammation and other responses in persons in need of same. In another embodiment, the compounds can be used to inhibit arginine uptake in arginine-dependent tumors and infections.

3 Claims, 23 Drawing Sheets

OTHER PUBLICATIONS

Kubes et al., 1992, "Participation in $\alpha_2$–adrenergic receptors in neural vascular tone of canine skeletal muscle", *The American Journal of Physiology 262*: H611–H615.

Langstein et al., 1989, "Reversal of Cancer Cachexia by Antibodies to Interferon–Gamma but not Cachectin/Tumor Necrosis Factor", *Surgical Forum 15*: 408–410.

McGeer et al., 1989, "Parenteral Nutrition in Patients Receiving Cancer Chemotherapy", *Annals of Internal Medicine 110*: 734–736.

Mihich et al., 1968, "Effects of 4,4'–Diacetyl–diphenyl–urea–bis(guanylhydrazone) on Leukemia L1210", *Cancer Research 28*: 354–362.

Minnard et al., 1994, "Inhibition of Nitric Oxide Synthesis is Detrimental During Endotoxemia", *Arch. Surg. 129*: 142–148.

Nathan, Carl, 1992, "Nitric oxide as a secretory product of mammalian cells", *The FASEB Journal 6*: 3051–3064.

Sherry et al., 1989, "Anticachectin/tumor necrosis factor–$\alpha$ antibodies attenuate development of cachexia in tumor models", *The FASEB Journal 3*: 1956–1962.

Ulrich and Cerami, 1984, "Trypanocidal 1,3–Arylene Diketone Bis(Guanylhydrazones). Structure–Activity Relationships among Substituted and Heterocyclic Analogues" *Journal of Medicinal Chemistry 27*: 35–40.

Ulrich et al., 1982, "The Trypanocidal Activity of Various Aromatic Bisguanylhydrazones In Vivo", *Drug Development Research 2*: 219–228.

Moncada and Higgs, 1993, "The L–Arginine–Nitric Oxide Pathway", *New England Journal of Medicine 329*: 2002–2012.

Van Dervort et al., 1994, "Nitric Oxide Regulates Endotoxin–Induced TNF–$\alpha$ Production by Human Neutrophils", *Journal of Immunology 141*: 2407–2412.

\* cited by examiner

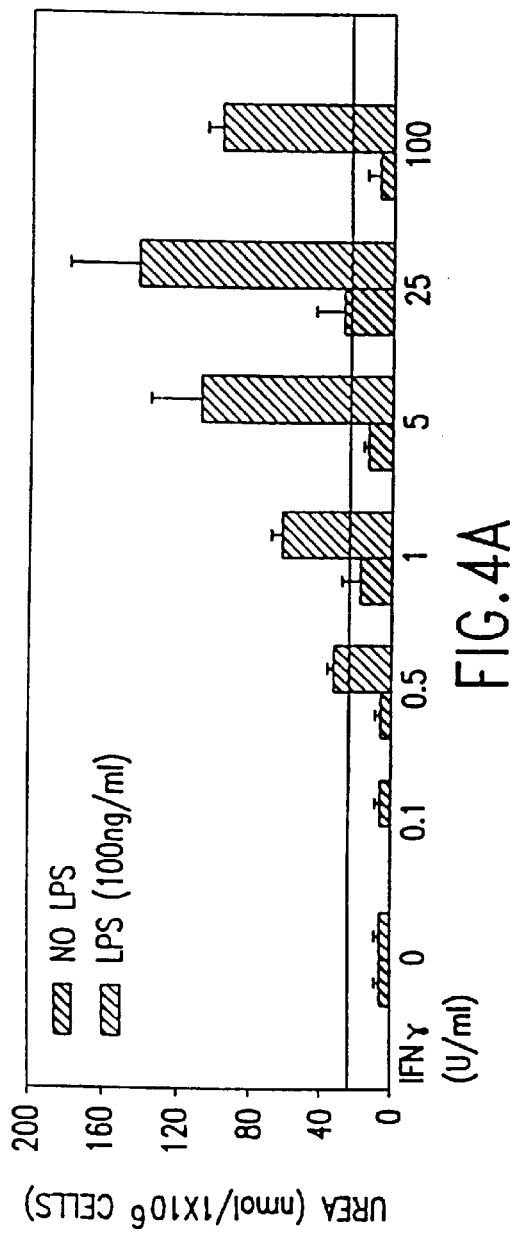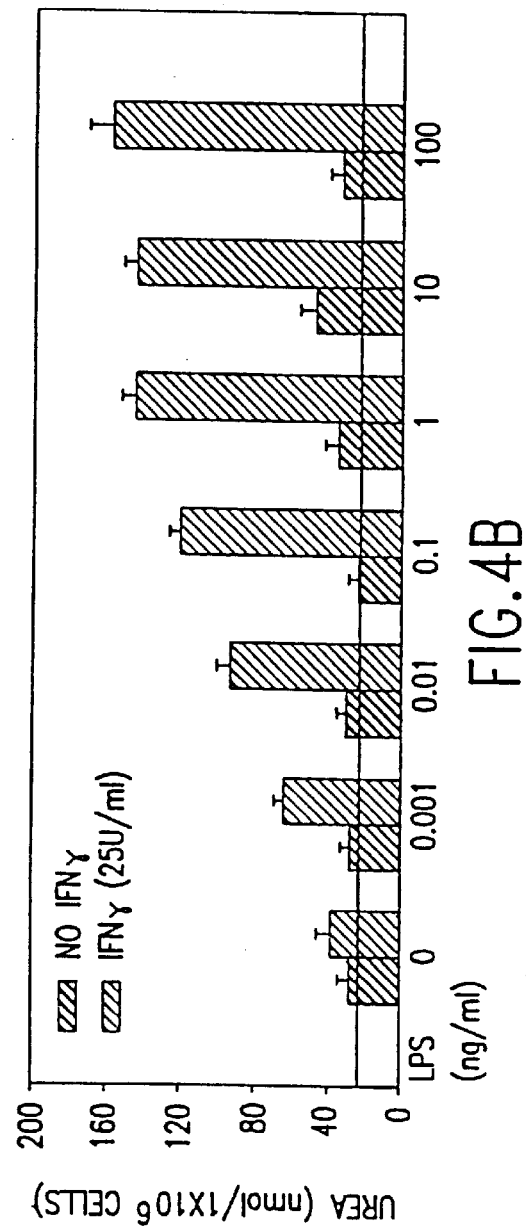

Figure 7D:
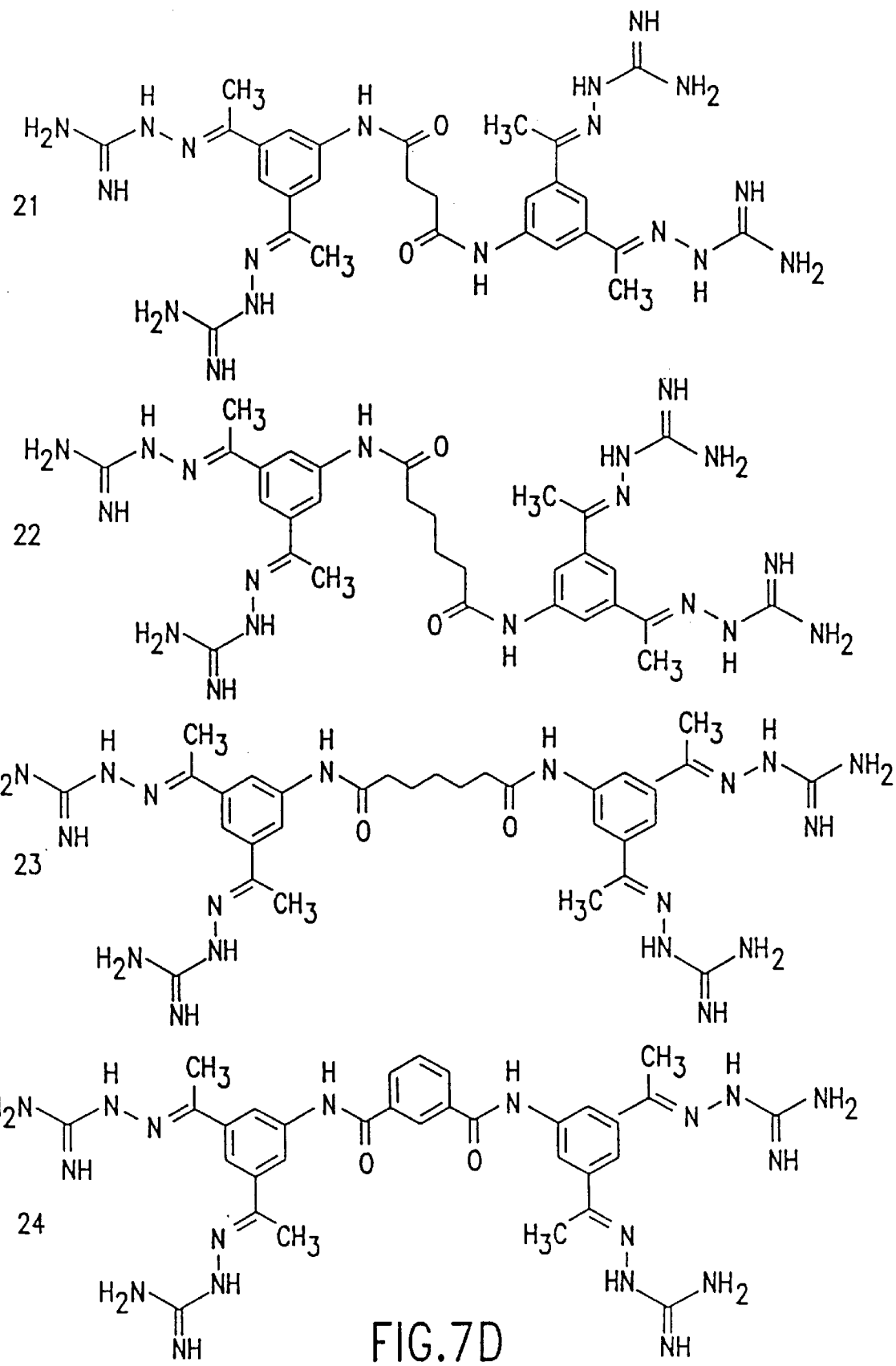
Figure 8:
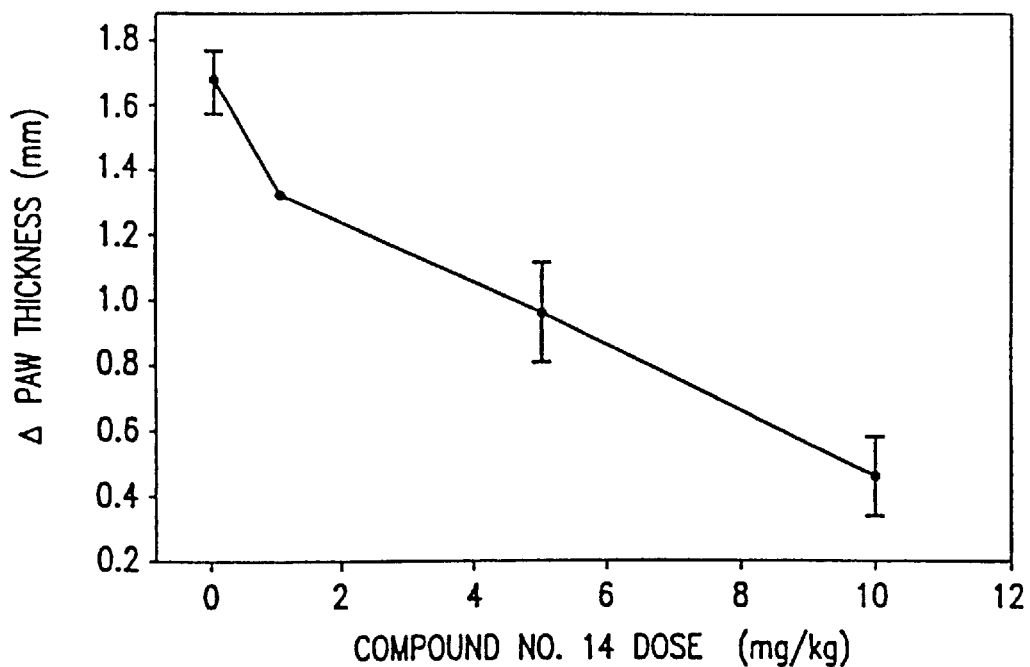

1 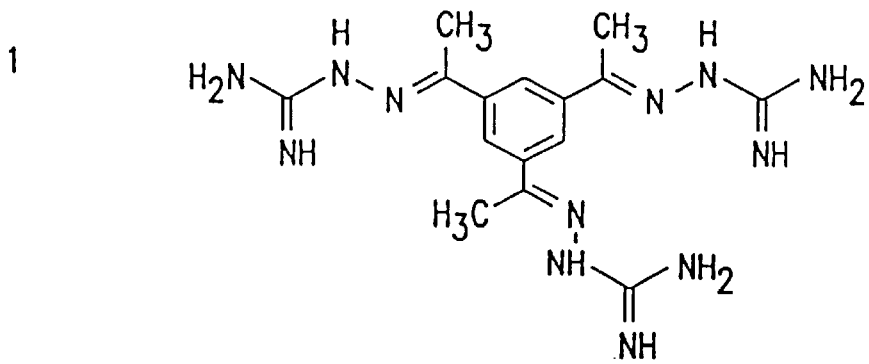
2 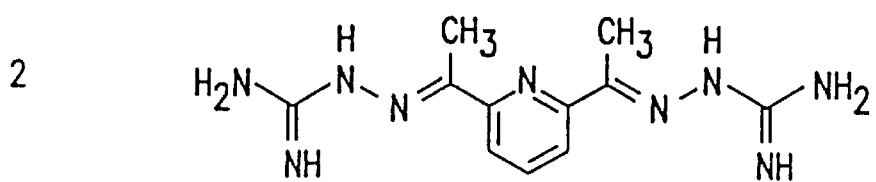
3 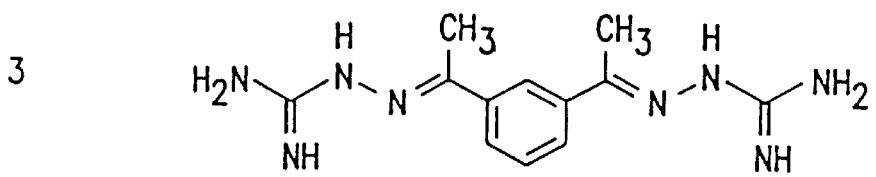
4 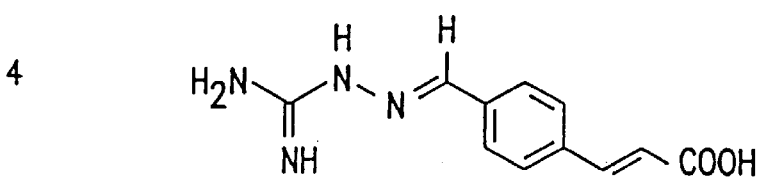
5 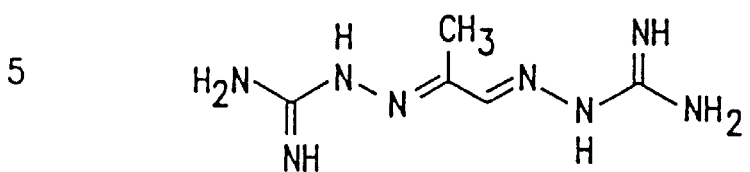
6 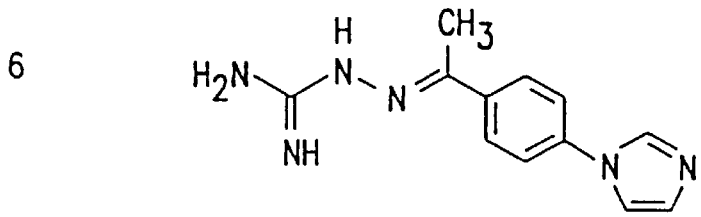
7 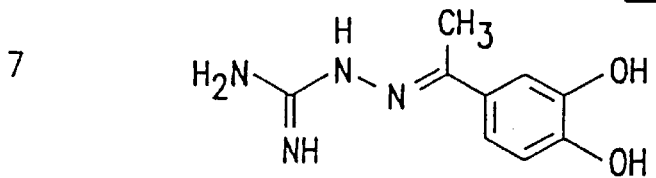
FIG. 7A 8 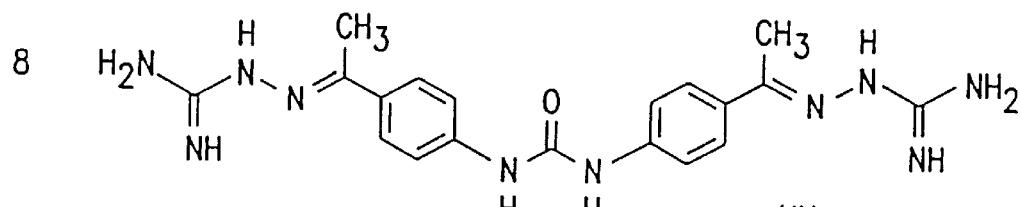
9 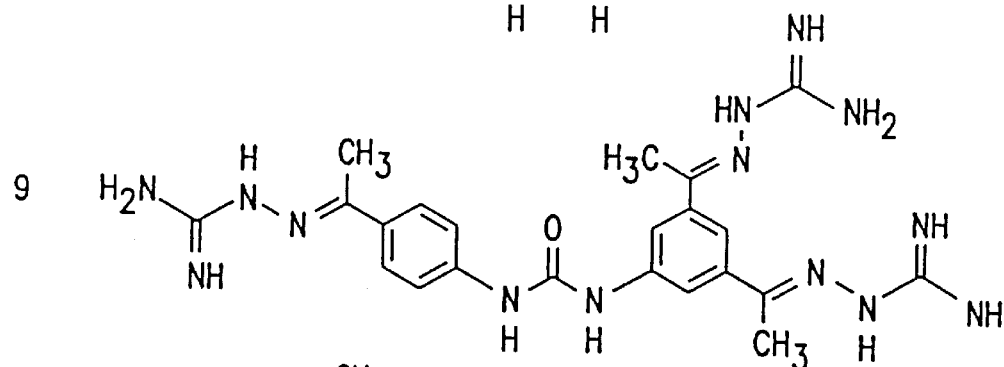
10 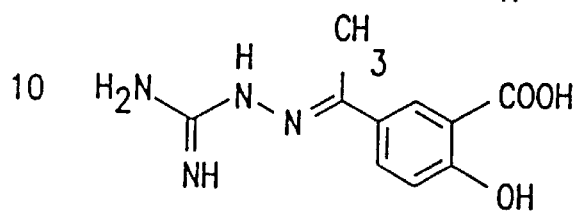
11 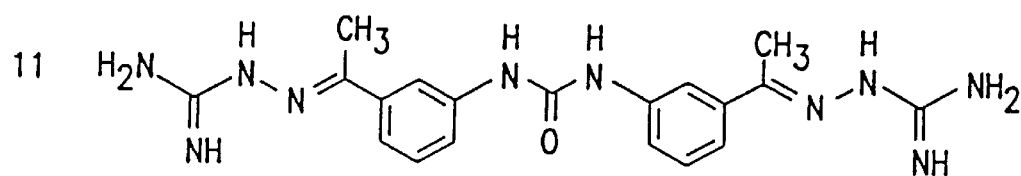
12 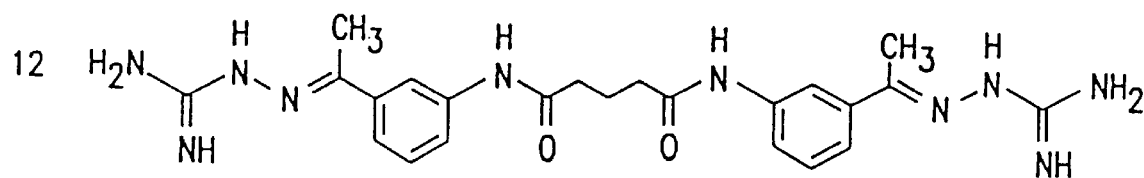
13 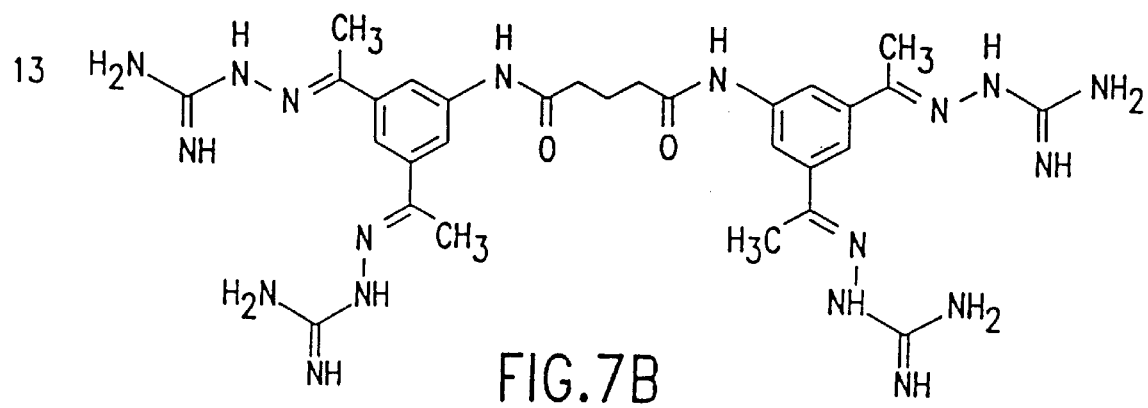
FIG.7B 14
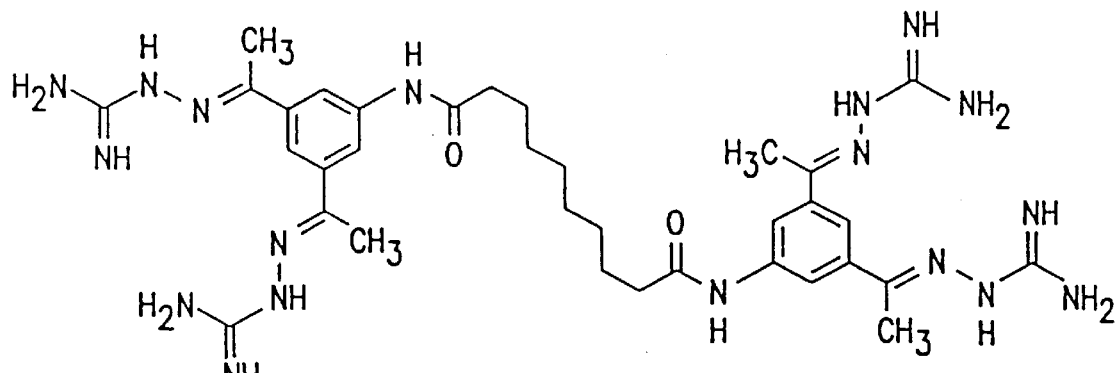
15
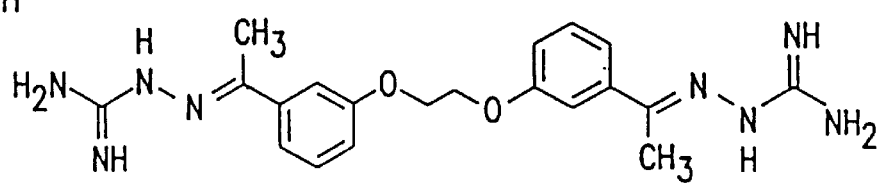
16
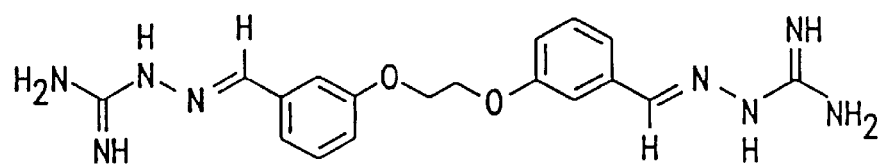
17
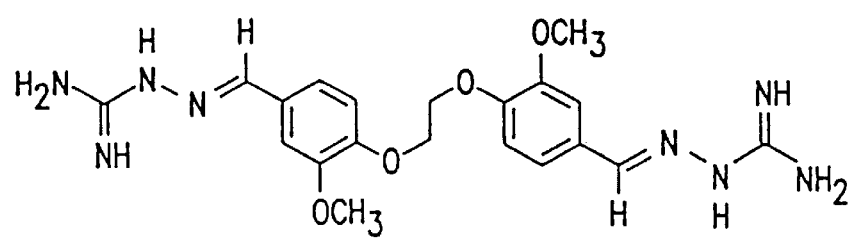
18
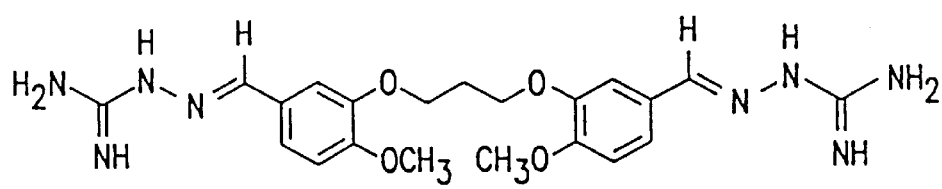
19
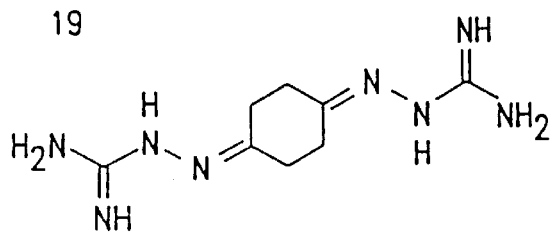
20
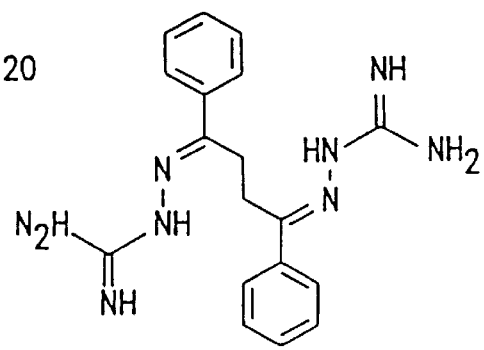
FIG.7C

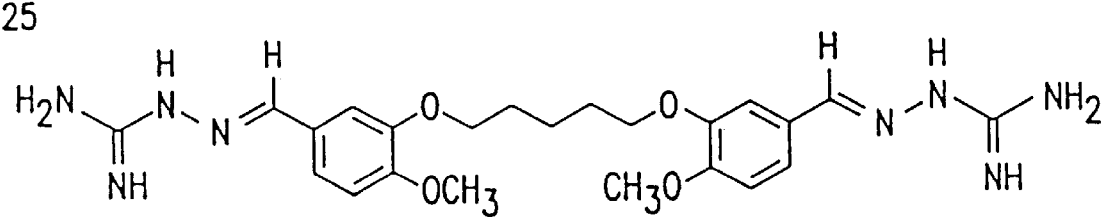
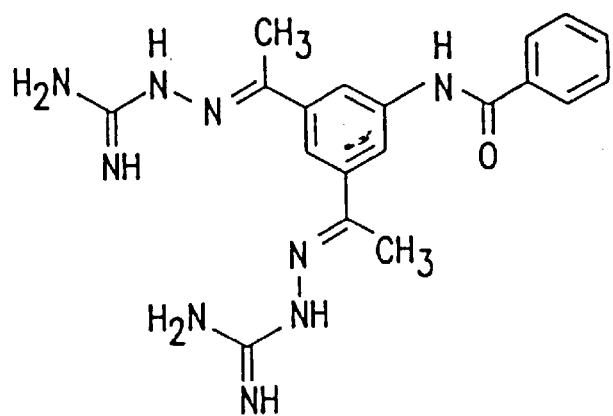
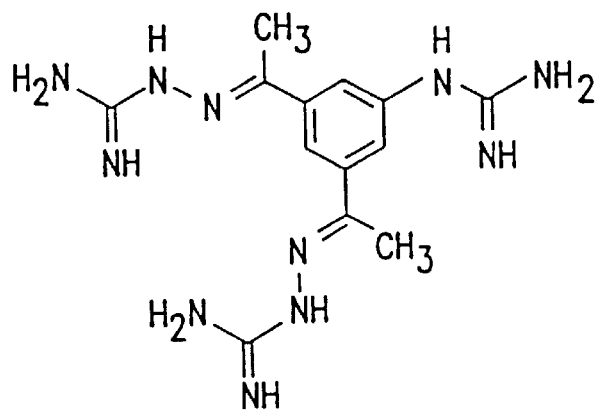
FIG.7E

28
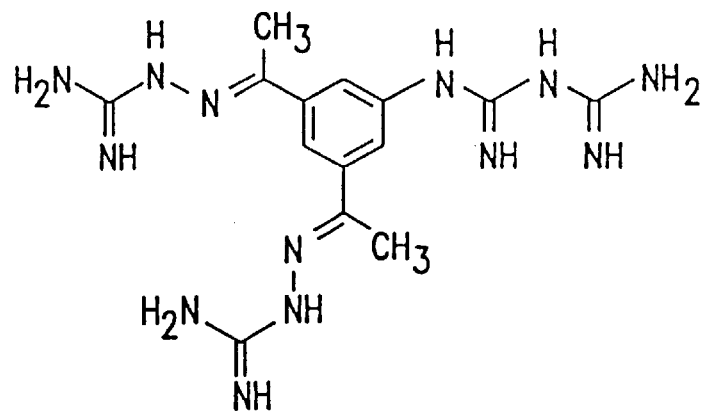
29
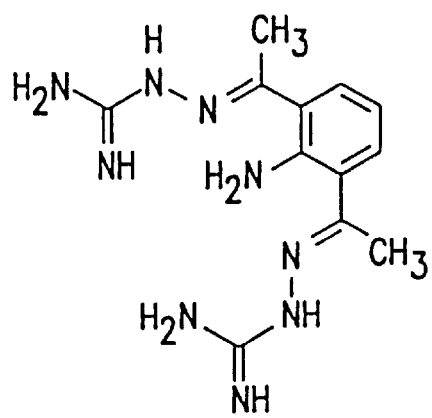
30
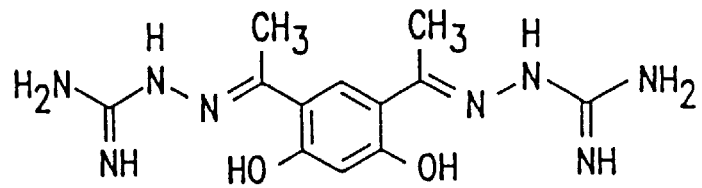
FIG.7F

31
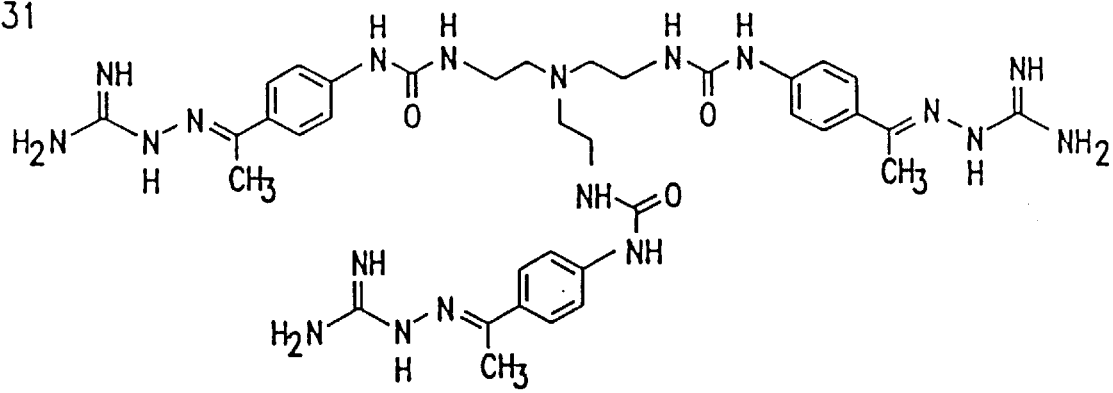
32
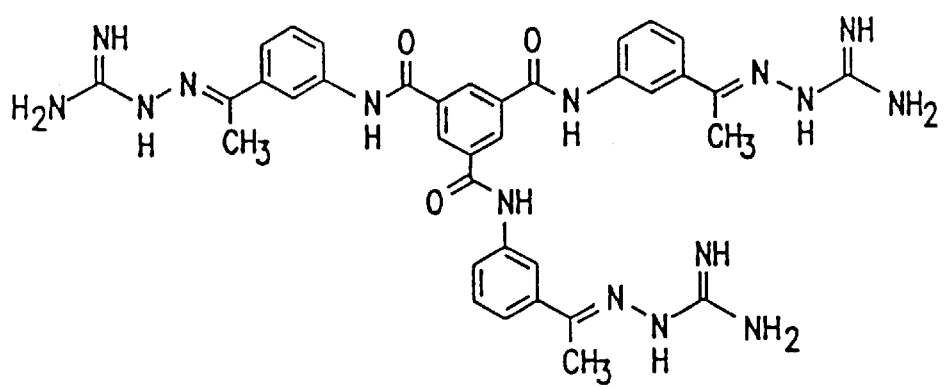
33
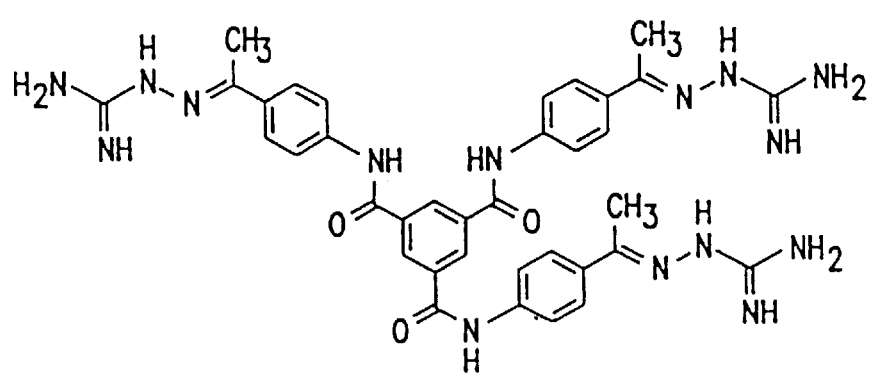
FIG.7G

34
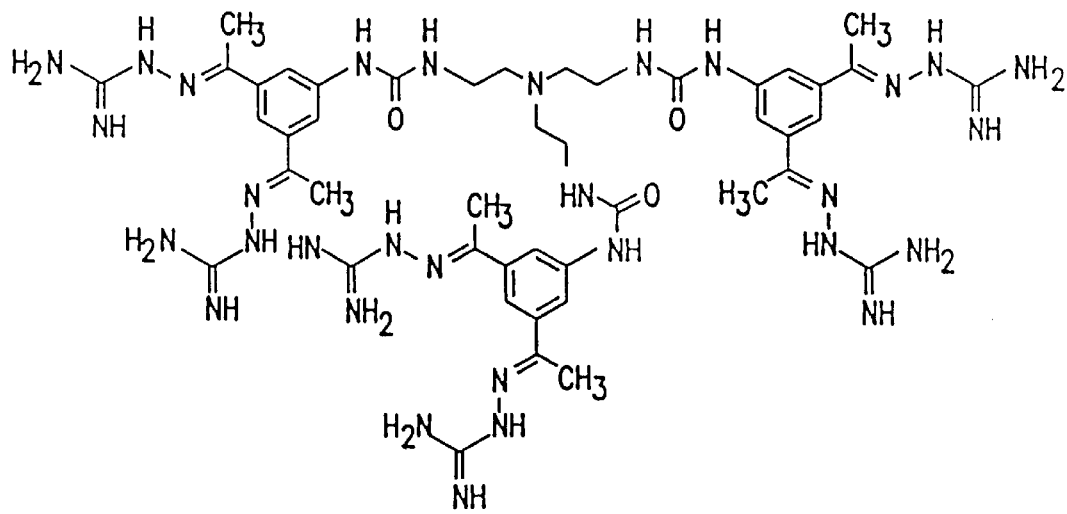
35
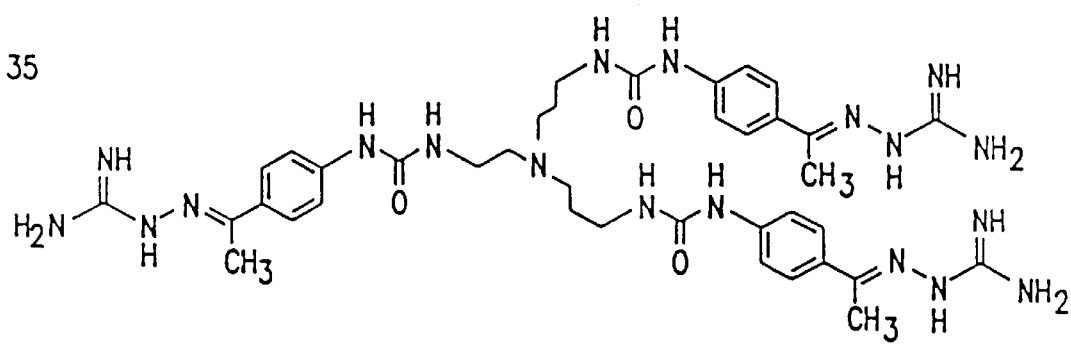
36
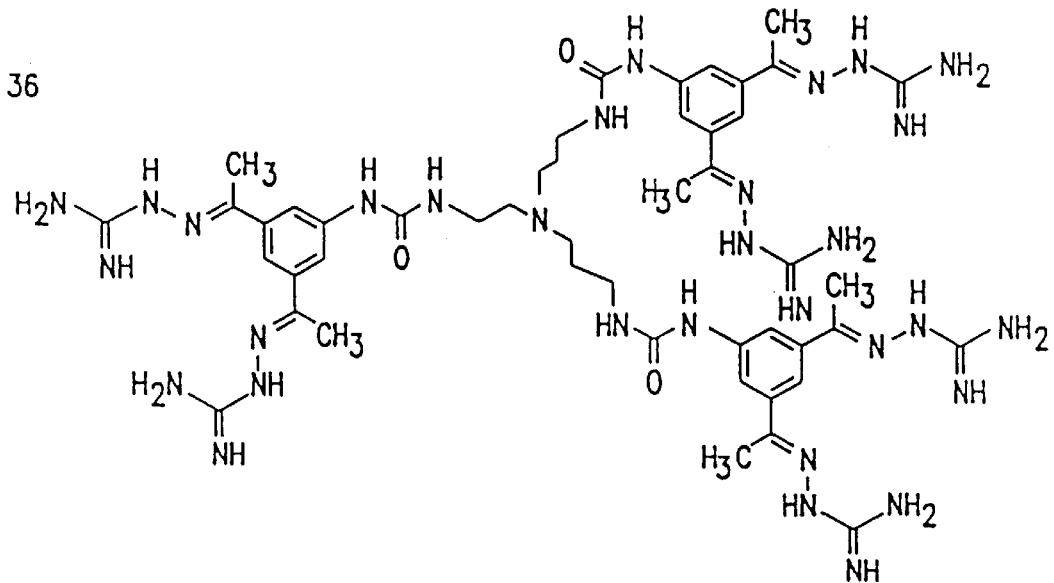
FIG.7H

37
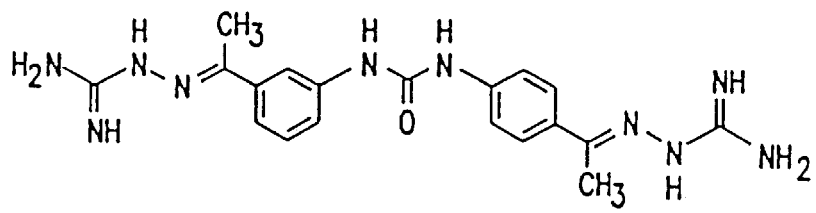
38
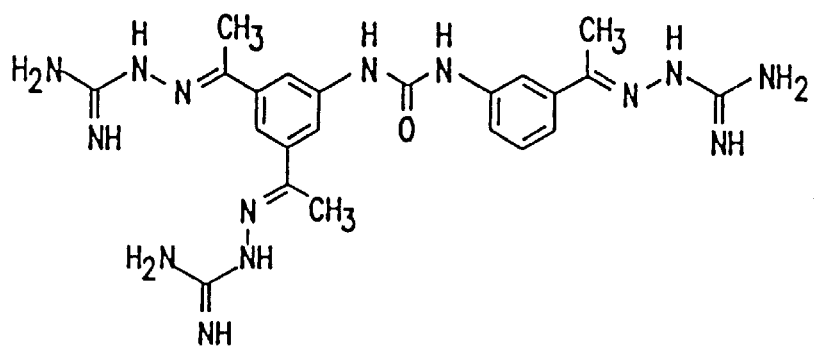
39
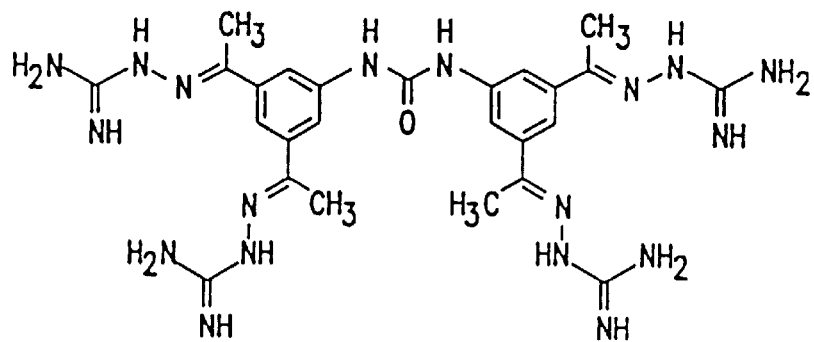
40
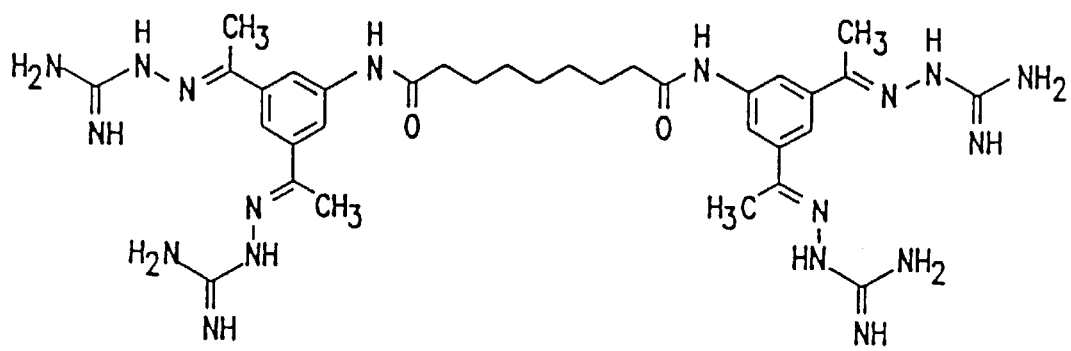
FIG.71

41
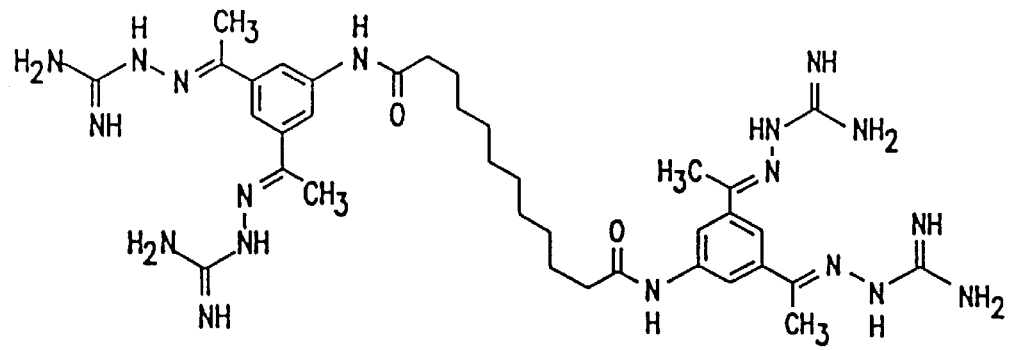
42
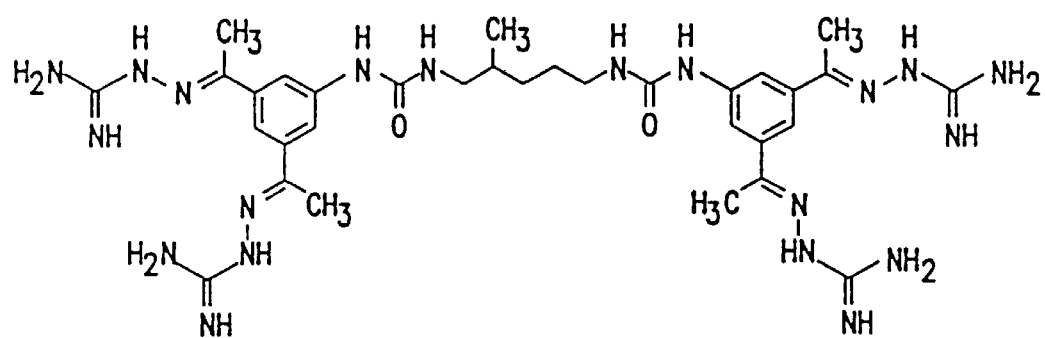
43
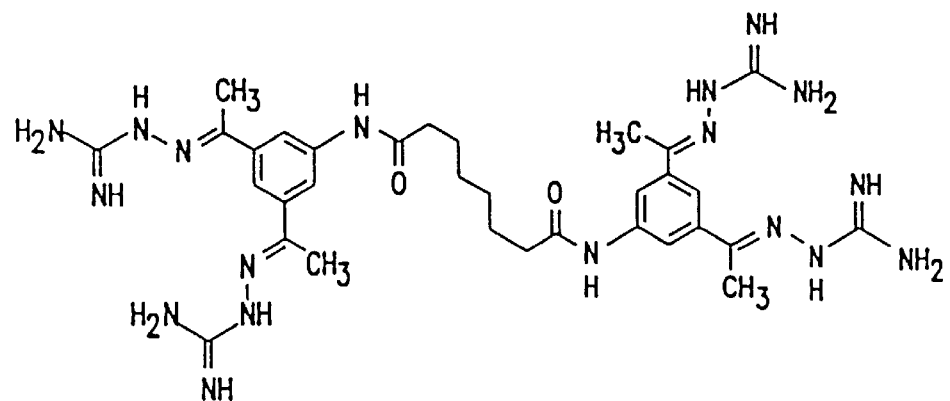
FIG.7J

GUANYLHYDRAZONES AND THEIR USE TO TREAT INFLAMMATORY CONDITIONS

This application is a divisional of U.S. patent application Ser. No. 08/463,568 filed Jun. 5, 1995; which is a continuation-in-part of U.S. patent application Ser. No. 08/315,170 filed Sep. 29, 1994 now U.S. Pat. No. 5,599,984; which is a continuation-in-part of U.S. patent application Ser. No. 08/184,540 filed Jan. 21, 1994, now abandoned.

TABLE OF CONTENTS

1. INTRODUCTION
2. BACKGROUND OF THE INVENTION
   2.1. THE SIGNS OF CACHEXIA ARE DISTINCT FROM THOSE OF STARVATION
   2.2. THE IMPLICATIONS OF THE DIFFERENCES BETWEEN CACHEXIA AND STARVATION
   2.3. THE IMPACT OF THE ROLE OF CYTOKINES INCACHEXIA ON THE SEARCH FOR THERAPIED
   2.4. NITRIC OXIDE AS A MEDIATOR OF ENDOTOXIC SHOCK
3. SUMMARY OF THE INVENTION
4. BRIEF DESCRIPTION OF FIGURES
5. DETAILED DESCRIPTION OF THE INVENTION
   5.1. ASSAYS FOR IDENTIFYING ACTIVE COMPOUNDS
      5.1.1. WHOLE CELL ASSAY FOR UREA AND NITRIC OXIDE PRODUCTION
      5.1.2. WHOLE CELL ASSAY FOR ARGININE UPTAKE
      5.1.3. CELL LYSATE ASSAY FOR ARGINASE ACTIVITY
   5.2. ACTIVE COMPOUNDS
      5.2.1. COMPOUNDS AND THEIR SYNTHESIS
      5.2.2. PHARMACEUTICAL FORMUATIONS
   5.3. USES OF THE COMPOUNDS
6. EXAMPLE: SYNTHESIS OF THE ACTIVE COMPOUNDS
   6.1. SYNTHESIS OF INTERMEDIATE PRODUCTS
      6.1.1. N,N'-BIS(3,5-DIACETYLPHENYL)- PENTANEDIAMIDE
      6.1.2. N -(4-ACETYLPHENYL)-N'-(3,5-DIACETYLPHENYL)UREA
      6.1.3. 1,2-BIS(3-ACETYLPHENOXY)ETHANE
      6.1.4. 1,5-BIS[([(3, 5-DIACETYLPHENYL)-AMINO]CARBONY)LAMINO]-2-METHYLPENTANE
      6.1.5. TRIS[2-([(3-ACETYLPHENYL)AMINO]-CARBONYLAMINO)ETHYL]AMINE
      6.1.6. 3,5-DIACETYLPHENYL ISOCYANATE AND N,N'-BIS(3,5-DIACETYLPHENYL)UREA
   6.2. CONVERSION OF INTERMEDIATE TO END PRODUCTS
   6.3. FURTHER EXEMPLARY COMPOUNDS
7. EXAMPLE: WHOLE CELL INHIBITION ASSAYS FOR UREA AND NO OUTPUT
   7.1. MATERIAL METHODS
   7.2. RESULTS
8. EXAMPLE: WHOLE CELL INHIBITION ASSAYS FOR ARGININE UPTAKE
   8.1. MATERIAL METHODS
   8.2. RESULTS
9. EXAMPLE: ARGINASE INHIBITION ASSAY
   9.1. MATERIAL METHODS
   9.2. RESULTS
10. EXAMPLE: TREATMENT OF CACHEXIA IN VIVO
11. EXAMPLE: TREATMENT OF INFLAMMATION IN VIVO
12. EXAMPLE: COMPOUND NO. 14 HAS NO EFFECTS ON ENDOTHELIAL DERIVED RELAXING FACTOR MEDIATED VASODILATORY RESPONSES
13. EXAMPLE: COMPOUND NO. 14 PREVENTS FATAL ENDOTOXIC SHOCK
14. EXAMPLE: COMPOUND NO. 14 PREVENTS THE PRODUCTION OF CYTOKINES
15. EXAMPLE: COMPOUND NO. 14 CONFERS PROTECTIONN FROM FOCAL CEREBRAL INFARCTION
16. EXAMPLE: ANTI-NEOPLASTIC ACTIVITY OF COMPOUND NO. 14
17. EXAMPLE: INHIBITORY EFFECTS OF COMPOUND NO. 14 ON ARGININE UPTAKE AND NO OUTPUT OF PREVIOUSLY QUIESCENT VERSUS ACTIVATED CELLS
18. EXAMPLE: HIGH-PERFORMANCE LIQUID CHROMATOGRAPHY METHOD AND DETERMINATION OF PHARMACOKINETIC CONSTANTS THEREBY
   18.1. EXPERMENTAL MATERIALS AND METHODS
   19.1. RESULTS

1. INTRODUCTION

This invention concerns new methods and compositions that are useful in treating inflammatory conditions, e.g., preventing and ameliorating cachexia, the clinical syndrome of poor nutritional status and bodily wasting associated with cancer and other chronic diseases. More particularly, the invention relates to aromatic guanylhydrazone ("Ghy", more properly termed amidinohydrazone, i.e., $NH_2(CNH)$—NH—N=) compositions and their use to inhibit the uptake of arginine by macrophages and/or its conversion to urea. These compositions and methods are also useful in preventing the generation of nitric oxide (NO) and the secretion of cytokines by macrophages and other cell types, and so to prevent NO-mediated inflammation and other responses in persons in need of same. In another embodiment, the compounds can be used to inhibit arginine uptake in arginine-dependent tumors and infections.

2. BACKGROUND OF THE INVENTION

Cachexia is a syndrome characterized by the wasting of tissue mass in diseased animals, and is grossly reflected as a loss of host weight. Cachexia is a progressive and often fatal complication found in many different chronic disease states and its consequences require that the goals of therapy should not be solely to redress the underlying disease. The loss of protein stores, loss of body weight and generally poor nutritional status of cachectic patients can be independent sources of morbidity and mortality. Also, the debilitation associated with cachexia is a significant limitation on the patient's ability to tolerate aggressive medical and surgical therapies which are directed to the primary etiology.

2.1. The Signs of Cachexia are Distinct from Those of Starvation

Cachexia is a severe, often life-threatening complication commonly encountered in association with a variety of insults: cancer, chemotherapy, radiation injury, chronic infection, trauma and surgical stress. Food intake insufficient to meet the total energy needs of the host is a constant element of the cachectic syndrome. In addition to this relative hypophagia which is a defining feature of cachexia, anorexia is also frequently encountered.

However, studies of the syndrome indicate that cachexia is not simply due to a dietary intake of protein and carbohydrate below the needs of the host. Cachexia differs from unstressed caloric deprivation in that the pattern of wasting seen during partial or complete starvation is associated with an initial whole body lipid loss concurrent with a relative conservation of tissue protein. By contrast, cachexia is characterized by the significant loss of both lipid and protein from tissue reservoirs

2.2. The Implications of the Differences Between Cachexia and Starvation

The most commonly accepted general explanation for cachexia is that the host's proteins are broken down in the tissues to provide a source of amino acids. These amino acids in turn are thought to be needed for the synthesis of glucose, albumin and host defense proteins in the liver.

This well-accepted theory suggests that therapies directed toward increasing the total intake of calories and proteins should substantially ameliorate the cachectic syndrome. However, even as drastic an intervention as total parenteral nutrition is not able to effectively treat cachexia. (Brennan, 1986 NEJM 305:375, Detsky, et al., 1987, ANN INTERN MED 107:195, McGeer, et al., 1989, ANN INTERN MED 110: 734, Koretz, 1984, J CLIN ONCOL 2:534).

In addition to the failure of supplementary nutrition as a therapeutic modality, the fundamental difference in the pattern of the losses of lipid and protein between cachexia and starvation also indicates that cachexia is neither the result solely of the abnormally increased nutritional needs due to the underlying disease nor of anorexia due to the disease's disruption of the physiologic regulation of appetite. Rather the differences suggest the presence of some fundamental changes in the host's metabolism due, directly or indirectly, to the underlying disease.

Further supporting this conclusion has been an accumulation of evidence implicating soluble host-produced regulatory and effector proteins, known as cytokines, in the chain of events which leads to cachexia. Experiments have been conducted in which the blood circulation of a normal and a cachectic animal were joined. In these experiments with so-called "parabiosed" animals, it was observed that the otherwise normal animal rapidly developed cachexia although the underlying disease remains entirely with the original host. These and other observations strongly implicate circulating mediators as the proximal cause of cachexia, i.e., this catabolic condition is not the passive result of the excessive metabolic demands imposed by the growth of the invading cells or organisms, nor the simple result of a lesser food intake than that required to meet metabolic demands.

One possibility as to the identity of these humoral factors was that the soluble mediators produced in cachexia were the same molecules as had been already identified as host immune/inflammatory-related molecules (cytokines), and shown to be secreted by lymphocytes and macrophages. The theory that these cytokines were involved in cachexia was confirmed by the observation that the administration of exogenous Tumor Necrosis Factor (also known as cachectin, herein abbreviated "ITNF") to test animals mimicked many features of cachexia. (Darling et al., 1990, CANCER RES 50:4008; Beutler & Cerami, 1988, ADV IMMUNOL 42:213). Further, anti-TNF antisera are able to ameliorate many, but not all, the signs of cachexia in experimental tumor systems. (Sherry, et al., 1989, FASEB J 3:1956; Langstein, et al., 1989, SURG FORUM 15: 408).

2.3. The Impact of the Role of Cytokines in Cachexia on the Search for Therapies It should be clear that even if all aspects of the cachectic syndrome were attributable to some single cytokine or, alternatively, to the activity of some combination of several cytokines, hormones and other humoral factors, such knowledge would not in and of itself provide a cellular or biochemical mechanism to explain the metabolic changes that underlie cachexia, nor lead directly to an effective therapy. Ultimately, cytokines must interact with target cells and induce metabolic or phenotypic changes in their targets to be of physiological and pathophysiological significance. Thus the general identification of cytokine mediation and the specific implications of particular cytokine mediators are only intermediate objectives in the determination of precisely what cellular and/or systemic metabolic changes occur to bring about the full cachectic picture.

The findings that implicate cytokines as mediators of the various cachectic syndromes, combined with the widespread focus on liver and peripheral muscle as major contributors to the metabolic changes of cachexia prompted many to look at the effects of known cytokines on liver and muscle cells and to search for new cytokines having an effect on these tissues.

To date, however, no known cytokines, individually or in combination, have been shown to directly mobilize amino acids from protein stores in in vitro systems using cells typical of these presumed sites of protein breakdown in vivo.

2.4. Nitric Oxide as a Mediator of Endotoxic Shock

Nitric oxide (NO), a molecule produced enzymatically from L-arginine by nitric oxide synthase (NOS), is a mediator of both physiological homeostasis and inflammatory cytotoxicity. Moncada, S. & Higgs, A., 1993, The New England Journal Of Medicine 329, 2001–2012; Nathan, C., 1992, FASEB J 6, 3051–3064. NO production via the constitutive and inducible isoforms of NOS in endothelial cells for instance, causes vasodilation and governs blood pressure and tissue perfusion. Kilbourn, R. G., Jubran, A., Gross, S. S., et al., 1990, Biochem. Biophys. Res. Commun. 172, 1132–1138. NO production by an inducible NOS in activated macrophages, on the other hand, confers cytotoxic, increases vascular permeability, and enhances the release of TNFα and IL-1. Ding, A. H., Nathan, C. F. & Stuehr, D. J. *J Immunol.* 141, 2407–2412 (1988); Kubes, P. & Granger, D. N. *Am. J. Physiol.* 262, H611–H615 (1992); Van Dervort, A. L., Yan, L., Madara, P. J., et al. *J Immunol.* 152, 4102–4109 (1994); Bouskela, E. & Rubanyi, G. M. *SHOCK* 1, 347–353 (1994); Hibbs, J. B., Taintor, R. R. & Vavrin, Z. *Science* 235, 473–476 (1987); Granger, D. L., Hibbs, J. B., Perfect, J. R. & Durack, D. T. *J. Clin. Invest.* 85, 264–273 (1990). Insight into the diverse biological actions of NO has been facilitated by compounds that interfere with NOS to inhibit production of NO. Because the NOS isoforms are highly conserved, however, the available NOS inhibitors have not been found to discriminate significantly between the activities of constitutive versus inducible NOS.

Previously available NOS inhibitors have had limited success in improving survival from endotoxemia, in part because they indiscriminately suppress endothelial-derived relaxing factor (EDRF), Cobb, J. P., et al., 1992, J. Exp. Med. 176: 1175–1182; Minnard, E. A., et al., 1994, Arch Surg. 129:142–148; Billiar, T. R., 1990, et al., J Leukocyte Biol. 48:565–569. Suppression of EDRF during endotoxemia may impair survival by causing vasoconstriction and a diminution of blood flow to critical vascular beds. Hertofore there have been reported no compounds that inhibit cytokine-inducible macrophage NO without also inhibiting endothelial-derived NO.

3. SUMMARY OF THE INVENTION

The present invention relates to methods and compounds for treating cachexia by inhibiting the production of urea, more particularly the production of urea by macrophages and the inhibition of the transport processes which mediate arginine uptake, particularly by macrophages. The method of the invention may also be used to limit or prevent the damage induced by NO-mediated responses associated with stroke, shock, inflammation and other NO-related conditions. Another object of the invention relates to inhibiting arginine uptake in the treatment of tumors or infections, where the tumor cells, the infected cells or the infectious agent requires arginine. A further object of the invention is the inhibition of the deleterious secretion of cytokines, such as Tumor Necrosis Factor, by activated macrophages.

The class of compounds useful for the purposes of the invention includes but is not limited to aromatics substituted with multiple guanylhydrazone (Ghy) moieties, more properly termed amidinohydrazones. The synthesis and use of such compounds is described. The invention further encompasses screening assays to test additional compounds for the above-noted activities, and pharmaceutical compositions useful in the practice of this method of therapy.

Because of the close relationship between urea production and the physiological synthesis of nitric oxide, the compounds of this invention can also be effective in limiting the cellular production of NO, particularly by macrophages.

While not limited to any theory of how or why the therapies described and claimed herein operate, the invention is based, in part, on the Applicants' development of the following model for cachexia: in cachexia, activated macrophages deplete the host's nitrogen pool by converting circulating arginine to nitrogenous end products that are eliminated from the body, requiring protein catabolism by the muscle and/or liver and other organs in order to replace the lost serum arginine. Thus, activated macrophages create a "nitrogen sink" that persistently drains nitrogen from the systemic pool, forcing the body to compensate by catabolizing tissue proteins to liberate amino acids as new sources of nitrogen. The model is based on the Applicants' experiments, that, while seeking to identify a factor released by activated macrophages which caused other tissues to make urea, found that activated macrophages themselves directly synthesize urea by breaking down arginine.

Figure 1:
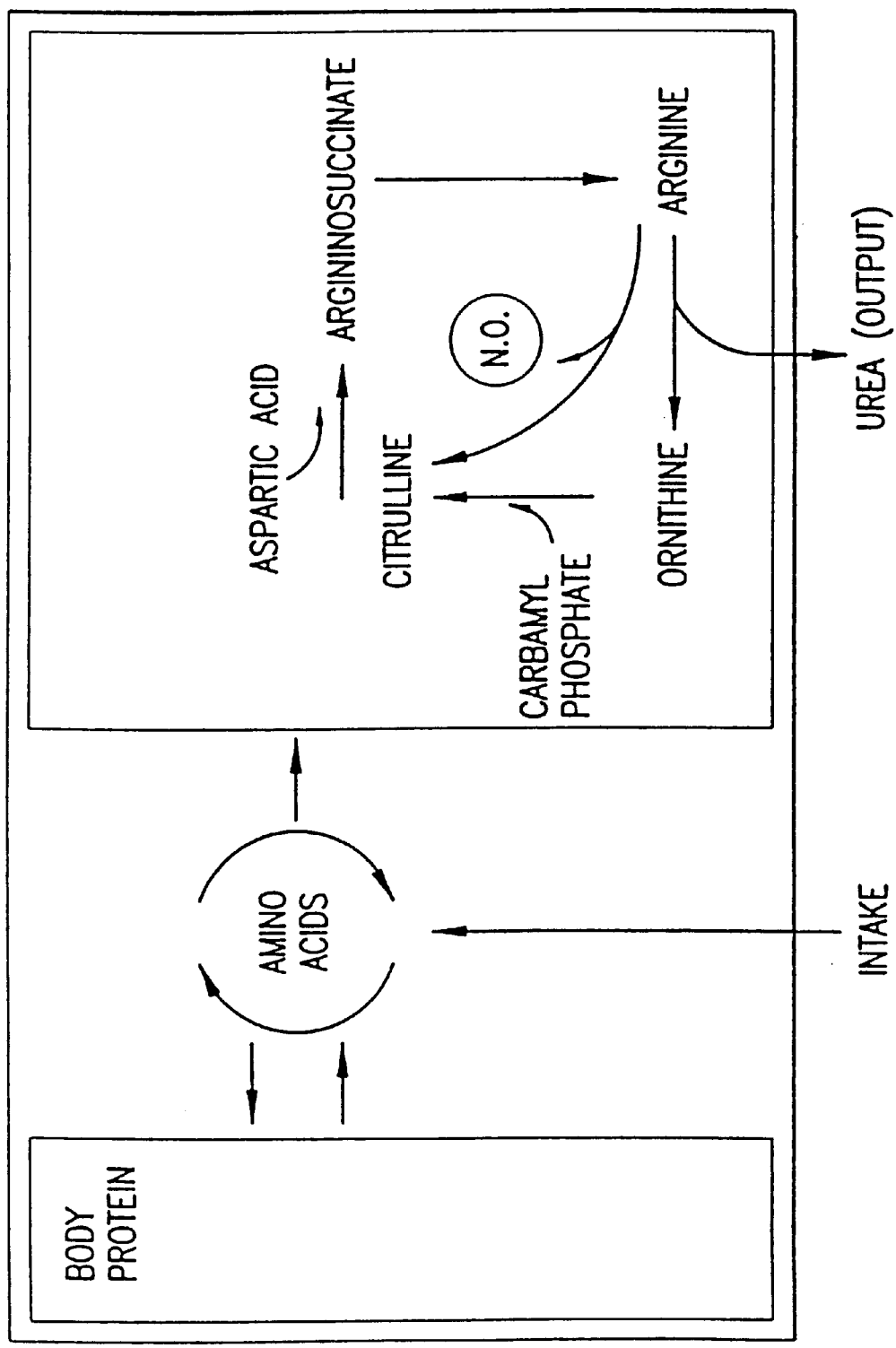

Activated macrophages break down arginine in two ways: (a) into urea and ornithine, or (b) into citrulline and nitric oxide (FIG. 1). The urea and nitric oxide so generated remove nitrogen from the whole body nitrogen pool since these metabolites cannot be efficiently recycled for reuse. Therefore, in cachexia, activated macrophages deplete the plasma of arginine. The body's mechanisms to maintain arginine homeostasis in the plasma will then require catabolism of protein from the muscle, liver and other organs to liberate sources of nitrogen and arginine. The discovery that arginine breakdown in the activated macrophage is a proximal cause of the inappropriate mobilization of tissue protein stores allowed for the development of the therapies described herein—i.e., interfering with arginine uptake by activated macrophages, and/or the production of urea from arginine to stem the inexorable loss of urea down the metabolic "nitrogen sink" and thus inhibit the further catabolism of protein from the tissues.

It is a further object of invention to provide compounds and methods of their use to inhibit the production of nitric oxide by macrophages to overcome the limitation imposed by the absence of a macrophage-specific inhibitor of nitric oxide synthetase. Without limitation as to theory, we reasoned that advantage could be made of the requirement for arginine uptake by macrophages but not endothelial cells induced to produce NO. The compounds of the present invention were found to inhibit the production of NO by macrophages while having no inhibition on the production of vaso-active (endothelial derived) NO. Thus, the compounds of the invention may advantageously be used to counteract macrophage-induced, NO-mediated effects which accompany, for example, endotoxic and septic shock.

The foregoing is presented by way of illustration and not limitation. While the invention was developed with the background knowledge of the model for the physiology of cachexia, the invention itself involves the use of arginine analogs, arginomimetics, and other compounds having a non-metabolizable guanylhydrazone group(s) to inhibit the macrophage production of urea. A general class of such compounds are aromatics containing guanylhydrazones. These compounds can be synthesized by the reaction of acetylbenzenes and benzaldehydes with aminoguanidine and acid at high temperature in aqueous ethanol. (Ulrich, et al., 1982, Drug Development Research 2:219; and Ulrich & Cerami, 1984 Medicinal Chemistry 27:35, which are hereby incorporated by reference.) The invention is demonstrated by working examples describing the synthesis of compounds used in accordance with the invention (Section 6, infra); a whole cell assay to identify compounds that inhibit urea output (Section 7, infra); a whole cell assay to identify compounds that inhibit arginine uptake (Section 8, infra); an arginase inhibition assay (Section 9, infra); the demonstration of efficacy of the invention in an animal model system for cachexia (Section 10, infra); the demonstration of efficacy of the invention to reduce inflammation in the animal model using carrageenan-induced paw swelling (Section 11, infra); the demonstration of in vivo efficacy of the invention in preventing lipopolysaccharide-induced fatality (Section 13, infra) without blocking the effects of endothelial-derived relaxing factor (Section 12, infra) and of in vitro efficacy of the invention in preventing the secretion of Tumor Necrosis Factor by RAW 264.7 cells stimulated by LPS and γ-interferon (Section 14, infra). The results of Sections 12–14 are indicative of efficacy in preventing the morbidity and mortality associated with toxic shock or sytemic inflammatory response syndrome. Further examples show the efficacy of Compound No. 14 in reducing the severity of infarction induced by occlusion of the middle cerebral artery of a rat (Section 15, infra) and in reducing the growth of an experimental neoplasm in a nude mouse model (Section 16, infra).

4 BRIEF DESCRIPTION OF FIGURES

FIG. 1. Biochemistry of arginine degradation by inflammatory cells and inter-organ substrate cycling.

Figure 2:
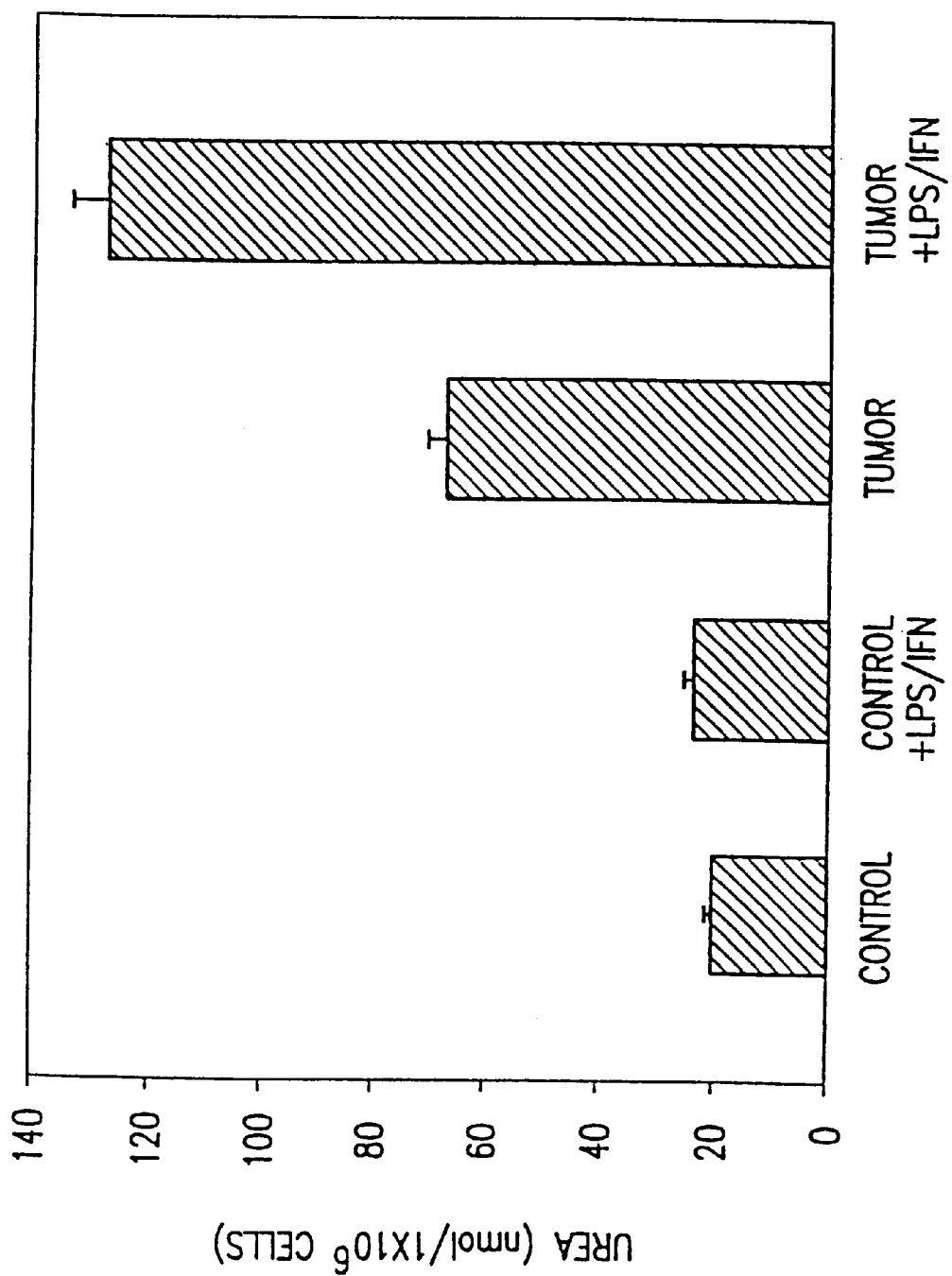

FIG. 2. Urea production by resident macrophages.

Figure 3:
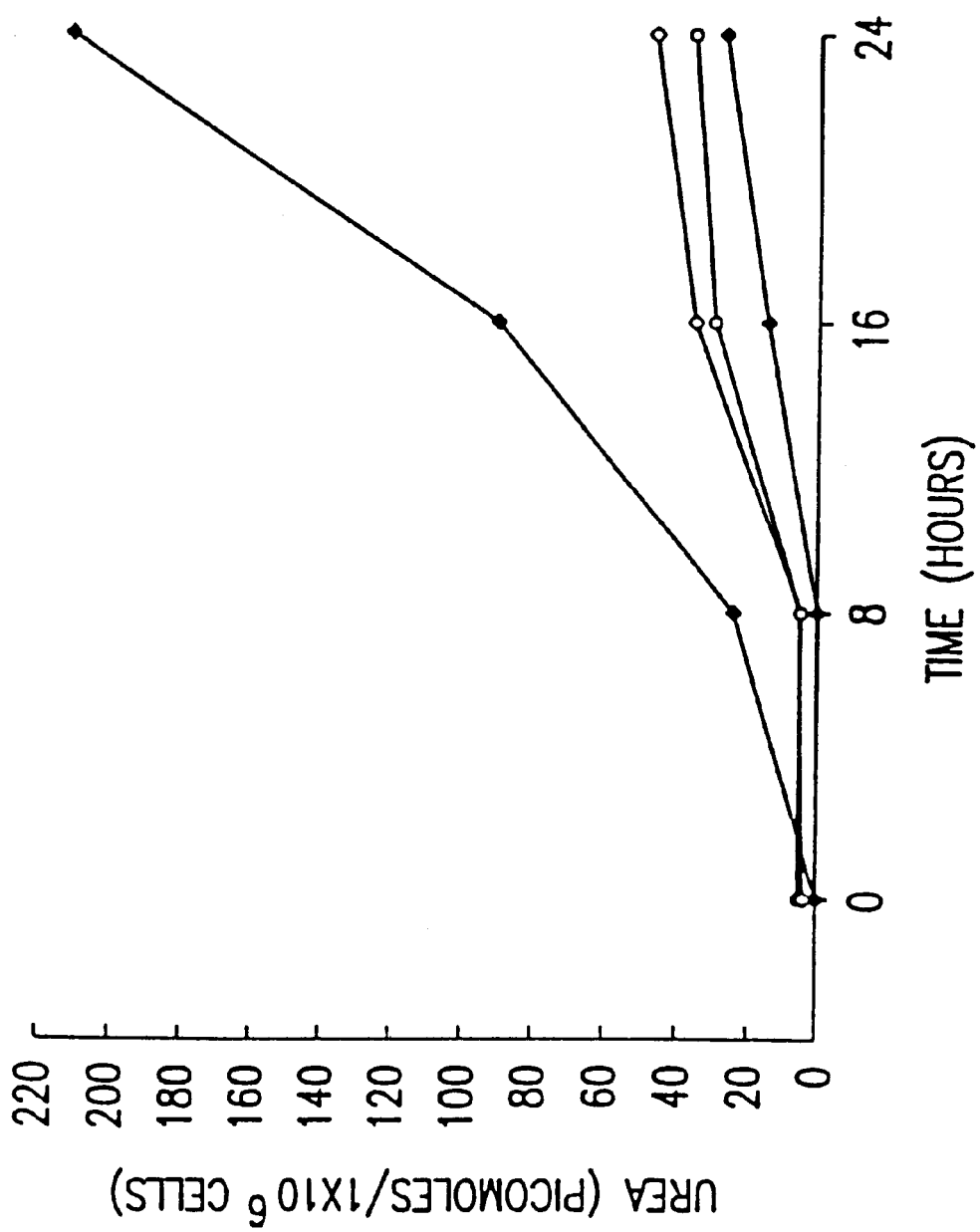

FIG. 3. Urea production by macrophages is stimulated by LPS and γ-interferon. Control -○-; IFNγ (25 U/ml) -●-; LPS (100 ng/ml) -◇-; IFNγ (25 U/ml)+LPS (100 ng/ml) -◆-.

FIG. 4. Dose-response relationship of the effect of γ-interferon and LPS on RAW 264.7 cell production of urea in the presence and absence of complementary drugs.

FIG. 4A. Various doses of γ-interferon with and without 100 ng/ml LPS;

FIG. 4B. Various doses of LPS with and without 25 U/ml γ-interferon.

Figure 5:
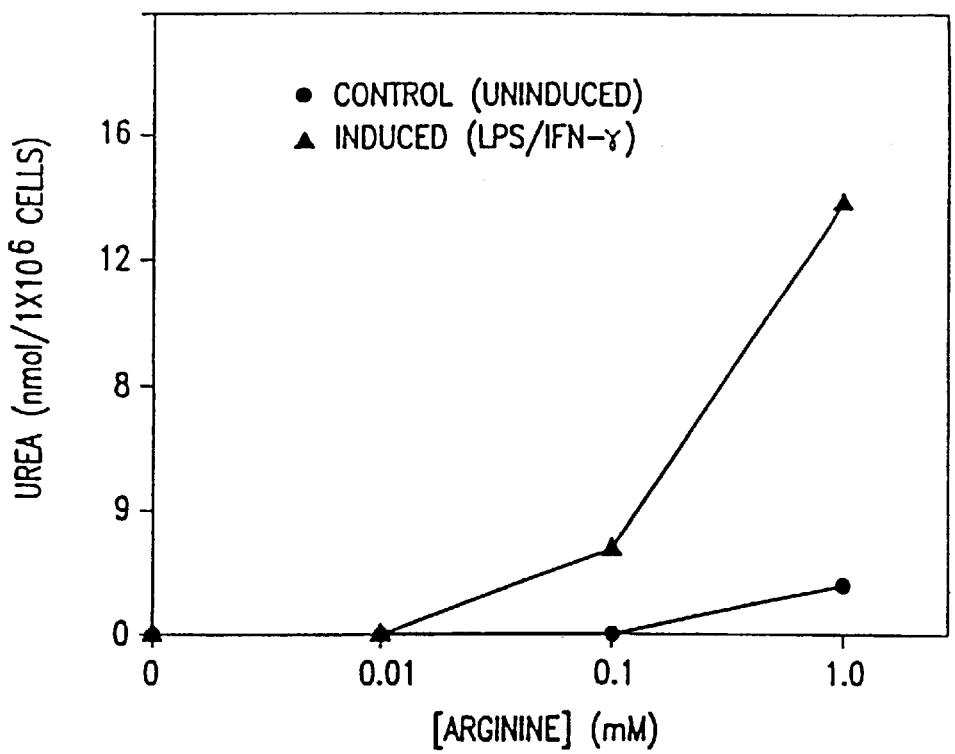

FIG. 5. Dependence of RAW 264.7 urea production on extracellular arginine. Control -●-; IFNγ (25 U/ml)+LPS (100 ng/ml) -▲-.

Figure 6:
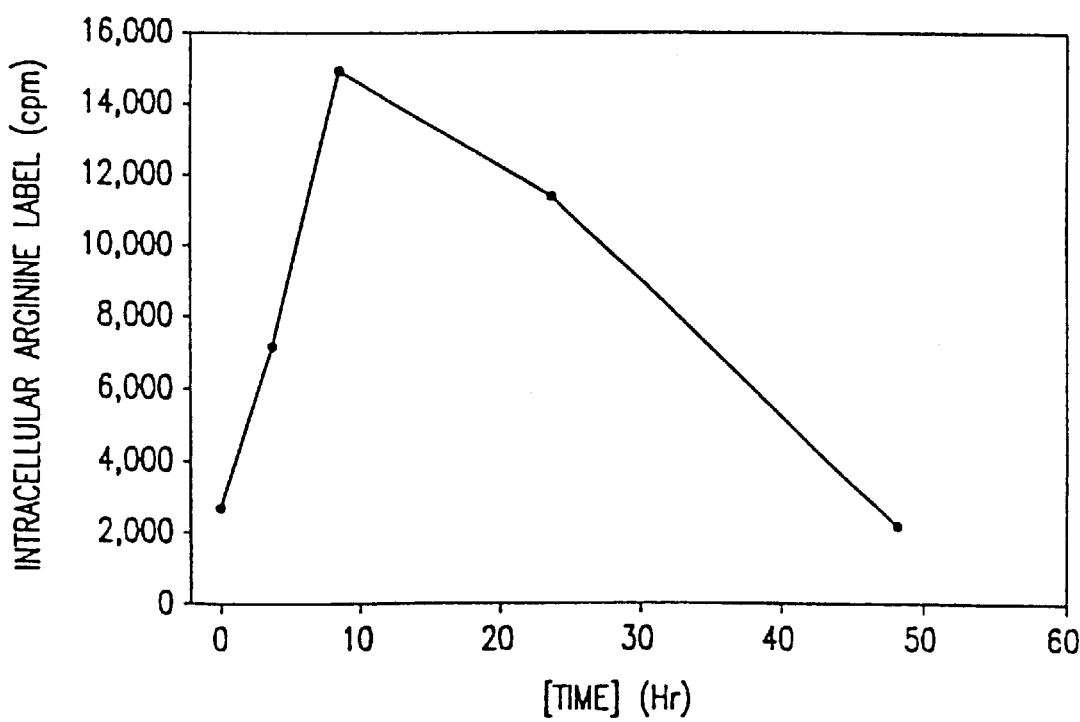

FIG. 6. Arginine transport. Uptake of tetra-$^3$H-arginine by RAW 264.7 cells a various times after stimulation.

FIG. 7. Chemical structures of exemplary compounds of the invention.

FIG. 7A. Nos. 1–7;

FIG. 7B. Nos. 8–13;

FIG. 7C. Nos. 14–20;

FIG. 7D. Nos. 21–24;

FIG. 7E. Nos. 25–27;

FIG. 7F. Nos. 28–30;

FIG. 7G. Nos. 31–33;

FIG. 7H. Nos. 34–36;

FIG. 7I Nos. 37–40;

FIG. 7J. Nos. 41–43.

FIG. 8. The dose dependency of the protective effects Compound No. 14 on λ-carrageenan induced mouse paw swelling.

Figure 9:
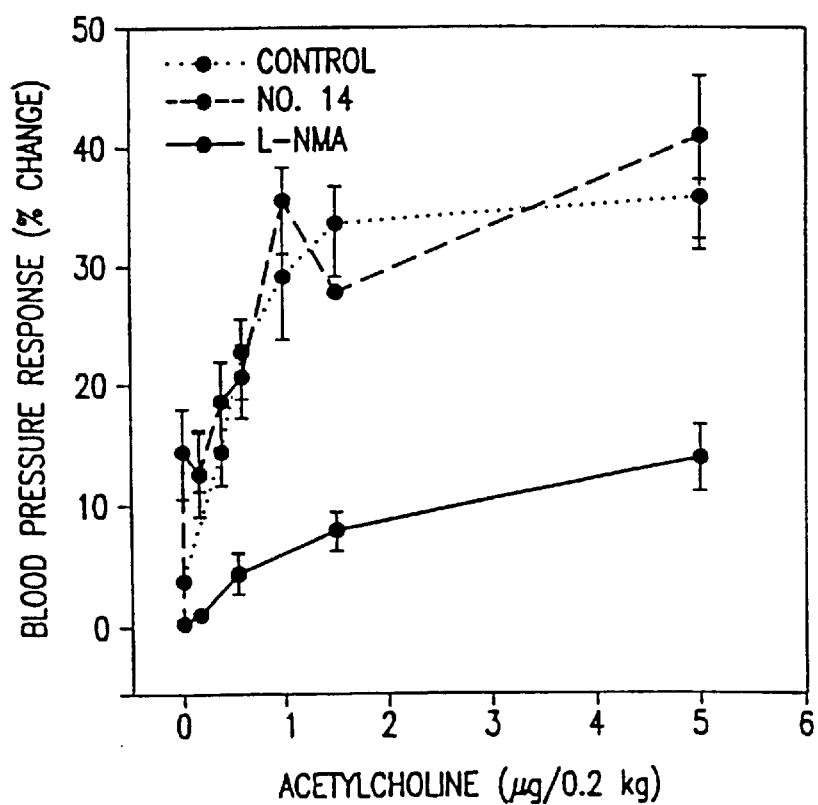

FIG. 9. Comparison of the effect on acetylcholine-induced hypotension of Compound No. 14 and of the known nitric oxide synthase inhibitor, L-$N^G$-methyl-arginine.

Figure 10:
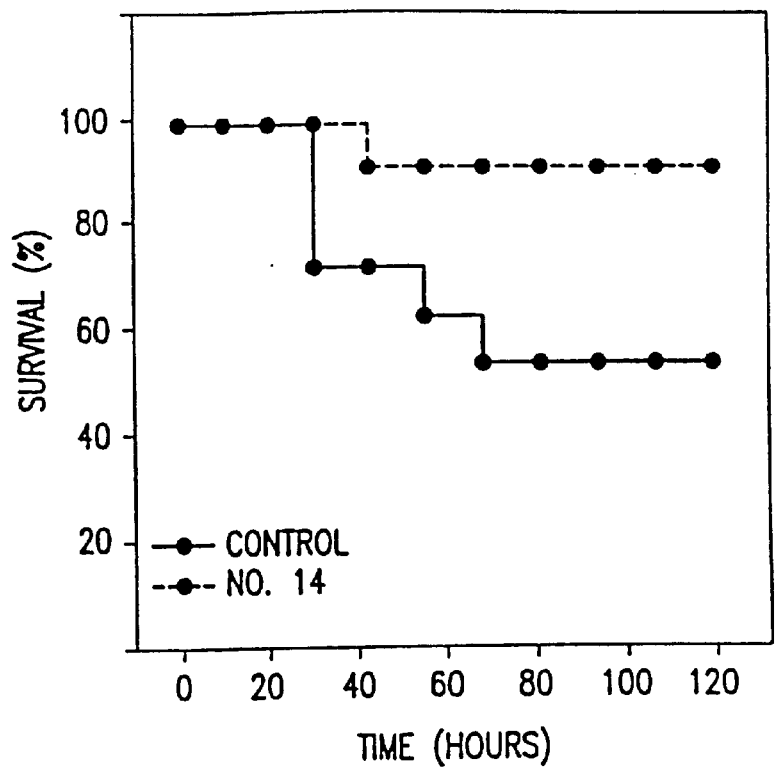

FIG. 10. Effects of Compound No. 14 on LPS-induced mortality.

Figure 11:
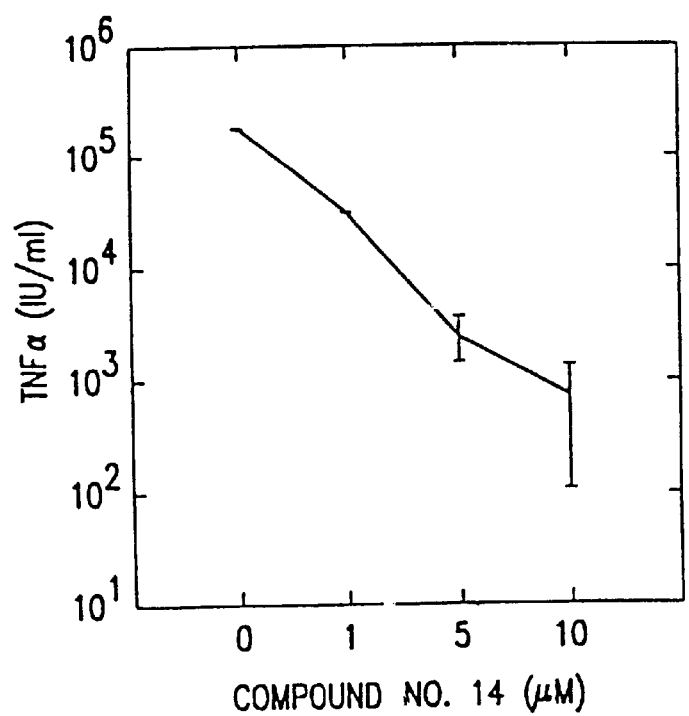

FIG. 11. Effects of Compound No. 14 on the secretion of TNF by LPS/γ-interferon-stimulated RAW 264.7 cells.

Figure 12:
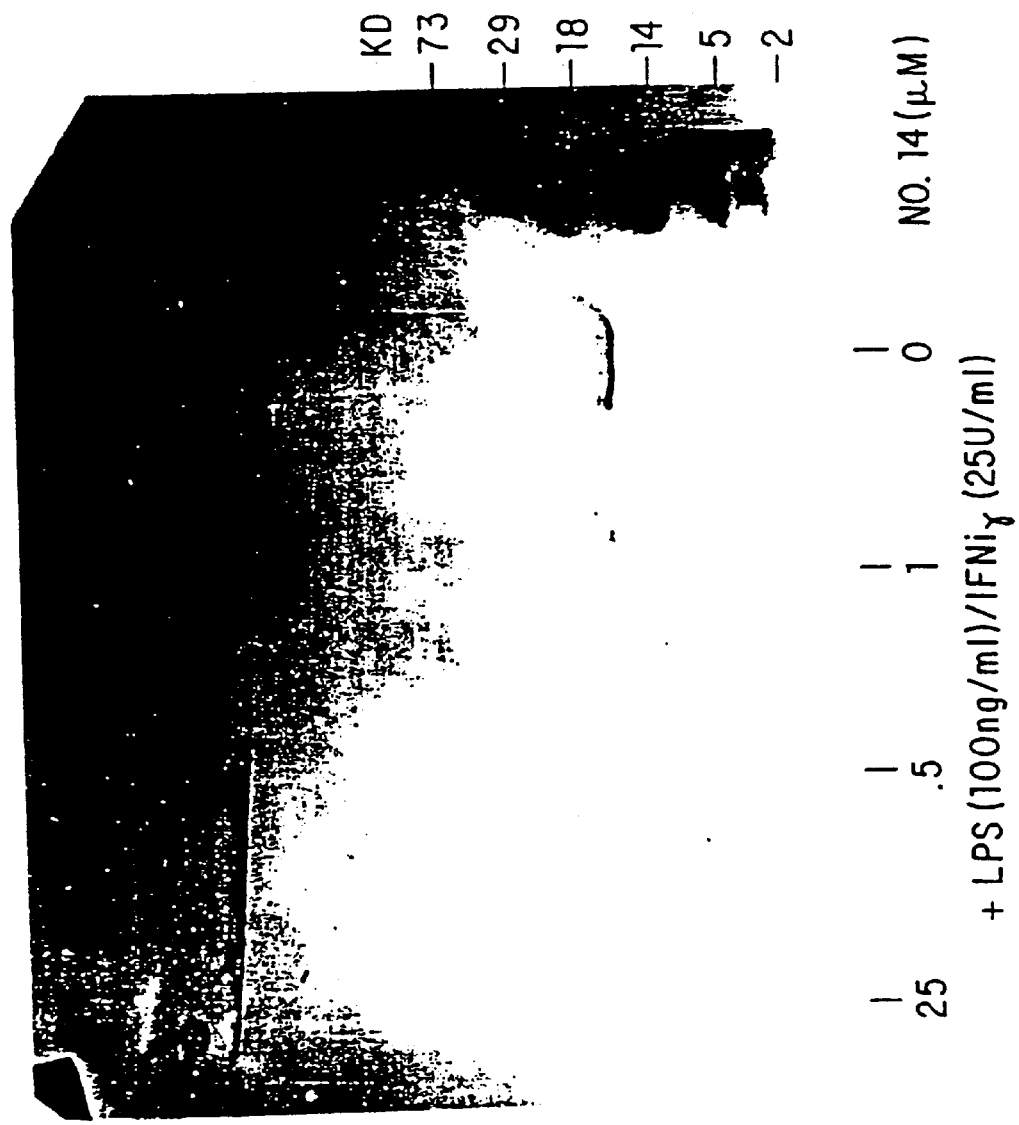

FIG. 12. Western blot of medium from LPS/γ-IFN-stimulated RAW 264.7 cells showing the production of TNF by cells treated with 0, 1, 5 and 25 μM Compound No. 14.

FIG. 13. Comparison of the combined effects of Compound No. 14 and extracellular arginine on the production of NO and TNF by LPS/γ-IFN-stimulated RAW 264.7 cells.

Figure 13A:
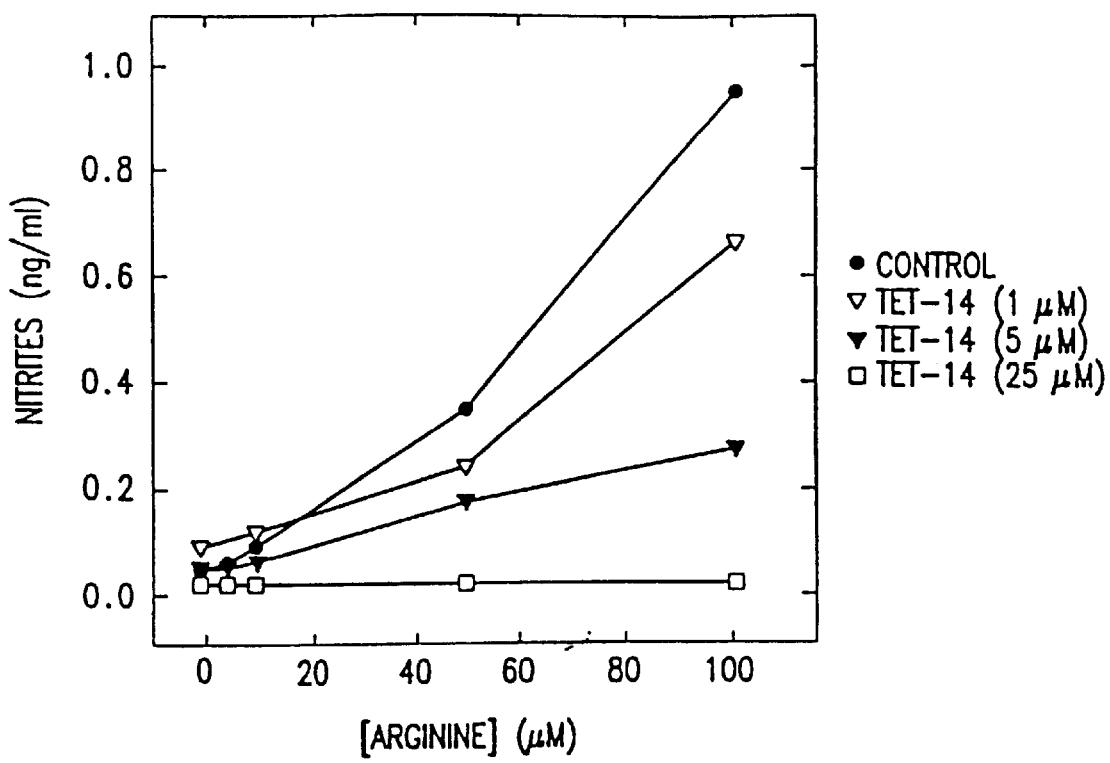

FIG. 13A. NO production: Control -•-; 1 μM No. 14-▽-; 5 μM No. 14-▼-; 25 μM No. 14 -□-.

Figure 13B:
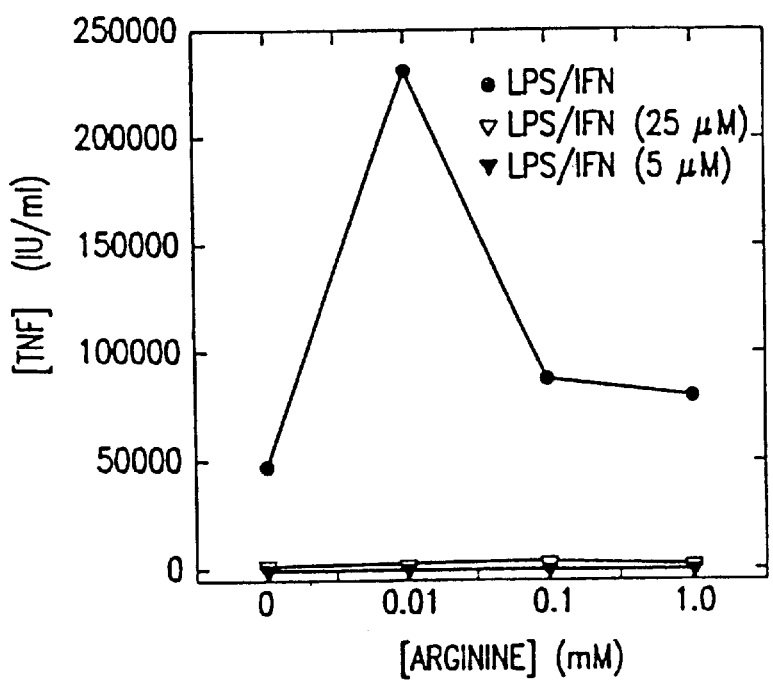

FIG. 13B. TNF production: Control -•-; 5 μM No. 14-▼-; 25 μM No. 14 -▽-;

FIG. 14. Effects of Compound No. 14 on the production of cytokines by LPS/γ-IFN-stimulated PBMC.

Figure 14A:
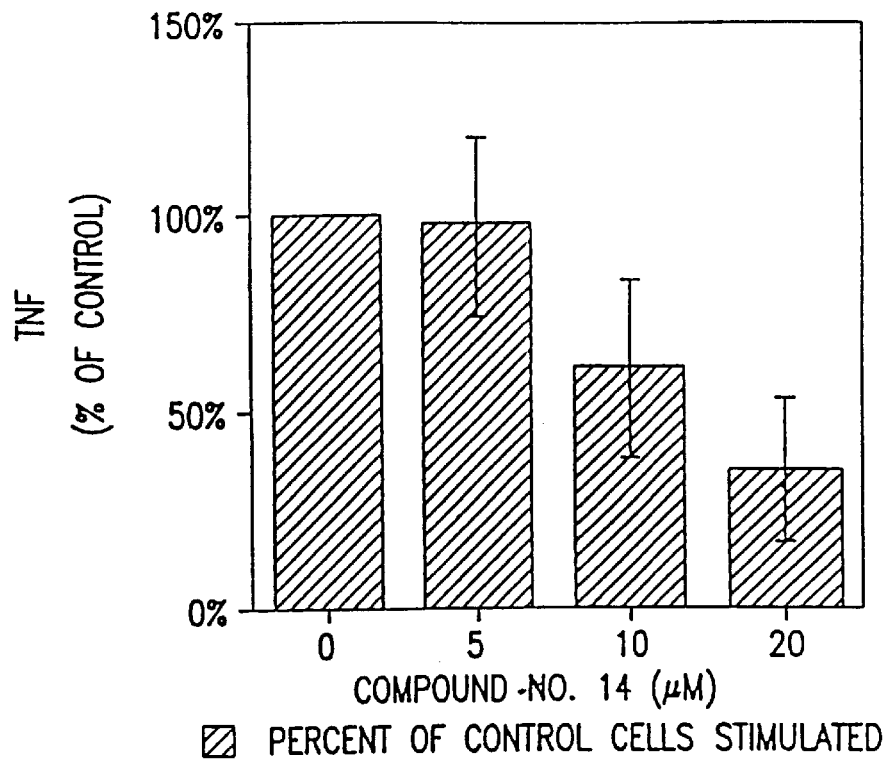
Figure 14B:
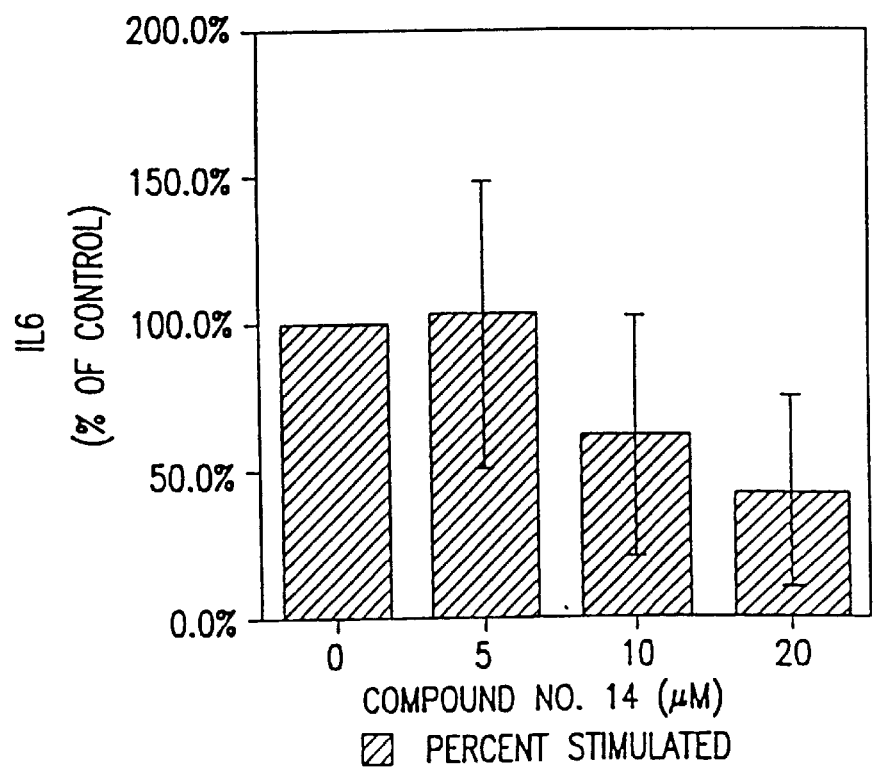
Figure 14C:
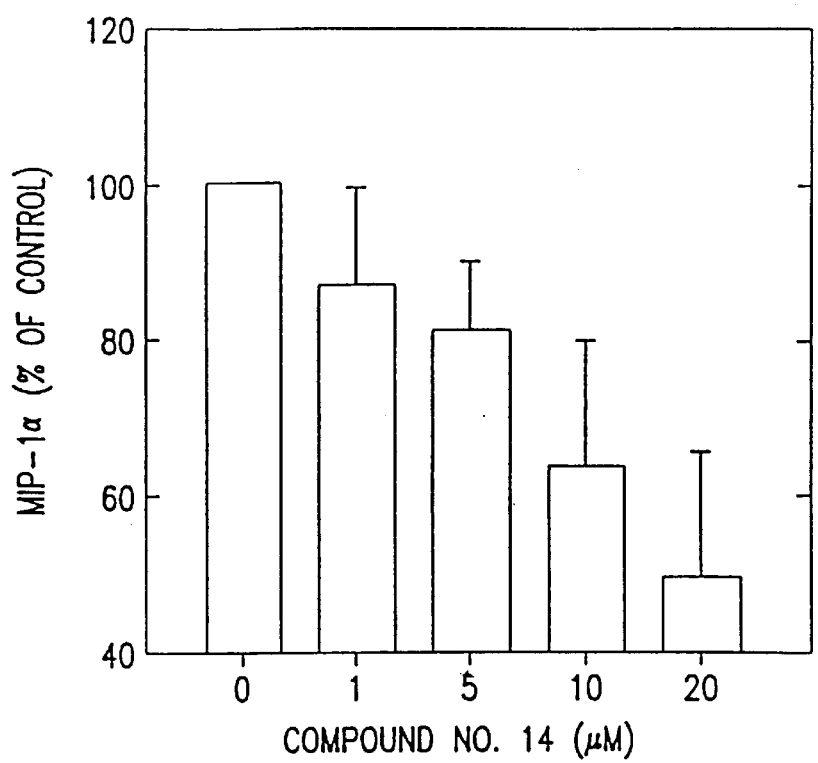

FIG. 14A. Tumor Necrosis Factor;

FIG. 14B. IL-6;

FIG. 14C. Macrophage Inflammatory Protein-1α

Figure 14D:
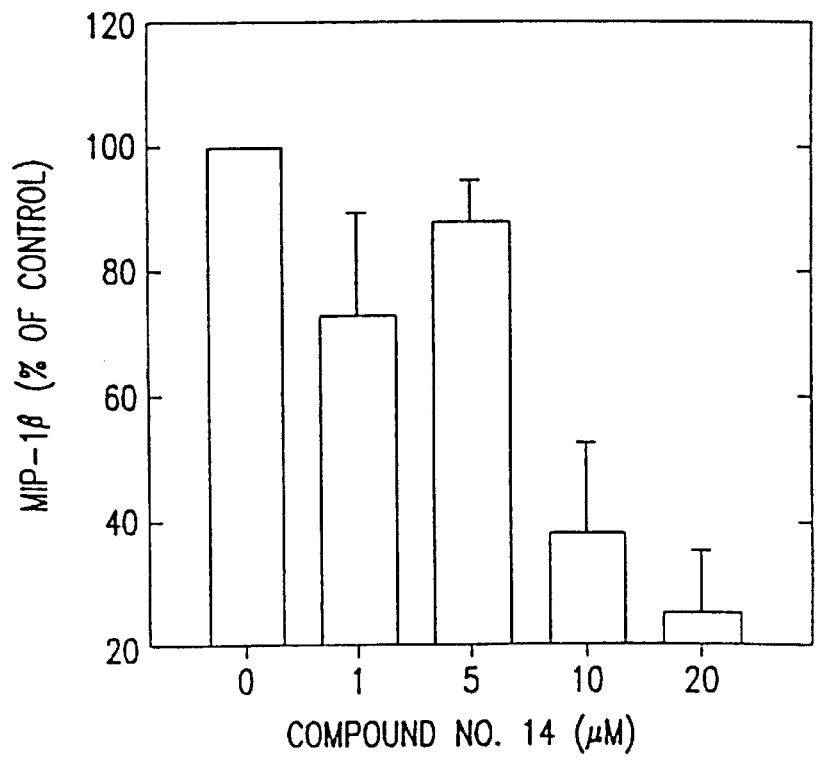

FIG. 14D. Macrophage Inflammatory Protein-1β.

Figure 15:
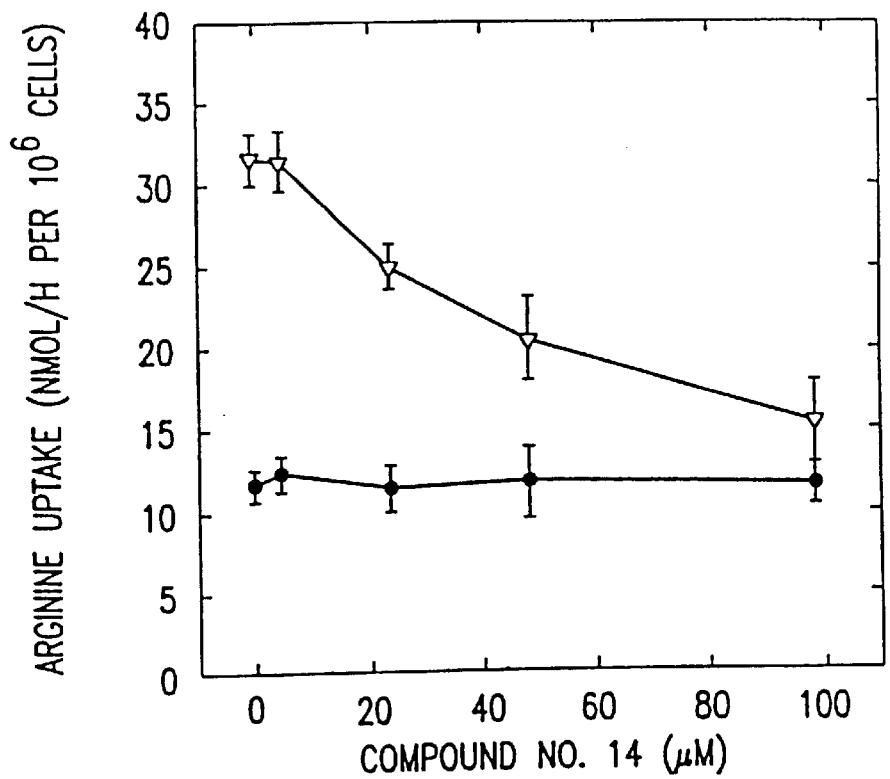

FIG. 15. Effects of Compound No. 14 on the transport of arginine in resting, -○-, and stimulated RAW 264.7 cells, -▽-.

Figure 16:
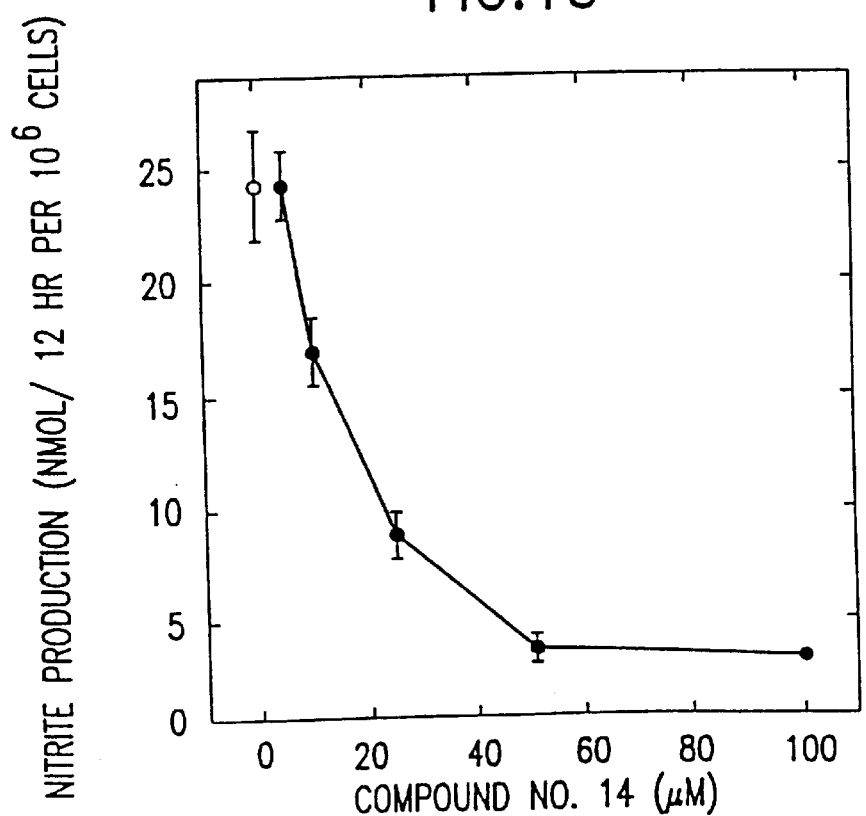

FIG. 16. Effects of Compound No. 14 on NO output of RAW 264.7 cells stimulated by γ-IFN/LPS for 8 hours and exposed to Compound No. 14 for further 4 hours.

Figure 17:
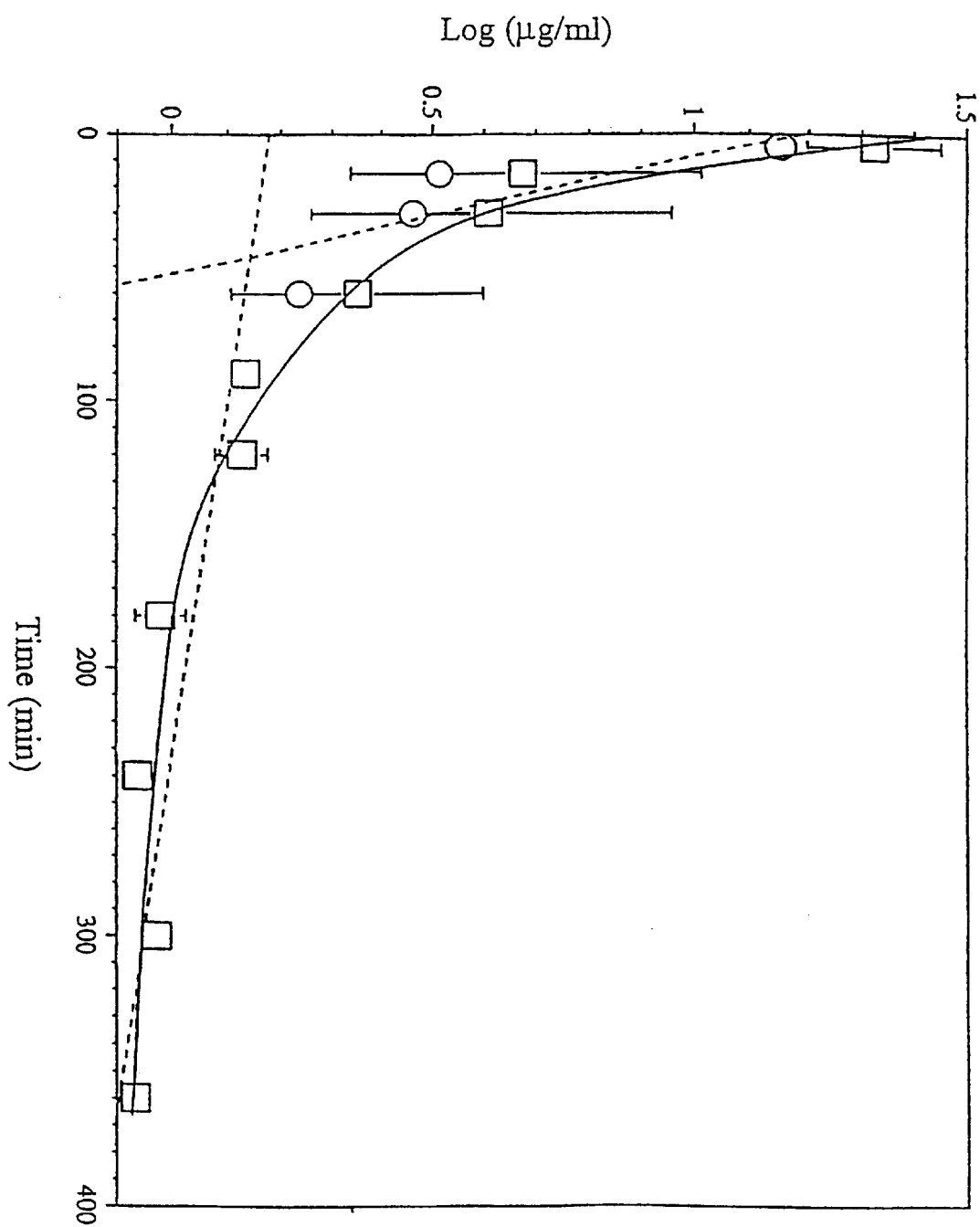

FIG. 17. The plasma concentrations of Compound No. 14 in rats following a single intravenous injection. The graph represents the time course of Compound No. 14's disappearance from the blood (solid line), and the extrapolated distribution and elimination phases (dashed lines), as determined by the method of residuals. Each square point represents the average±standard deviation for three rats, and each circular point the corresponding calculated distribution phase residual point.

5. DETAILED DESCRIPTION OF THE INVENTION

The present invention relates to methods and compounds for treating cachexia by inhibiting the production of urea, more particularly the production of urea by macrophages. The method of the invention may also be used to limit or prevent the damage induced by NO-mediated responses associated with stroke, shock, inflammation and other NO-related conditions. To this end, the present invention relates to the inhibition of macrophage production of urea and NO, and more particularly, inhibition of induced excessive production of urea and the inhibition of the transport processes which mediate arginine uptake by macrophages. The invention further includes the inhibition of the deleterious secretion of cytokines, e.g. Tumor Necrosis Factor (TNF). An alternate embodiment of the invention relates to the inhibition of arginine uptake in the treatment of tumors or infections, where the tumor cells or the infectious agent requires arginine.

The class of compounds useful for the invention includes aromatics substituted with multiple guanylhydrazone moieties, more properly termed amidinohydrazones. The synthesis and use of such compounds is described. The invention further encompasses screening assays to test additional compounds for such activity and pharmaceutical compositions useful in the practice of this method of therapy.

Historically, our initial studies were directed to the discovery of an hypothesized macrophage-produced soluble mediator which caused cultured hepatocytes to produce more urea. More particularly, we undertook to find a mediator produced by stimulated or activated macrophages such as are present in many chronic disease states associated with cachexia. Control studies performed during the initial attempts to isolate a cytokine which caused increased hepatocyte urea production in vitro led to the serendipitous discovery that the activated macrophages themselves produce urea in substantial amounts. That this was relevant to in vivo conditions was confirmed by experiments demonstrating enhanced urea production by macrophages isolated from mice made cachectic by a transplanted tumor (FIG. 2). These studies were further confirmed by the demonstration that the murine macrophage line RAW 264.7 responds to the macrophage activators LPS and γIFN with increased urea production which depends on the extracellular availability of arginine (FIGS. 3–5). These studies led to the assay for pharmacologic activity, which is described in detail herein below. The compounds used in the instant invention were identified based on this assay and used in animal model systems which demonstrate the efficacy of the invention (Sections 10, 11, 12, 13, 15 and 16, infra).

The foregoing results indicate that the secretion of cytokines by activated macrophages is but one aspect of the cachectic process. We developed the following model and hypothesis which is presented for explanatory purposes only and without limitation of the invention to any particular mechanism or scientific model. Equally important, in this model, are the direct metabolic processes of activated macrophages. The data indicate that in cachexia, activated macrophages make and secrete urea abundantly. The magnitude of the nitrogen loss which can be directly attributed to macrophages can be estimated from experimental culture data. Such studies show a single activated macrophage produces about 50 pg of urea/day. If one estimates that the fraction of activated macrophages is about 10% of the whole body immune cell population in a human being, then there is a total of about $10^{11}$ activated macrophages. This population could correspondingly account for the loss of about 5 grams of nitrogen per day which translates roughly to 30 grams of protein per day. This magnitude of loss represents a significant fraction of the weight loss that is observed clinically over time in chronic cachexia.

In accordance with the invention, inhibition of urea production, particularly that induced in macrophages, will reverse the process. Macrophage cellular metabolism differs from hepatic metabolism regarding the enzymes available to complete the so-called "urea cycle." In both tissues the ultimate step in urea production is a hydrolytic cleavage by the enzyme arginase of the amidino moiety of arginine to yield ornithine and urea (FIG. 1). One salient difference between macrophage and hepatic urea production is that macrophages lack substantial quantities of the enzyme ornithine transcarbamoylase and hence they cannot efficiently salvage the ornithine produced by arginase nor can they directly use ammonium ($NH_4$) to form urea but rather must rely on an exogenous supply of arginine. Secondly, it appears that there are two arginase enzymes, both of which catalyze the hydrolytic release of urea, one found especially in macrophages and a second found typically in hepatocytes of the liver.

These differences between macrophage and hepatic urea production have two implications: first, macrophages will selectively deplete arginine from the plasma. This circulating arginine must ultimately be replaced by protein breakdown in other tissues because the conversion of nitrogen to urea is essentially irreversible, i.e., urea cannot be further metabolized for re-use. Arginine itself is synthesized from α-keto glutarate and ammonium by glutamate synthetase, glutamine synthetase and carbamoyl phosphate synthetase. Secondly, given that macrophage urea production depends upon arginine uptake while hepatic urea synthesis does not, it may be possible to selectively block the cachexia-associated nitrogen loss while leaving corresponding hepatic functions relatively undisturbed.

In addition it may be advantageous to specifically block the macrophage form of the arginase enzyme and not the liver form. In vitro assays are described herein to detect the degree to which test compounds specifically inhibit each of these metabolic processes. These assays use the macrophage cell line RAW 264.7. Twenty compounds, including 15 novel compounds were tested for inhibition of macrophage urea production in an RAW 264.7 cell line assay. Six of the compounds display an $IC_{50}$ of about 10 μM or less and a further five compounds have been noted with an $IC_{50}$ of greater than 10 μM but less than about 100 μM (see Section 7.2).

Alternative embodiments of the present invention encompass any known means to inhibit macrophage urea production. Such methods may include but are not limited to the use of recombinant DNA methodologies. For example, a vector expressing an antisense message complementary to the mRNA of the macrophage form of arginase will be introduced into the macrophages of the cachectic host. Alternatively, a ribozyme specific for the mRNA of the macrophage form of arginase could be employed. Specific introduction into macrophages of vectors appropriate to either will be obtained by use of liposome carriers.

Another embodiment of the present invention involves inhibiting nitric oxide (NO) production and particularly of the enzyme NO-synthase. NO is produced by activated macrophages and vascular endothelial cells among other cellular sources. NO has been implicated as a causative pathological factor in a variety of inflammatory conditions: particularly in circumstances of shock and of ischemic necrosis (infarction) of the myocardium and of the central nervous system. NO-synthase catalyzes the oxidation of arginine to citrulline with an accompanying release of NO. Compounds which inhibit arginine uptake will therefore be effective suppressors of NO-synthase activity at the cellular level. Further, compounds of the above noted classes may be specific inhibitors of NO-synthase at the molecular level. The data shown herein demonstrate that the compounds used in accordance with the invention inhibit NO-production without inhibiting EDRF activity.

In a still further embodiment, the invention may be used to treat toxic shock, also known as systemic inflammatory response syndrome (SIRS). The data described herein shows that the compounds of the invention act by two independent pathways to prevent the mortality and morbidity associated with SIRS: (a) by preventing arginine uptake and, thereby, blocking the synthesis of NO by activated macrophages; and (b) by blocking the secretion of cytokines such as Tumor Necrosis Factor (TNF).

In yet another embodiment of the invention, inhibition of arginine uptake may be used to treat tumors or infections in which the tumor cells or infectious agent requires arginine. For example, tumors with arginine requirements include but are not limited to tumors of the breast, liver, lung and brain; whereas infectious agents with arginine requirements include but are not limited to *Pneumocystis carinii, Trypanosoma brucei, T. congolense* and *T. evansi*.

Examples of inhibitors which could be used in accordance with the invention include, but are not limited to, analogs of arginine; more particularly to a class of arylene compounds substituted with [(aminoiminomethyl)hydrazono]methyl moieties and [2-(aminoiminomethyl)hydrazono]ethyl moieties (hereinafter collectively "guanylhydrazones"); most preferably diphenyl compounds having 2, 3 or 4 guanylhydrazone moieties. These inhibitory compounds have one or more non-hydrolyzable analogs of the guanidino group of arginine.

Of guanylhydrazone compounds examined for activity in the present invention, compounds having only a single guanylhydrazone moiety were either inactive or required mM concentrations to achieve a 50% reduction in urea output. Benzyl and diphenyl compounds having 2, 3 or 4 guanylhydrazone moieties were active in some cases at less than 10 μM. In all cases tested the highly active compounds inhibited not only urea production but also inhibited the transport of arginine into the cell. A preferred embodiment of the present invention are di, tri and tetra guanylhydrazone substituted phenyl compounds having two phenyl nuclei linked by an alkanediamide or two phenoxy nuclei linked by an alkane. A second preferred embodiment are triacetylphenyl or triformylphenyl tris(guanylhydrazones). Examples of such useful compounds which were known include monoarylene bisguanylhydrazone, e.g., 1,3-diacetylpyridine bis(guanylhydrazone) (2), Ulrich, 1982, a monoarylene tris (guanylhydrazone), e.g., 1,3,5-triacetylbenzene tris (guanylhydrazone) (1), Ulrich, 1984, and a bisarylene bis (guanylhydrazone), e.g., 4,4'-diacetyldiphenylurea bis (guanylhydrazone) (8), Korytnyk, W. et al., J. Medicinal Chemistry 21:507–13, 1978. These compounds inhibit macrophage urea production in vitro at concentrations of between about 10 μM and about 50 μM. Further novel compounds of the present invention have inhibitory activity at five-fold lower concentrations. Such compounds include a bisarylene tris(guanylhydrazone), e.g., 3,5,4'-triacetyldiphenylurea tris(guanylhydrazone) (FIG. 17.9), a bisarylene tetrakis (guanylhydrazone), e.g., N,N'-bis(3,5-diacetylphenyl)decanediamide tetrakis (guanylhydrazone) (FIG. 17.14) and 3,3'-(ethylenedioxy)dibenzaldehyde bis (guanylhydrazone) (FIG. 17.16).

Further contemplated within the scope of the invention are tris arylene guanylhydrazono compounds in which each arylene group bears 1 or 2 guanylhydrazonoalkyl substituents. Such compounds may be synthesized using the methods taught herein.

5.1. Assays for Identifying Active Compounds

The following assays can be used to identify compounds that are used in the invention. Moreover, the assays can be utilized to determine the $IC_{50}$ (i.e., the concentration which achieves a half-maximal inhibition of the parameter assayed) for each compound tested. When used in vivo, the dose of each compound should be formulated to achieve a range of circulating concentrations that include the $IC_{50}$ measured in vitro.

The assays are exemplary and not intended to limit the scope of the method of the invention. Those of skill in the art will appreciate that modifications can be made to the assay system to develop equivalent assays that obtain the same result. In the working examples described herein, the RAW 264.7 cell line was used. However, the invention is not limited to the RAW 264.7 cell line which could be replaced by any macrophage cell line or by activated non-transformed macrophages in a primary culture.

5.1.1. Whole Cell Assay for Urea and Nitric Oxide Production

In general, the whole cell assay for urea production may be conducted as follows: macrophages or endothelial cells are activated (e.g., using factors including but not limited to γIFN and LPS as described in the examples, infra) in the presence of test inhibitors. After an appropriate time in culture, e.g., approximately overnight up to 2 days, the culture supernatant is analyzed for the presence of urea and nitric oxide. The production of urea and nitric oxide by any cell line can be measured by the same calorimetric assays used in clinical laboratories to determine the serum concentrations of these same compounds. The effects of various concentrations of inhibitor can be determined by comparison with the supernatant of control cultures which were not treated with the test inhibitor. A further control to indentify toxicity at any inhibitory dose may be included. An assay for the release of the intracellular enzyme lactate dehydrogenase, as used in the examples described infra, or an equivalent control, may be employed to such ends.

5.1.2. Whole Cell Assay for Arginine Uptake

Inhibition of arginine transmembrane concentrating activity by the compounds of the present invention is measured using carrier-free radiolabelled arginine. To this end, the cells are cultured to allow them to adhere (e.g., for 2 hours to overnight) and activated (e.g., using factors including but not limited to γIFN and LPS as described in the working examples infra) in the presence of the test inhibitor. After an appropriate incubation time, carrier-free labeled arginine is added to the culture. After a short time period (e.g., 5 minutes) the cells are washed with a solution containing unlabeled arginine to displace any radiolabeled arginine non- specifically bound to the cells in culture. The cells are then lysed and the cell lysates analyzed for the presence of radiolabeled arginine. The effects of the test compounds are determined by comparison of incorporation of radiolabel into treated cells versus the control cell cultures which were not treated with the potential inhibitor.

In the embodiment described in the working example herein, a test population of cells was cultured for about 3 hours so that the cells became firmly adherent. Various concentrations of the potential inhibitors were then added to parallel cultures. One hour later the macrophage stimulators, e.g. including, but not limited to LPS and γIFN, were added. Eighteen hours later the cells were washed in a warm balanced salt solution supplemented with glucose. Carrier-free radiolabelled arginine was added; after 5 minutes, active uptake of arginine was stopped by washing the cell three times with buffer, chilled to 0° C., containing 10 mM unlabeled arginine to displace any externally bound label. The contents of the washed cells are solubilized in 100 μl of formic acid and counted by standard techniques.

5.1.3. Cell Lysate Assay for Arginase Activity

The cell lysate assay for arginase activity involves exposing a cell lysate to an arginase activation buffer in the presence of the test compound. After an appropriate incubation period, arginine is added and the enzyme activity of arginase is determined e.g., by measuring the urea concentration in the sample. Inhibitory activity of the test compound is determined by comparing the results obtained to control samples which were not exposed to the test compound. As demonstrated in the working examples, infra, direct inhibition of arginase is determined by first preparing a low speed supernatant of a cell lysate at a protein concentration of between 0.5 and 4 mg/ml. The supernatant is mixed in a 1:4 ratio with an activation buffer containing $MnCl_2$ and albumin and aliquots are incubated with various concentrations of the potential inhibitory compound. After a 20 minute period of heat activation at 55° C., the solution is made to 0.25 M arginine, then incubated at 37° C. for 20 minutes. TCA is added to remove protein by centrifigation, then the urea concentration of the supernatant determined by colorimetric assay based on diacetylmonoxime.

5.2. Active Compounds

By use of the above-noted in vitro bio-assays, compounds have been identified which are inhibitors of urea and nitric oxide production and of arginine uptake. The results of these experiments are summarized in Section 7.2. Of the twenty (20) compounds examined six (6) are effective inhibitors at concentrations between 1 and 10 μM: Compounds Nos. 1, 9, 13, 14, 15, 16. A further six (6) compounds were effective at concentrations of between 10 and 100 μM: Compounds No. 2, 8, 11, 18, and 19. The compound which was identified as the most active (Compound No. 14) was used in vivo in animal models of cachexia, NO-mediated inflammation, endotoxin-induced shock, cerebral infarction and neoplasia. In each of these models Compound No. 14 proved to be effective (Sections 10, 11, 13, and 16 infra.)

5.2.1. Compounds and Their Synthesis

Hereinafter GhyCH-=$NH_2$(CNH)—NH—N=CH— and $GhyCCH_3$—=$NH_2$(CNH)—NH—N=$CCH_3$—. The compounds of the invention include the following two major genera. The first consists of compounds having the formula:

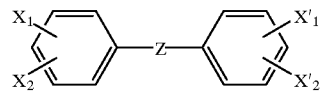

wherein
$X_2$=GhyCH—, $GhyCCH_3$— or H—;
$X_1$, $X'_1$ and $X'_2$ independently=GhyCH— or $GhyCCH_3$—;
Z=—NH(CO)NH—, or —A—$(CH_2)_n$—A—, n=2–10, which is unsubstituted, mono— or di-C-methyl substituted, or a mono or di-unsaturated derivative thereof; and A, independently,=—NH(CO)—, —NH(CO)NH—, —NH— or —O— and salts thereof. For ease of synthesis, a preferred embodiment includes those compounds wherein A is a single functionality. Also included within the invention are compounds having the same formula wherein $X_1$ and $X_2$=H; $X'_1$ and $X'_2$ independently=GhyCH— or GhyCCH$_3$—; Z=—A—(CH$_2$)$_n$—A—, n=3–8; and A=—NH(CO)— or —NH(CO)NH—, and salts thereof. Also included are compounds wherein $X_1$ and $X_2$=H; $X'_1$ and $X'_2$ independently=GhyCH— or GhyCCH$_3$— and Z=—O—(CH$_2$)$_2$—O—.

Further examples of genera of the invention include: The genus wherein: $X_2$=GhyCH—, GhyCCH$_3$— or H—; $X_1$, $X'_1$ and $X'_2$=GhyCH— or GhyCCH$_3$—; and Z=—O—(CH$_2$)$_n$—O—, n=2–10 and salts thereof; and the related genus wherein, when $X_2$ is other than H, $X_2$ is meta or para to $X_1$ and wherein $X'_2$ is meta or para to $X'_1$. A compound having the above formula wherein: $X_2$=GhyCH, GhyCCH$_3$ or H; $X_1$, $X'_1$ and $X'_2$,=GhyCH—or GhyCCH$_3$—; and Z=—NH—(C=O)—NH— and salts thereof; and the related genus wrhein, when $X_2$ is other than H, $X_2$ is meta or para to $X_1$ and wherein $X'_2$ is meta or para to $X'_1$.

Also included are compounds having the formula:

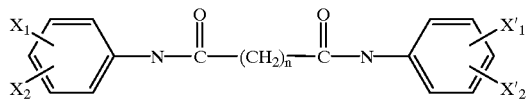

wherein: n=3–8; $X_2$ and $X'_2$=GhyCH—, GhyCCH$_3$— or H—; $X_1$ and $X'_1$=GhyCH— or GhyCCH$_3$—; and salts thereof; and the related genus wherein, when $X_2$ or $X'_2$ or both are other than H, then $X_2$ or $X'_2$ are meta or para to $X_1$ or $X'_1$, respectively. Also included are compounds having the formula:

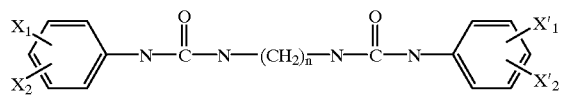

wherein: $X_2$ and $X'_2$=GhyCH—, GhyCCH$_3$— or H—; $X_1$ and $X'_1$=GhyCH— or GhyCCH$_3$—; and n=2–10 and salts thereof and the related genus wherein, when $X_2$ or $X'_2$ or both are other than H, then $X_2$ or $X'_2$ are meta or para to $X_1$ or $X'_1$, respectively.

The second major genus consists of compounds of the formula:

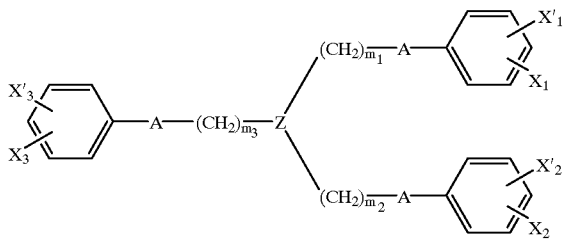

wherein, $X_1$, $X_2$ and $X_3$, independently=GhyCH— or GhyCCH$_3$—; $X'_1$, $X'_2$ and $X'_3$, independently=H. GhyCH— or GhyCCH$_3$—; Z=(C$_6$H$_3$), when $m_1$, $m_2$, $m_3$=0 or Z=N, when, independently, $m_1$, $m_2$, $m_3$=2–6; and A=—NH(CO)—, —NH(CO)NH—, —NH— or —O— and salts thereof. Further examples of genera of the invention include the genus wherein when any of $X'_1$, $X'_2$ and $X'_3$ are other than H, then the corresponding substituent of the group consisting of $X_1$, $X_2$ and $X_3$ is meta or para to $X'_1$, $X'_2$ and $X'_3$, respectively; the genus wherein, $m_1$, $m_2$, $m_3$=0 and A=—NH(CO)—; and the genus wherein ml, $m_2$, $m_3$=2–6 and A=—NH(CO)NH—.

The compounds of the present invention can be synthesized by means of two fundamental reactions. Those skilled in the art will recognize that numerous variants may be synthesized by means of these reactions and that these variants have properties in common with the compounds herein disclosed.

Reaction 1 consists of the reaction of a substituted aromatic having a primary or secondary amine, e.g., 3,5-diacetylaniline, and a dioyl dichloride, e.g., glutaryl dichloride, to yield the corresponding N,N'-diphenylalkanediamide. "Reversed" diamides can also be prepared. Acetyl and diacetylbenzoic acid can be prepared by the reaction of the corresponding substituted toluenes and KMnO$_4$. The acids may be then activated bystandard techniques and reacted with the appropriate α,ω-alkanediamines to yield the reverse "diamides". Mixed forward and reversed diamides can be synthesized by methods well known in the field of peptide synthesis. Thus, an N-t-butyloxycarbonyl amino acid may be reacted with a substituted aniline, followed by deprotection and reaction of the amino group with an acitiviated substituted benzoic acid. When used herein the symbol "—NH(CO)—", unless otherwise indicated, includes the —(CO)NH— isomer.

The method is not limited to dioyl dichlorides. The trichloride derivatives of trioyl compounds may be used to synthesize t-riphenyl alkanetriamides in a similar fashion. Suitable triacids include cyclic acids, e.g., 1,3,5-cyclohexanetricarboxylic acid (Aldrich Chem. Co.), 1,3,5-trimethyl,1,3,5-cyclohexanetricarboxylic acid (Kemp's triacid, Kemp and Petrakis, 1981, J.Org.Chem 46:5140), 1,3,5-benzinetricarboxylic acid (Aldrich Chem. Co.) and linear tricarboxylic acids such as 1,2,3-propanetricarboxylic acid (Sigma Chem. Co.). The identical reaction may be performed wherein the dioyl chloride is replaced by trichloromethyl chloroformate to yield a diphenylurea condensation product. An alternative to Reaction 1 can be performed to yield a 1,n-(n-alkanedioxy) diarylene by reacting the 1,n-dibromoalkane, e.g., 1,2 dibromoethane and a monohydroxylarylene, e.g., 3-hydroxyacetophenone.

Further embodiments of the invention include the use of triamines of the form H$_2$N—(CH$_2$)$_n$—NH—(CH$_2$)$_q$—NH$_2$ wherein (n,q=2–6) and of the form Y—((CH$_2$)$_n$—NH$_2$)$_3$ wherein Y may be one of N (n=2–6), C(NO$_2$) (n=3), a C-alkane (n=1), 1,3,5-adamantanetriyl (n=3) or 1,3,5-benzinetriyl (n=1–3).

In two further embodiments of the invention, an acetyl- or diacetylaryl isocyanate is reacted with an alkanediamine or, alternatively, an acetyl— or diacetylaryl amine is reacted with an alkanediyl diisocyanate to yield bis-ureido intermediates which may be reacted with aminoguanidine to form the guanylhdrazono end products. The requisite isocyanates are either commercially available or may be synthesized from from the corresponding amines by reaction with phosgene, trichloromethyl chloroformate, or bis(trichloromethyl) carbonate in toluene or xylene at elevated temperature.

Reaction 2 consists of the reaction of an acetophenone or benzaldehyde type moiety and an aminoguanidine to yield the condensation product wherein an imino-bonded (N=C) aminoguanidine replaces the ketone or carbonyl moiety of the arylene thus forming a guanylhydrazone and accompanied by the release of a water molecule.

5.2.2. Pharmaceutical Formulations

Because of their pharmacological properties, the compounds of the present invention can be used especially as agents to treat patients suffering from cachexia, deleterious NO-mediated responses, infarction, tumors or infections that require arginine. Such a compound can be administered to a patient either by itself, or in pharmaceutical compositions where it is mixed with suitable carriers or excipient(s).

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

5.3. Uses of the Compounds

For any compound used in the method of the invention, the appropriate dose is one which achieves a circulating range of concentrations which encompass the ICSO determined to be effective for that compound as reported herein in Tables I, II and III or determined in the manner herein described. For example, when using Compound Nos. 1, 9, 13 or 15, for treating cachexia, inflammation, endotoxic shock or septic shock, infarction or neoplasm regardless of the formulation chosen, the amount administered should be sufficient to achieve a serum concentration or a circulating plasma concentration of between about 5 $\mu$M and 100 $\mu$M. When using Compound No. 14, for treating cachexia, inflammation, endotoxic shock or septic shock, infarction or neoplasm regardless of the formulation chosen, the amount administered should be sufficient to achieve a serum concentration or a circulating plasma concentration of between about 0.5 $\mu$M and 10 $\mu$M. As shown in the working examples, a daily parenteral dose of Compound No. 14 of about 0.4 mg/Kg, used to treat cachexia, and a single parenteral dose of 1.0 mg/Kg, to treat LPS-induced toxicity, are effective in murine models.

Based on the pharmacokinetic constants reported in Section 18, below, and the time v. concentration curve of FIG. 17, it is apparent that while single doses of between 0.4–1.0 mg/kg do not achieve sustained plasma levels of Compound No. 14 in excess of 0.5 $\mu$M, doses in this range do achieve peak plasma levels in excess of about 0.5 $\mu$M. Indeed, from the data presented here, it appears that daily exposures of a subject to the indicated levels for periods of 10–20 minutes or a single exposure of about an hour's duration results in a therapeutically significant effect.

Those skilled in the art will appreciate that the dose appropriate to a given route of administration can be determined by the application pharmacological methods that are well known to those skilled in the art.

When the compounds of the present invention are used to treat chronic inflammation a dose regime should be determined by application of standard pharmacologic techniques using the above-noted dose ranges as initial points. To treat acute inflammatory conditions, a single larger dose may be administered in an alternative embodiment. As shown in the working examples, a single parenteral dose of 5.0 mg/Kg of Compound No. 14 was found effective to treat such an acute event.

6. EXAMPLE

Synthesis of the Active Compounds

This section describes in detail the synthesis and purification of useful intermediates and of exemplary compounds of the present invention.

6.1. Synthesis of Intermediate Products

In the following it is understood that amidinohydrazone and guanylhydrazone and (aminoiminomethyl)hydrazono are synonyms.

The following reactions are used to link substituted arylene compounds by means of alkane chains of various lengths. The bond may be an amide, a phenoxyalkane or a urea.

6.1.1. N,N'-Bis(3,5-Diacetylphenyl)-Pentanediamide 3,5-Diacetylaniline (531 mg) in dichloromethane (7 mL) containing pyridine (0.4 mL) was treated with 0.141 mL glutaryl dichloride. After 1 hr, filtration and washing with water gave 555 mg of N,N'-bis(3,5-diacetylphenyl) pentanediamide, mp 246–7° C.

Analogously, the following were prepared from 3,5-diacetylaniline and the corresponding dioyl dichlorides:
N,N'-bis(3,5-diacetylphenyl)butanediamide, mp 293–6° C.;
N,N'-bis(3,5-diacetylphenyl)hexanediamide, mp 269–70° C.;
N,N'-bis(3,5-diacetylphenyl)heptanediamide, mp 200–3° C.;
N,N'-bis(3,5-diacetylphenyl)octanediamide, mp 183–4° C.;
N,N'-bis(3,5-diacetylphenyl)nonanediamide, mp 179–80° C.;
N,N'-bis(3,5-diacetylphenyl)decanediamide, mp 196–9° C.;
N,N'-bis(3,5-diacetylphenyl)dodecanediamide, mp 178–9° C.;
N,N'-bis(3,5-diacetylphenyl)(isophthalic acid diamide), mp 283–4° C. Also analogously, N,N'-bis(3-acetylphenyl) pentanediamide, mp 174–5° C. was prepared from 3-aminoacetophenone and glutaryl dichloride.

6.1.2. N-(4-Acetylphenyl)-N'-(3.5-Diacetylphenyl) Urea

4-Aminoacetophenone (1.35 g) in toluene (20 mL) was treated with trichloromethyl chloroformate (1.2 mL). The mixture was heated at reflux for 2 hr. 3,5-diacetylaniline (1.77 g) was added and the mixture was heated at reflux for 1 hr then allowed to stand 16 hr at room temp. The product was filtered off and washed with ethanol and dried to give 0.93 g of N-(4-acetylphenyl)-N'-(3,5-diacetylphenyl)urea, mp 251–2° C.

6.1.3. 1,2-Bis(3-Acetylphenoxy)Ethane

3-Hydroxyacetophenone (8.4 g) and 1,2-dibromoethane (5.07 g) were treated with potassium hydroxide (3.83 g) and heated under nitrogen at reflux for 2 days. The mixture was cooled and water (200 mL) was added and the mixture stirred for 1 hr. The precipitate was filtered out and recrystallized from isopropanol to give 1.21 g of 1,2-bis(3-acetylphenoxy)ethane, mp 120–1° C.

6.1.4. 1,5-Bis[([(3,5-Diacetylphenyl)-Amino]Carbony)Lamino]-2-Methylpentane 1,5-Diisocyanato-2-methylpentane (0.18 ml) was added to a suspension of 3,5-diacetylaniline (0.531 g) in dichloromethane (7 ml) containing catalytic 4-dimethylaminopyridine (10 mg). The mixture was refluxed for 2 hr and allowed to stand overnight. Filtration gave while crystals, 0.30 g, mp 124–130° C.

6.1.5. Tris[2-([(3-Acetylphenyl)Amino]-Carbonylamino)Ethyl]amine

3-Acetylphenyl isocyanatate (0.60 g) in dichloromethane (10 mL) was reacted with tris(2-aminoethyl)amine (0.146 g). A vigorous reaction occurred and a copious white turbidity resulted. Methanol was added and the mixture was re-concentrated to produce crystalline material which was filtered out. Yield 0.61 g, mp 193° C.

6.1.6. 3,5-Diacetylphenyl Isocyanate and N,N'-Bis(3.5-Diacetylphenyl)Urea 3,5-Diacetylaniline (3.0 g, 16.9 mmol) was suspended in toluene (50 mL) with stirring in an ice bath. A solution of bis(trichlormethyl) carbonate (1.67 g, 5.9 mmol) in toluene (10 mL) was added. The suspension was allowed to warm to room temp. and was stirred overnight at r.t. The mixture was then heated at reflux for 4 hr, cooled, and filtered to give 1.1 g of N,N'-bis(3,5-diacetylphenyl)urea, mp dec 137–8° C. (gas evol.). The filtrate was evaporated to give 2.2 g of 3,5-diacetylphenyl isocyanate as a white powder, mp 71° C.

6.2. Conversion of Intermediates to End Products

The following reactions are examples which illustrate a general condensation reaction wherein the primary amine of aminoguanidine displaces the oxygen of an acetophenone or benzaldehyde or ketone and elaborates an $H_2O$ and forms the guanylhydrazone. In general, all reactions are carried out at elevated temperature with acid catalysis in aqueous alcohol. The products are recovered by crystallization upon cooling and, optionally, the addition of petroleum ether or isopropanol. Purification was performed by recrystallization.

Compound 4, FIG. 7A.4: 4-([(aminoiminomethyl)hydrazono]methyl)cinnamic acid hydrochloride:

4-formylcinnamic acid (1.76 g) and aminoguanidine hydrochloride (1.22 g) were heated in 83% ethanol (24 mL) for 2 hr. Cooling and filtration gave 2.56 g of 4-([(aminoiminomethyl)hydrazono]methyl)cinnamic acid hydrochloride, mp 285–8° C.

Compound 6, FIG. 7A.6: 2-([(1H-imidazol-1-yl)-1,4-phenylene]ethylidyne)hydrazinecarboximidamide hydrochloride:

4-(1H-imidazol-1-yl)acetophenone (1.86 g) and aminoguanidine hydrochloride (1.22 g) were heated in 83% ethanol (12 mL) for 48 hr. Cooling and filtration gave 2.6 g of 2-([(1H-imidazol-1-yl)-1,4-phenylene]ethylidyne) hydrazinecarboximidamide hydrochloride, mp 275–6° C.

Compound 7, FIG. 7A.7: 2-[(3,4-dihydroxyphenyl)-ethylidyne]hydrazinecarboximidamide hydrochloride:

3,4-dihydroxyacetophenone (3.04 g) and aminoguanidine hydrochloride (2.44 g) were heated in 75% ethanol (16 mL) for 4 hr under nitrogen. Cooling and filtration gave 2.7 g of 2-[(3,4-dihydroxyphenyl)ethylidyne]-hydrazinecarboximidamide hydrochloride, mp 242–5° C.

Compound 9, FIG. 7B.9: N-(4-acetylphenyl)-N'-(3,5-diacetylphenyl)urea tris(amidinohydrazone) trihydrochloride:

N-(4-acetylphenyl)-N'-(3,5-diacetylphenyl)urea (0.676 g), aminoguanidine hydrochloride (0.83 g), and aminoguanidine dihydrochloride (0.01 g) were heated in 83% methanol (12 mL) for 18 hr. Cooling and filtration gave 0.85 g of N-(4-acetylphenyl)-N'-(3,5-diacetylphenyl)urea tris (amidinohydrazone) trihydrochloride, mp 247–253° C. dec.

Compound 10, FIG. 7B.10: 5-(1-[2-(aminoiminomethyl)hydrazono]ethyl)salicylic acid hydrochloride:

5-Acetylsalicylic acid (3.6 g) and aminoguanidine hydrochloride (2.4 g) were heated in 80% ethanol (25 mL) for 2 hr. Cooling and filtration gave 5.2 g of crude 5-(1-[2-

(aminoiminomethyl)hydrazono]ethyl) salicylic acid hydrochloride. Of this, 0.58 g was purified by dissolving in aq. NaOH (pH 12.5) and reprecipitation with aq HCl (to pH 2) to give 0.45 g of 5-(1-[2-(aminoiminomethyl)hydrazono]ethyl)-salicylic acid hydrochloride, mp 312–3° C. (dec).

Compound 12, FIG. 7B.12: N,N'-bis(3-acetylphenyl) pentanediamide bis(amidinohydrazone) dihydrochloride:

N,N'-bis(3-acetylphenyl)pentanediamide (3.66 g), aminoguanidine hydrochloride (2.75 g), and aminoguanidine dihydrochloride (0.05 g) were heated in methanol (35 mL) for 18 hr. Cooling and filtration gave 5.412 g of N,N'-bis(3-acetylphenyl)pentanediamide bis(amidinohydrazone) dihydrochloride, mp 187–191° C.

Compound 13, FIG. 7B.13: N,N'-bis(3,5-diacetylphenyl) pentanediamide tetrakis(amidinohydrazone) tetrahydrochloride:

N,N'-bis(3,5-diacetylphenyl)pentanediamide (0.45 g), aminoguanidine hydrochloride (0.55 g), and aminoguanidine dihydrochloride (0.01 g) were heated in 91% ethanol (4.4 mL) for 18 hr. Cooling and filtration gave 0.794 g of N,N'-bis(3,5-diacetylphenyl)pentanediamide tetrakis (amidinohydrazone) tetrahydrochloride, mp 299–301° C. dec.

Compound 14, FIG. 7C.14: N,N'-bis(3,5-diacetylphenyl) decanediamide tetrakis(amidinohydrazone) tetrahydrochloride:

N,N'-bis(3,5-diacetylphenyl)decanediamide (0.65 g), aminoguanidine hydrochloride (0.691 g), and aminoguanidine dihydrochloride (0.01 g) were heated in 91% ethanol (5.5 mL) for 18 hr. Cooling and filtration gave 0.87 g of N,N'-bis(3,5-diacetylphenyl)decanediamide tetrakis (amidinohydrazone) tetrahydrochloride, mp 323–4° C. dec.

Compound 15, FIG. 7C.15: 2,2'-[1,2-ethanediylbis(oxy-3,1-phenyleneethylidyne)] bishydrazinecarboximidamide dihydrochloride:

1,2-bis(3-acetylphenoxy)ethane (0.894 g), aminoguanidine hydrochloride (0.83 g), and aminoguanidine dihydrochloride (0.01 g) were heated in aq. 96% methanol (6.25 mL) for 18 hr. Cooling and filtration gave 1.378 g of 2,2'-[1,2-ethanediylbis(oxy-3,1-phenyleneethylidyne)]bis (hydrazinecarboximidamide) dihydrochloride, mp 303–7° C.

Compound 16, FIG. 7C.16: 3,3'-(ethylenedioxy)-dibenzaldehyde bis(amidinohydrazone) dihydrochloride:

3,3'-(ethylenedioxy)dibenzaldehyde (1.08 g), aminoguanidine hydrochloride (1.105 g), and aminoguanidine dihydrochloride (0.005 g) were heated in 96% ethanol (6.25 mL) for 18 hr under nitrogen. Cooling and filtration gave 1.428 g of 3,3'-(ethylenedioxy)dibenzaldehyde bis (amidinohydrazone) dihydrochloride, mp 264–6° C.

Compound 17, FIG. 7C.17: 4,4'-(ethylenedioxy)di-m-anisaldehyde bis(amidinohydrazone) dihydrochloride:

4,4'-(ethylenedioxy)di-m-anisaldehyde (0.99 g), aminoguanidine hydrochloride (0.829 g), and aminoguanidine dihydrochloride (0.01 g) were heated in 95% methanol (10.5 mL) under nitrogen for 16 hr. Cooling and filtration gave 1.52 g of 4,4'-(ethylenedioxy)di-m-anisaldehyde bis (amidinohydrazone) dihydrochloride, mp 322–3° C. dec.

Compound 18, FIG. 7C.18: 3,3'-(trimethylenedioxy)di-p-anisaldehyde bis(amidinohydrazone) dihydrochloride:

3,3'-(trimethylenedioxy)di-p-anisaldehyde (1.032 g), aminoguanidine hydrochloride (0.829 g), and aminoguanidine dihydrochloride (0.02 g) were heated in 95% methanol (10.5 mL) for 16 hr. Cooling and filtration gave 1.372 g of 3,3'-(trimethylenedioxy)di-p-anisaldehyde bis (amidinohydrazone) dihydrochloride, mp 233–5° C.

Compound 19, FIG. 7C.19: 1,4-bis[2-(aminoiminomethyl)hydrazono]cyclohexane dihydrochloride:

1,4-cyclohexanedione (2.24 g), aminoguanidine bicarbonate (6.0 g), and concentrated hydrochloric acid (3.67 mL) were heated in water (50 mL) for 5 min. The solution was cooled and treated with isopropanol (50 mL). After crystallization was complete, filtration gave 2.91 g of 1,4-bis[2-(aminoiminomethyl)hydrazono]cyclohexane dihydrochloride, mp 260° C. dec.

Compound 20, FIG. 7C.20: 2,2'-(1,4-diphenyl-1,4-butanediylidene)bishydrazinecarboximidamide dihydrochloride:

1,2-dibenzoylethane (4.76 g), aminoguanidine bicarbonate (5.45 g), and concentrated hydrochloric acid (3.33 mL) were heated in 50% ethanol (60 mL) for 24 hr. Cooling, concentration and filtration gave 4.3 g of 2,2'-(1,4-diphenyl-1,4-butanediylidene)bis(hydrazinecarboximidamide) dihydrochloride, mp 285–6° C.

6.3. Further Exemplary Compounds

Compound 21, FIG. 7D.21: N,N'-bis(3,5-diacetylphenyl)-butanediamide tetrakis(amidinohydrazone) tetrahydrochloride:

N,N'-bis(3,5-diacetylphenyl)butanediamide (0.545 g), aminoguanidine hydrochloride (0.69 g), and aminoguanidine dihydrochloride (0.01 g) were heated in 91% ethanol (5.5 mL) for 18 hr. Cooling and filtration gave 0.97 g of N,N'-bis(3,5-diacetylphenyl)butanediamide tetrakis (amidinohydrazone) tetrahydrochloride, mp 314° C.

Compound 22, FIG. 7D.22: N,N'-bis(3,5-diacetylphenyl) hexanediamide tetrakis(amidinohydrazone) tetrahydrochloride: N,N'-bis(3,5-diacetylphenyl) hexanediamide (0.58 g), aminoguanidine hydrochloride (0.69 g), and aminoguanidine dihydrochloride (0.01 g) were heated in 91% 2-mothoxyethanol (5.5 mL) for 18 hr. Filtration while hot gave 0.936 g of N,N'-bis(3,5-diacetylphenyl)hexanediamide tetrakis(amidinohydrazone) tetrahydrochloride, mp (chars) 320–330° C.

Compound 23, FIG. 7D.23: N,N'-bis(3,5-diacetylphenyl)-heptanediamide tetrakis(amidinohydrazone) tetrahydrochloride:

N,N'-bis(3,5-diacetylphenyl)heptanediamide (0.478 g), aminoguanidine hydrochloride (0.553 g), and aminoguanidine dihydrochloride (0.01 g) were heated in 91% ethanol (4.4 mL) for 18 hr. Cooling and filtration gave 0.739 g of N,N'-bis(3,5-diacetylphenyl)heptanediamide tetrakis-(amidinohydrazone) tetrahydrochloride, mp 273–7° C.

Compound 24, FIG. 7D.24: N,N'-bis(3,5-diacetylphenyl) (isophthalic acid diamide) tetrakis(amidinohydrazone) tetrahydrochloride:

N,N'-bis(3,5-diacetylphenyl)(isophthalic acid diamide) (0.726 g) and aminoguanidine hydrochloride (0.829 g) were heated in 7:1 2-methoxyethanol/water (11.5 mL) for 18 hr. Cooling and filtration gave 0.54 g of N,N'-bis(3,5-diacetylphenyl)(isophthalic acid diamide) tetrakis (amidinohydrazone) tetrahydrochloride, (chars) mp 322–330° C.

Compound 25, FIG. 7E.25: 3,3'-(pentamethylenedioxy) di-p-anisaldehyde (0.748 g), aminoguanidine hydrochloride (0.553 g), and aminoguanidine dihydrochloride (0.01 g) were heated in methanol (5 mL) for 18 hr. Cooling and filtration gave 0.080 g of 3,3'-(pentamethylenedioxy)di-p-anisaldehyde bis(amidinohydrazone) dihydrochloride, mp 195–8° C.

Compound 26, FIG. 7E.26: A solution of 3,5-diacetylaniline (0.885 g) in tetrahydrofuran (10 mL) containing 0.45 mL pyridine was treated with 0.65 mL benzoyl chloride. The mixture was stirred 1 hr, then treated with I mL water and stirred 15 min. The mixture was then diluted with 40 mL water and stirred 30 min. Filtration and washing with water and isopropanol gave colorless needles of N-benzoyl-3,5-diacetylaniline, 1.36 g, mp 188–189° C. A suspension of N-benzoyl-3,5-diacetylaniline (0.844 g) in aq. 87.5% ethanol (8 mL) containing 0.73 g aminoguanidine hydrochloride and a trace of HCl was heated at reflux for 18 hr. Cooling and filtration gave 1.357 g of N-benzoyl-3,5-diacetylaniline bis(amidinohydrazone) dihydrochloride (Compound 26), mp 268–72° C.

Compound 27, FIG. 7E.27: A suspension of 3,5-diacetylaniline (0.531 g) in water (8 mL) was treated with cyanamide (0.143 g) and conc. HCl (0.25 mL) and heated at reflux. Additional 0.080 g portions of cyanamide were added at 2 hr and 4 hr. After 6 hr, the mixture was concentrated in vacuo until crystalline material separated, then filtered to give 0.110 g of off-white solid, mp 120–2° C. Of this, 0.104 g was treated with aminoguanidine hydrochloride (0.112 g) in 2.5 mL of aq. 80% ethanol containing aminoguanidine dihydrochloride (0.01 g). After 18 hr at reflux, colling and filtration gave 133 mg of (3,5-diacetylphenyl)guanidine bis(amidinohydrazone) trihydrochloride (Compound 27) as a slightly off-white solid, mp 270–3° C.

Compound 28, FIG. 7F.28: A suspension of 3,5-diacetylaniline (0.531 g) in water (8 mL) was treated with cyanoguanidine (0.285 g) and conc. HCl (0.25 mL) and heated at reflux. After 6 hr the mixture was cooled and concentrated and 0.248 g of off-white solid was filtered out, mp 260–70 (dec). Of this, 0.238 g was heated at reflux with aminoguanidine hydrochloride (0.221 g) in 5.5 mL of aq. 91% methanol for 24 hr. Filtration gave 0.290 g of N-(3,5-diacetylphenyl)biguanide bis(amidinohydrazone) trihydrochloride (Compound 28) as fine white needles, mp 294–7° C.

Compound 31, FIG. 7G.31: 4-acetylphenyl isocyanate (1.2 g) and tris(2-aminoethyl)amine (0.300 mL) in methylene chloride (10 mL) were stirred at r.t. for 30 min. Filtration gave 1.35 g of tris(2-[([(4-acetylphenyl)amino]carbonyl)-amino]ethyl)amine, mp 189–90° C. This triketone (1.0 g) and aminoguanidine dihydrochloride (0.77 g) were heated in methanol (5 mL) for 4 hr. Addition of ethanol (5 ml) and filtration gave 1.08 g of tris(2-[([(4-acetylphenyl)-amino]carbonyl)amino]ethyl)amine tris(amidinohydrazone) trihydrochloride (Compound 31) as the dihydrate, mp 224–5° C. (dec.).

Compound 32, FIG. 7G.32: 3'-aminoacetophenone (0.446 g) and 1,3,5-benzenetricarbonyltrichloride (0.266 g) in tetrahydrofuran (5 mL) were stirred at r.t. for 30 min. Filtration gave 0.500 g of N,N',N"-tris(3-acetylphenyl)-1,3,5-benzenetricarboxamide, mp 270° C. The triketone (1.0 g) and aminoguanidine dihydrochloride (0.87 g) were heated in 2-methoxyethanol (5 mL) for 4 hr. Cooling and filtration gave 1.4 g of N,N',N"-tris(3-acetylphenyl)-1,3,5-benzenetricarboxamide tris(amidinohydrazone) trihydrochloride (Compound 32) solvated with one molecule of 2-methoxyethanol, mp 270–5° C. dec.

Compound 33, FIG. 7G.33, was prepared analogously from 4'-aminoacetophenone via the triketone N,N',N"-tris(4-acetylphenyl)-1,3,5-benzenetricarboxamide, mp 310° C., to give N,N',N"-tris(4-acetylphenyl)-1,3,5-benzenetricarboxamide tris(amidinohydrazone) trihydrochloride (Compound 33) solvated with three molecules of 2-methoxyethanol, mp 295–300° C. (dec) (slow heating).

Compound 34, FIG. 7H.34: 3,5-diacetylphenyl isocyanate (0.6 g) and tris(2-aminoethyl)amine (0.13 g) in methylene chloride (5 mL) were stirred at r.t. for 30 min. Filtration gave 0.6 g of tris(2-[([(3,5-diacetylphenyl)amino]carbonyl)-amino]ethyl)amine, mp 197–8° C. This hexa-ketone (0.47 g) and aminoguanidine dihydrochloride (0.61 g) were heated in methanol (5 mL) for 4 hr. Cooling and filtration gave 0.86 g of tris(2-[([(3,5-diacetylphenyl)amino]carbonyl)-amino]ethyl)amine hexakis(amidinohydrazone) heptahydrochloride (Compound 34) as the dihydrate hemi-ethanolate, mp 245–6° C. dec.

Compound 35, FIG. 7H.35: 4-acetylphenyl isocyanate (3 g) and tris(3-aminopropyl)amine (1.06 g) in tetrahydrofuran (50 mL) were stirred for 30 min. Ethanol (100 mL) was added and the mixture was left at r.t. for overnight. Filtration gave 2.8 g of tris(3-[([(4-acetylphenyl)amino]carbonyl)-amino]propyl)amine, mp 184-5° C. This diketone (0.4 g) and aminoguanidine dihydrochloride (0.29 g) were heated in methanol (3 mL) for 4 hours. Addition of ethanol (3 mL) and filtration gave 0.5 g of tris(3-[([(4-acetylphenyl)-amino]carbonyl)amino]propyl)amine tris(amidinohydrazone) trihydrochloride (Compound 35) as the dihydrate ethanolate, mp 209–10° C. dec.

Compound 36, FIG. 7H.36: 3,5-Diacetylphenyl isocyanate (0.4 g) and tris(3-aminopropyl)amine (0.12 g) in tetrahydrofuran (5 mL) were stirred at r.t. for 30 min. Filtration gave 0.32 g of tris(3-[([(3,5-diacetylphenyl)-amino]carbonyl)amino]propyl)amine, mp 147–8 C. This hexa-ketone (0.4 g) and aminoguanidine dihydrochloride (0.49 g) were heated in methanol (3 mL) for 4 hours. Addition of ethanol and filtration gave 0.58 g of tris(3-[([(3,5-diacetylphenyl)amino]carbonyl)amino]propyl)amine hexakis(amidinohydrazone) heptahydrochloride (Compound 36) as the dihydrate hemi-ethanolate, mp 250–1° C. (dec).

Compound 37, FIG. 7I.37: 3-Acetylphenyl isocyanate (1 g) and 4'-aminoacetophenone (0.84 g) in methylene chloride (5 mL) were stirred at r.t. for 30 min. Filtration gave 2.0 g of 3,4'-diacetyl-N,N'-diphenylurea, mp 252–3° C. (dec). This diketone (0.6 g) and aminoguanidine dihydrochloride (0.65 g) were heated in ethanol (5 mL). Cooling and filtration gave 0.8 g of 3,4'-diacetyl-N,N'-diphenylurea bis(amidinohydrazone) dihydrochloride (Compound 37) as the hemihydrate, mp 243–4° C. dec.

Compound 38, FIG. 7I.38: 3-Acetylphenyl isocyanate (0.27 g) and 3,5-diacetylaniline (0.3 g) were stirred in methylene chloride (5 mL) at r.t. for 30 min. Filtration gave 0.5 g of 3,3',5'-triacetyl-N,N'-diphenylurea, mp 223–4° C. This triketone (0.34 g) and aminoguanidine dihydrochloride (0.49 g) were heated in ethanol (5 mL) for 4 hr. Cooling and filtration gave 0.6 g of 3,3',5'-triacetyl-N,N'-diphenylurea tris(amidinohydrazone) trihydrochloride (Compound 38) as the hydrate, mp 245° C. dec.

Compound 39, FIG. 7I.39: N,N'-Bis(3,5-diacetylphenyl)-urea (0.38 g), aminoguanidine hydrochloride (0.44 g) and aminoguanidine dihydrochloride (59 mg) were heated at 90–100° C. in 2-methoxyethanol (5 mL) for 6 hours. Cooling and filtration gave 0.66 g of N,N'-bis(3,5-diacetylphenyl)urea tetrakis(amidinohydrazone) tetrahydrochloride (Compound 39) as the 2.5-hydrate hemi-methanolate, mp 263–4° C. dec.

Compound 40, FIG. 7I.40: N,N'-bis(3,5-diacetylphenyl)-nonanediamide (0.100 g), aminoguanidine hydrochloride (0.115 g), and aminoguanidine dihydrochloride (3 mg) were heated at reflux in 95% ethanol (2.5 mL) for 5 hr. Cooling and filtration gave 0.18 g of N,N'-bis(3,5-diacetylphenyl)- nonanediamide tetrakis(amidinohydrazone) tetrahydrochloride (Compound 40) as the dihydrate, mp 295–6° C.

Compound 41, FIG. 7J.41: N,N'-bis(3,5-diacetylphenyl) dodecanediamide (0.100 g), aminoguanidine hydrochloride (0.115 g), and aminoguanidine dihydrochloride (3 mg) were heated in 95% ethanol (2.5 mL) for hr. Cooling and filtration gave 0.070 g of N,N'-bis(3,5-diacetylphenyl) dodecanediamide tetrakis(amidinohydrazone) tetrahydrochloride (Compound 41) as the tetrahydrate, mp 268–9° C.

Compound 42, FIG. 7J.42: A suspension of 3,5-diacetylaniline (0.354 g) in methylene chloride (7 mL) containing 4-dimethylaminopyridine (5 mg) was treated with 2-methyl-1,5-pentanediyl diisocyanate (0.18 mL). After heating at reflux for 2 hr, the mixture was cooled. An aliquot was treated with t-butyl methyl ether to give seed crystals which were added to the reaction mixture. After stirring several hr, filtration gave 0.120 g of 1,5-bis[([(3,5-diacetylphenyl)-amino]carbonyl)amino]-2-methylpentane, mp 128° C. This tetraketone (0.100 g), aminoguanidine hydrochloride (0.115 g), and aminoguanidine dihydrochloride (3 mg) were heated in 95% ethanol (2.5 mL) for 18 hr. Cooling and filtration gave 0.16 g of 1,5-bis[([(3,5-diacetylphenyl)amino]carbonyl)amino]-2-methylpentane tetrakis(amidinohydrazone) tetrahydrochloride (Compound 42) as the tetrahydrate, mp 258–9° C.

Compound 43, FIG. 7J.43: N,N'-bis(3,5-diacetylphenyl) octanediamide (0.100 g), aminoguanidine hydrochloride (0.115 g), and aminoguanidine dihydrochloride (10 mg) were heated in 95% ethanol (2.5 mL) for 20 hr. Cooling and filtration gave 0.17 g of N,N'-bis(3,5-diacetylphenyl) octanediamide tetrakis(amidinohydrazone) tetrahydrochloride (Compound 43) as the 2.5-hydrate, mp 308–9° C.

7. EXAMPLE

Whole Cell Inhibition Assays for Urea and no Output

This section describes in detail the methods and the results of a tissue culture assay to determine the ability of the compounds of the invention to inhibit urea synthesis in activated macrophages.

7.1. Material and Methods

RAW 264.7 cells are plated in microculture wells at $1\times10^6$/ml in RPMI 1640 with 10% FBS and otherwise standard culture conditions and allowed to adhere for 5 hours. They are then activated with 25 U/ml γIFN and 0.1 gg/ml LPS in the presence of test inhibitors. The urea concentration present in the supernatant media, after 18 hours of culture, is determined by a colorimetric blood urea nitrogen diacetylmonoxime assay performed on an aliquot of the culture supernatant (Sigma Chem. Co., St. Louis, Mo.) and inhibition is expressed as the percentage urea compared to that of a parallel control culture treated identically except that the concentration of added inhibitor is zero.

The production of nitrite is determined by assay of the same tissue culture supernatant by means of a calorimetric assay. Briefly, 4 parts of test solution containing 1% (w/v) sulfanilamide, 0.1% naphthylethylenediamine di-HCl (Griess Reagent), 2.5% $H_3PO_4$ and one part media are mixed, incubated for 10 minutes and the absorbance at 560 nm determined. The nitrite concentrations are interpolated from reference curves prepared using $NaNO_2$.

Various concentrations of the test compounds are included in the media of the stimulated RAW 264.7 cells in culture. The concentration of urea and/or nitrite after 18 hours of activated culture is determined and compared to the uninhibited control value obtained from at least one parallel culture. The fractional reduction is calculated for each concentration of inhibitor and the $IC_{50}$ (concentration giving 50% reduction) is interpolated. Compounds were dissolved in media with mild heat (60° C.). Those with limited solubility were dissolved in base. The concentration of stock solutions of those compounds which were not completely soluble was determined by $OD_{280}$.

The culture supernatants are tested for the presence of an intracellular enzyme, lactate dehydrogenase (LDH) to determine the degree, if any, to which the test compound has caused cell death. In the examples reported hereinafter no such cellular toxicity due to the test compounds was observed.

7.2. Results

The results of the examination of guanylhydrazone compounds to measure their capacity to inhibit urea production are presented in Tables I, II and III. The most active compounds, reported in Table I, displayed $IC_{50}$ of less than 10 μM. The most active compound was an tetraguanylhydrazone decanediamide (Compound No. 14). Also highly active were the pentanediamide homolog of the above (Compound No. 13); the ethanedioxy bis(guanylhydrazone), (Compound No. 16); a mixed urea bis(guanylhydrazone) (Compound No. 9); and triacetylbenzine tris (guanylhydrazone) (Compound No. 1).

Compounds having either one or two phenyl nuclei were effective. When two nuclei were present their linkage by means of a urea, diamide or alkanedioxy functionality was effective. Test compounds having a single guanylhydrazone functionality were much less effective.

TABLE I

RESULTS OF IN VITRO ASSAYS FOR COMPOUNDS DEMONSTRATING HIGH LEVELS OF ACTIVITY

| Compound # | # Of Guanidino Groups | Dissolved in | dose evaluated (I.C.$_{50}$ In parenthesis) | -urea- % suppression of induced production | no$_2$/no$_3$ % suppression of induced production | arginine transport % suppression of induced peak |
|---|---|---|---|---|---|---|
| 1 | 3 | 5 mM solution in 5 mM NaOH; precipitation when diluted into RPMI | 25 μM 10 μM 1 μM (10 μM) | 100 60 | 72 58 | 40 20 0 |
| 9 | 3 | 5 mM solution in 5 mM NaOH; precipitation when diluted into RPMI | 25 μM 10 μM 1 μM (10 μM) | 100 60 0 | 71 53 0 | 68 32 14 |
| 13 | 4 | 5 mM solution in 5 mM NaOH; precipitation when | 500 μM 25 μM 50 μM 25 μM 10 μM (10 μM) | 100 100 87 77 45 | 52 43 | 93 19 7 |

TABLE I-continued

RESULTS OF IN VITRO ASSAYS FOR COMPOUNDS DEMONSTRATING HIGH LEVELS OF ACTIVITY

| Compound # | # Of Guanidino Groups | Dissolved in | dose evaluated (I.C.$_{50}$ In parenthesis) | -urea- % suppression of induced production | no$_2$/no$_3$ % suppression of induced production | arginine transport % suppression of induced peak |
|---|---|---|---|---|---|---|
| 14 | 4 | diluted into RPMI 5 mM solution in 5 mM NaOH, forms a kind of clot when cold, precipitation when diluted into RPMI | 200 µM<br>50 µM<br>10 µM<br>2 µM<br>(1 µM) | 100<br>100<br>78<br>68 | 100<br>100<br>69<br>0 | 100<br>86<br>19<br>9 |
| 15 | 2 | Not soluble; treat as #11, 12 | 150 µM<br>15.0 µM<br>5.0 µM<br>(10 µM) | 100<br>100<br>8 | 100<br>9<br>0 | 100<br>35<br>10 |
| 16 | 2 | Not soluble; treat as #11, 12, 15 | 250 µM<br>25 µM<br>5 µM<br>(1–10 µM) | 100<br>100<br>40 | 100<br>90<br>17 | 100<br>44<br>26 |

TABLE II

RESULTS OF IN VITRO ASSAYS FOR ACTIVE COMPOUNDS

| COMPOUND # | # OF GUANIDINO GROUPS | DISSOLVED IN | DOSE TESTED (I.C.$_{50}$ IN PARENTHESIS) | -UREA- % SUPRESSION OF INDUCED PRODUCTION | NO$_2$/NO$_3$ % SUPRESSION OF INDUCED PRODUCTION |
|---|---|---|---|---|---|
| 11 | 2 | Not soluble; dose defined by OD determination (280 mM) of SN of 5 mM NaOH -solution- +heat+ spin the suspension used as St. curve the ODs of #1, 9, 13 | 163 µM<br>16.3 µM<br>5.4 µM<br>(100 µM) | 100<br>0<br>0 | 100<br>0<br>0 |
| 12 | 2 | Not soluluble, dose defined by OD determination (at 280 mM) using as St. curve the ODs of #1, 9, 13 | 100 µM<br>(250 µM)? | 18–32 | 20 |
| 17 | 2 | Not soluble treated as #11, 12, 15, 16 | 177 µM<br>(150 µM) | 54–100 | 71–87 |
| 18 | 2 | Not soluble treated as #11, 12, 15, 16 and 17 | 233 µM<br>23.3<br>7.7<br>(25 µM) | 100<br>30<br>9 | 100<br>13<br>0 |
| 19 | 2 | Well dissolved in PBS | 1 mM<br>500 µM<br>250 µM<br>100 µM<br>50 µM<br>10 µM<br>(100 µM) | 100<br>100<br>100<br>50<br>30<br>0 | |
| 20 | 2 | 5 mM solution in 5 mN NaOH + heat | 400 µM<br>200 µM<br>50 µM<br>10 µM<br>(300 µM) | 100<br>38<br>19<br>16 | 84<br>15<br>0<br>0 |

TABLE III

RESULTS OF IN VITRO UREA PRODUCTION ASSAYS FOR COMPOUNDS DEMONSTRATING ACTIVITY

| COMPOUND # | # OF GUANIDINO GROUPS | DISSOLVED IN | DOSE TESTED (I.C.$_{50}$ IN PARENTHESIS) | -UREA- % SUPRESSION OF INDUCED PRODUCTION |
|---|---|---|---|---|
| 2 | 2 | Heat (60° C.- 2 hrs) 200 mM solution in RPMI | 200 µM<br>20 µM<br>(50 µM) | 100<br>0–17 |
| 3 | 2 | Heat (60° C.- 2 hrs) 1 mM solution in RPMI | 100 µM<br>50 µM<br>40 µM<br>1 µM<br>(500 µM) | 100<br>42<br>21<br>9 |
| 4 | 1 | Heat (60° C.- 2 hrs) 400 µM solution in RPMI | 400 µM<br>200 µM<br>100 µM<br>50 µM<br>20 µM<br>(300 µM) | 100<br>0<br>0<br>0<br>0 |
| 5 | 2 | Well dissolved in PBS; 5 mM solution | 1 mM<br>500 µM<br>250 µM<br>125 µM<br>60 µM<br>30 µM<br>(250 µM) | 73–100<br>64<br>52<br>48<br>37<br>24 |
| 6 | 1 | Heat (60° C.- 2 hrs) 1 mM solution in RPMI | 1 µM<br>100 µM<br>50 µM<br>(250 µM) | 100<br>40<br>0 |
| 7 | 1 | Heat (60° C.- 2 hrs) 10 mM solution in | 10 µM<br>2 µM<br>1 µM<br>100 µM | 100<br>55<br>40<br>35 |

TABLE III-continued

RESULTS OF IN VITRO UREA PRODUCTION ASSAYS FOR COMPOUNDS DEMONSTRATING ACTIVITY

| COMPOUND # | # OF GUANIDINO GROUPS | DISSOLVED IN | DOSE TESTED (I.C.$_{50}$ IN PARENTHESIS) | -UREA-% SUPRESSION OF INDUCED PRODUCTION |
|---|---|---|---|---|
| | | RPMI | 10 μM (2 mM) | 23 |
| 8 | 2 | Heat (60° C.- 2 hrs) 5 mM solution in RPMI | 500 μM 50 μM (50 μM) | 100 76 |
| 10 | 1 | Heat (60° C.- 2 hrs) 400 μM solution | 400 μM 200 μM 20 μM (No effect) | 0 0 0 |

8. EXAMPLE

Whole Cell Inhibition Assay for Arginine Uptake

This section describes in detail the methods and the results of a tissue culture assay to determine the ability of the compounds of the invention to inhibit the uptake of arginine by activated macrophages.

8.1. Materials and Methods

RAW 264.7 cells are plated in standard 96-well microculture plates at a concentration of $10^5$/well and allowed to adhere for from 2 hours to overnight. The medium is then replaced with medium containing the compound to be tested. One hour later, the medium is supplemented so as to contain 25 U/ml γIFN and 0.1 μg/ml LPS and the cultures incubated a further. The cells are then rinsed twice in HEPES-buffered Krebs salt solution with 0.1% glucose. Carrier-free tetra-$^3$H- arginine is added to each well (2.5 μCi/well with specific activity of 69 mCi/mmol) and the active uptake of arginine is allowed to continue for a 5 minute period after which the cells are rapidly cooled to 0° C. by lavage with iced saline containing 10 mM unlabeled arginine to displace any externally bound label. The contents of the washed cells are solubilized in 100 μl of formic acid and counted by standard techniques. The amount of tetra-$^3$H-arginine uptake as a function of time incubation time is shown in FIG. 6. In subsequent experiments to determine the acitivity of the inhibitors, incubations were performed for 8 hours.

8.2. Results

The compounds of the present invention which were most active in suppressing urea production in activated macrophages were tested to determine their effects on the uptake of arginine. The results, shown in Table I of Section 7.2, indicate that each of the active compounds were effective inhibitors of uptake at a dose similar to that which effectively inhibited urea production. These data suggest that an arginine transport protein is a target of action of these compounds.

9. EXAMPLE

Arginase Inhibition Assay

This section describes in detail the methods and the results of a cell-free assay to determine the ability of the compounds of the invention to inhibit the activity of argininase obtained from macrophages.

9.1. Materials and Methods

A 1200 g×2 minutes supernatant is obtained from a cell lysate of washed RAW 264.7 cells made by the addition of a lysis buffer containing 50 mM Hepes, 1% NP-40, 0.1 mg/ml phenylmethylsulfonylfluoride (PMSF), and aprotinin at 1 μg/ml. The volume of supernatant is adjusted so that the protein concentration is between 2 and 4 mg/ml. A 1:4 mixture of the supernatant in activation buffer (30 mM $MnCl_2$, 0.3 M glycine, 1 BSA, pH 9.8) containing various concentrations of the test inhibitor is incubated at 55° C. for 20 minutes. Arginase activity is determined by mixing a 1:2 the above solution and 0.375 M arginine, pH 9.8 for 10 minutes at 37° C. The urea concentration after this incubation is determined as above.

9.2. Results

The six compounds most active in the suppression of cellular urea production were tested to determine whether any could inhibit the activity of arginase in the above-described cell lysate assay. The results do not indicate arginase to be sensitive to inhibition by the compounds of the present invention at the concentrations and under the conditions employed.

10. EXAMPLE

Treatment of Cachexia in Vivo

An animal model of tumor-associated protein catabolic illness (cachexia) was employed to directly test the efficacy of Compound No. 14 in reducing whole-body nitrogen losses. Tumors were induced in the appropriate groups by intramuscular inoculation with $15 \times 10^6$ AtT-20 cells; this model is known to cause a protein catabolic illness characterized by the consumption of normal quantities of food, but 20% net whole-body losses of protein within 14 days. Compound No. 14 was administered to the "treated" groups in a daily dose of 0.4 mg/Kg, intraperitoneal. Nude mice (nu/nu) were housed in metabolic cages (4 per cage) to facilitate collection of daily urine samples for 14 days. Food intake was measured daily. There were four groups of animals: 1) untreated, non-tumor bearing controls; 2) untreated, tumor-bearing; 3) treated, tumor-bearing, and 4) treated, non-tumor-bearing. Urine was collected and urinary urea losses quantified.

The results are summarized in Table IV (expressed as mg urea/group):

TABLE IV

IN VIVO ACTIVITY OF COMPOUND #14 IN SUPPRESSING WHOLE-BODY NITROGEN LOSS
URINARY UREA LOSS (mg/group)

| Day After Tumor | Controls | Tumor, Untreated | Tumor, Treated | Controls, Treated |
|---|---|---|---|---|
| 2 | 189 | 240 | 195 | 193 |
| 4 | 252 | 342 | 368 | 285 |
| 6 | 256 | 508 | 295 | 397 |
| 7 | 302 | 456 | 312 | 247 |
| 8 | 287 | 300 | 275 | 257 |
| 10 | 177 | 259 | 206 | 216 |
| 11 | 240 | 279 | 219 | 239 |
| 12 | 230 | 230 | 115 | 203 |

TABLE IV-continued

IN VIVO ACTIVITY OF COMPOUND #14 IN SUPPRESSING
WHOLE-BODY NITROGEN LOSS
URINARY UREA LOSS (mg/group)

| Day After Tumor | Controls | Tumor, Untreated | Tumor, Treated | Controls, Treated |
|---|---|---|---|---|
| 13 | 192 | 186 | 201 | 242 |
| 14 | 161 | 238 | 187 | 157 |
| Sum totals | 2286 | 3038 | 2373 | 2436 |

The groups consumed similar quantities of food (16±2 g/day) during this experiment.

The data demonstrate that Compound No. 14 prevented excess urinary urea excretion normally associated with cachexia.

Since urea loss represents 80% of whole-body nitrogen losses, and the nitrogen intakes were similar in all groups, these data further suggest that Compound No. 14 augments whole-body nitrogen retention.

The significance of these observations is demonstrated by estimating the impact of these nitrogen losses to muscle mass. Compound No. 14 prevented the loss of approximately 200 mg urea/mouse over the 14 day period. This is equivalent to approximately 100 mg of nitrogen, 625 mg of protein, or 2.7 g of wet muscle mass that is retained by treatment with Compound No. 14.

11. EXAMPLE

Treatment of Inflammation in Vivo

A standard animal model of inflammation was utilized to directly test the efficacy of Compound No. 14 as an anti-inflammatory. Paw swelling induced by injection of the irritant carrageenan into murine foot pads has been used to detect clinically useful anti-inflammatory drugs since the early 1960's.

Paw edema was induced by injection of 50 microliters of 1% Lambda-carrageenan in HEPES 25 mM, pH 7.4, into the planter surface of the left hindpaw of C3H/HeN mice, the right paw was injected with 50 microliters of HEPES alone. The animals were divided into two groups: controls (n=3) received vehicle only, i.p. 1.5 hour before paw injection; the experimental group (n=4) was treated with Compound No. 14, 5 mg/Kg, i.p. 1.5 hour before paw injection. Three hours after paw injection, paw thickness was measured using a caliper, and the data expressed as change of carrageenan paw vs HEPES paw thickness.

The results are summarized in Table V which contains the carrageenan-induced increase in paw thickness in mm of three control and three Compound No. 14 treated mice. The inhibition can also be reported as percent inhibition of swelling as defined by the standard formula: Percent inhibition=(1-(treated/control))×100. Calculation of this parameter for treated animals in which Compound No. 14 suppressed swelling yields a 70W inhibition.

TABLE V

EFFECT OF COMPOUND NO. 14 ON INFLAMMATION
CHANGE IN PAW THICKNESS

| Untreated Controls | Treated With Compound #14 |
|---|---|
| 1.47 | 0.54 |
| 1.50 | 0.41 |
| 1.24 | 0.4 |

FIG. 8 presents the effects of various doses of Compound No. 14 in the same assay. The data show that doses of between about 1 and 10 mg/Kg of body weight are effective at inhibiting paw swelling.

These data demonstrate that Compound No. 14 prevented inflammation, which is believed to be mediated by the inhibition of arginine-transport dependent nitric oxide production in inflammatory cells.

12. EXAMPLE

Compound No. 14 has no Effects on Endothelial Derived Relaxing Factor Mediated Vasodilatory Responses An important requirement of drug used to control the vascular collapse and hypostension caused by macrophage NO production is that it not interfere with the activity of EDRF in vivo. Such interference can cause an uncontrolled hypertension and has prevented the effective clinical use of NO-synthase inhibitors. We measured the effect of Compound No. 14 on EDRF activity in an animal model and found that compound 14 inhibits NO production yet does not inhibit EDRF activity.

Female Sprague-Dawley rats (225–250 g body weight) were anesthetized with nembutal (50 mg/Kg, i.p.), a tracheostomy tube was inserted, and the carotid artery and jugular vein cannulated by standard methods using polyethylene tubing (PE 50). Tracey, K. J., et al., 1986, Science 234, 470–474. Blood pressure was recorded continuously with a pressure transducer and recorder (Model RS-3200, Gould Inc.,). In the experiment shown here, animals received a single sterile intra-arterial dose of either NG-methyl-L-arginine (NMA; Sigma; 10 mg/Kg), Compound No. 14 (50 mg/Kg), or vehicle (0.4 ml). Acetylcholine (ACh) diluted in LPS-free sterile water was administered via the jugular vein cannula at the doses indicated. The solutions were diluted to produce a constant injectable volume of 1 ml/Kg body weight.

The hypotensive (EDRF) response was measured as the decline in mean arterial blood pressure recorded 30 sec after administration of ACh. The number of animals studied at each dose of acetylcholine was 4–6 for each experimental condition; data are expressed as the mean±s.e.m.

EDRF activity was inhibited by NMA, evidenced by attenuated blood pressure responses as compared to vehicle-treated controls (FIG. 9; see also, Kilbourn, R. G., et al., 1990, Proc Natl. Acad Sci. 87, 3629–3632). In contrast, Compound No. 14 did not suppress acetylcholine-induced EDRF activity in vivo, indicating that Compound No. 14-treated animals retained the functional capacity for endothelial-derived NO activity.

13. EXAMPLE

Compound No. 14 Prevents Fatal Endotoxic Shock

Experiments were undertaken to evaluate the effects of Compound No. 14 in preventing the lethal toxicity of lipopolysaccharide (LPS). LPS was administered to induce 50% lethality within 72 hr in BALB/c mice (FIG. 10). BALB/c mice (19–21 g) were given LPS (*E. coli* 0111: B4; Sigma) in a dose of 13.75 mg/Kg by intraperitoneal injection (0.2 ml/mouse). Stock LPS solutions (10 mg/ml) were sonicated initially for 20 min, diluted in LPS-free water (1.375 mg/ml), then sonicated again for 10 min immediately prior to injection. Compound No. 14 (1 mg/Kg, i.p.) was administered 1.5 hr before LPS. Compound No. 14 injectate was free of LPS as measured by quantitative chromogenic Limulus amebocyte lysate test (BioWhittaker, Walkersville, Md.). Data points are from two groups consisting of 10 mice per group.

Compound No. 14 administered 1.5 hours before LPS reduced lethality. Data were subjected to statistical analysis using the z test for independent proportions. The difference bewteen control and Compound No. 14 is significant (one-tailed p value <0.05; z=1.95).

There were no gross signs of systemic toxicity in animals receiving Compound No. 14 alone. After LPS, controls were ill-kempt, had decreased mobility, and huddled together. These visible signs of LPS toxicity were markedly suppressed by Compound No. 14. Diarrhea occurred in all animals, and was not suppressed by Compound No. 14.

Previously available NOS inhibitors have had limited success in improving survival from endotoxemia, in part because they indiscriminately suppress EDRF. Cobb, J. P., 1992, J. Exp. Med. 176:1175–1182; Minnard, E. A., 1994, Arch Surg. 129:142–148; Billiar, T. R., 1990, J. Leukocyte. Biol. 48:565–569. Suppression of EDRF during endotoxemia may impair survival by causing vasoconstriction and a diminution of blood flow to critical vascular beds. The present data now indicate that inhibiting cytokine-inducible macrophage NO with an agent that preserves endothelial-derived NO responses can confer a survival advantage during septic shock.

14. EXAMPLE

Compound No. 14 Prevents the Production of Cytokines and no

This section describes in detail the methods and the results of a tissue culture assay to determine the ability of the compounds of the invention to inhibit the production of TNF by activated macrophages, and shows, for purposes of explanation and not limitation, that Compound No. 14 is effective in blocking the secretion of TNF by a mechanism that is independent of the inhibition of arginine uptake.

RAW 264.7 cells were plated in standard 6-well culture plates at a density of $10^6$/well and allowed to adhere for from 2 hr to overnight. The medium was then replaced with medium containing the compound to be tested. One hour later, the medium was supplemented so as to contain 25 U/ml γIFN and 0.1 μg/ml LPS and the cultures incubated a further 18 hr. The medium was then collected, and cell debris removed by centrifugation. This conditioned supernatant was then assayed for the presence of TNF using standard methodologies: L929 cell cytotoxicity bioassay, radioimmunoassay or ELISA, and Western blotting with antibodies against murine TNF.

FIG. 11 shows that in the presence of increasing amounts of Compound No. 14, the production of bioactive TNF as determined by L929 cell bioassay by RAW 264.7 cells was prevented. The data show that at 10 μM Compound No. 14 there was a reduction of more than 99% of the TNF accumulation in the culture medium. FIG. 12 shows a Western blot that demonstrates the absence of TNF protein in the medium of cells cultured with 5 and 25 μM concentrations of Compound No. 14. The failure of Compound No. 14-treated cells to secrete TNF can not be simply attributed to the inhibition of NO synthesis by Compound No. 14. The NOS inhibitor N-methyl-arginine (NMA), even at concentrations of 10 μM, did not inhibit the production of TNF in this system. The inhibition of TNF production was also not attributable to the effects of arginine depletion brought on by the blockage of arginine transport. FIG. 13A shows that Compound No. 14, at a 5 μM concentration, functioned as an inhibitor of NO synthesis, but that this inhibition could be partially overcome by the presence of between about 50 and 100 μM arginine in the medium. By contrast the data in FIG. 13B clearly show that the effects on TNF secretion of Compound No. 14 at 5 μM were not reduced even by as much as 1.0 mM extracellular arginine. These results show that Compound No. 14 specifically blocked the production of TNF from activated macrophages by a mechanism that does not critically depend on arginine.

Qualitatively similar data has been obtained by measurement of the serum TNF levels in rats stimulated to produce TNF by parenteral LPS administration. Rats were given Compound No. 14, i.p., 2.0 hours prior to LPS stimulation. The serum levels of TNF were measured at between 2 and 3 hours after LPS stimulation. Compound No. 14-treated animals showed only about half the level of serum TNF as found in the untreated controls.

Similar results concerning a variety of cytokines in addition to TNF, e.g., IL-6 and Macrophage Inflammatory Proteins-1α and -1β (MIP-1α and MIP-1β) were obtained using human peripheral blood as a source of monocytes. Human peripheral blood mononuclear cells (PBMC) were isolated using "FICOLLO®"-based methods and plated in standard 6-well culture plates at a concentration of $10^6$/well and allowed to adhere for from 2 hr to overnight whereupon non-adherent cells were washed out and the medium was then replaced with medium containing the compound to be tested. One hour later, the medium was supplemented so as to contain 25 U/ml γIFN and 0.1 μg/ml LPS and the cultures incubated a further 18 hr. The medium was then collected, and cell debris removed by centrifugation. This conditioned supernatant was then assayed for the presence of cytokines using the standard methodologies of L929 cell cytotoxicity bioassay and immunoassay (ELISA). The results indicated that, when tested in this system, Compound No. 14 effectively inhibited the production of TNF, IL-6, MIP-1α, and MIP-1β by human PBMC cells at a concentration of about 10–20 μM. FIGS. 14A–D show that in the presence of increasing amounts of Compound No. 14 from 1 to 20 μM, the production of these cytokines by human PBMC cell cultures was prevented.

15. EXAMPLE

Compound No. 14 Confers Protection from Focal Cerebral Infarction

This section describes in detail the methods and the results of an animal model to determine the ability of Compound No. 14 to treat cerebral infarction (also known as brain infarction or "stroke").

Lewis rats (male, 270–300 g) were given food and water ad libitum before and after surgery. Animals were anesthetized with ketamine (120 mg/Kg i.m.), allowed to breathe spontaneously, and body temperature maintained at 35.5–36.5° C. with a heating blanket. The ventral neck and area between the right eye and ear was shaved. A midline ventral cervical incision was used to expose the left common carotid artery (CCA) which was dissected free from surrounding tissue with preservation of the vagus nerve. A loop of 4-0 silk was then placed around the artery for future manipulation. The right common carotid artery was then exposed and permanently occluded with double 4-0 silk ligatures.

To perform the craniotomy, a 1 cm incision was made orthogonal to the line joining the external auditory canal and the lateral canthus of the right eye. With the aid of a dissecting microscope, the right middle cerebral artery was exposed through a 1 mm burr hole drilled approximately 2 cm rostral to the fusion of the zygoma with the temporal bone. Drilling was performed under a continuous drip of normal saline to avoid transmission of heat to the underlying cortex. The bone was thinned with the drill, leaving a thin shell which was removed with a micro-hook and microforceps. The dura mater was then cut and reflected with a 30 gauge needle, exposing the right middle cerebral artery (MCA) approximately 1 mm from the rhinal fissure.

Using a micromanipulator and a 20 micron tungsten wire hook, the right middle cerebral artery was elevated 0.5 mm above the cortical surface and divided by application of an electrocautery tip to the tungsten hook above the vessel. The application of heat quickly cauterized and severed the artery which fell back onto the cortex with no underlying cortical injury. To cause a reproducible stroke the left CCA must be temporarily occluded for 30–60 minutes. Accordingly, in the present model the left CCA was occluded for 30 minutes. Surgical gelfoam was placed over the craniotomy defect, and the skin incisions closed with a vicryl sutures. The animals were then returned to their cages, where they were allowed free access to food and water for 24 hours. After surgery, animals were somewhat clumsy but resumed activities including walking, eating, and drinking.

Twenty-four hours after MCA severing, animals were anesthetized and decapitated and the brains were quickly removed without perfusion and coronally sectioned at 1 mm intervals with a brain slicer for analysis. Freshly prepared slices were immersed and incubated in 2,3,5-triphenyltetrazolium (TTC) (2% in NaCl, 154 mM) for 30 minutes at 37° C. in the dark to stain for mitochondrial dehydrogenase activity. Brain infarctions were visualized as areas of unstained (white) tissue which were easily contrasted with viable tissue which stained red. Slices were then placed in buffered 10% formalin and infarct area determined by planimetry on projected images of photographed brain slices. Infarct size for an individual animal was calculated by summing the infarct area present on each brain slice and dividing by the sum of hemisphere area for all slices for that animal (expressed as a percentage of hemisphere area for each slice). Animals were studied in groups of 10, and the data expressed as average stroke volume for the group.

The mean infarct size of controls (not treated with Compound No. 14) was observed to be 3.1%±0.5%. Animals that received Compound No. 14 (1 mg/Kg, i.v.) one hour before the artery was severed developed smaller stroke size (1.7%+ 0.2%). These differences were statistically significant ($p<0.05$) by Student's t-test for unpaired data. These experiments indicated that Compound No. 14 effectively reduced the size of focal cerebral infarction.

16. EXAMPLE

Anti-Neoplastic Activity of Compound No. 14

This section describes in detail the methods and results of an animal model of tumor growth to determine the ability of the compounds of the invention to inhibit tumor growth, and cause regression of tumors. Cells are plated in standard tissue culture flasks in DMEM supplemented with fetal calf serum (10%). Chinese hamster ovary (CHO) cells stably transfected with a mammalian expression vector constitutively secrete human TNF (CHO-TNF). The experiments with the CHO-TNF tumor were performed as follows: on the day of injection into nude mice, cells are harvested and injected intramuscularly ($10-15 \times 10^6$ cells per animal) into the hindlimb of nu/nu nude mice (20 g body weight). Animals are housed and provided food and water ad libitum. Tumor growth is monitored, and when established tumors are present (during week six) the test compounds are administered daily (0.4 mg/Kg intraperitoneal, once daily). After two weeks the animals are euthanized, the tumor weighed, and measured with a caliper. The CHO-TNF tumor also metastasizes to the skin of these animals; the number of metastases is scored.

Parenteral administration of Compound No. 14 caused a reduction in tumor size in four out of five animals. The tumors of these animals were weighed and their size determined. Examination of the mice for skin metastases revealed that an average of 2.5±1 skin metastases developed in 4 out of 5 controls; skin metastases were not present in any of the treated animals. These data show that Compound No. 14 has anti-tumor activity.

|  | TUMOR WEIGHT (g) | TUMOR DIMENSION (mm²) | # of METASTASES |
|---|---|---|---|
| CONTROL (n = 5) | 2.686 ± 0.77 | 343.58 ± 64.1 | 2.5 ± 1.1 |
| No. 14 (n = 4) | 1.628 ± 1.07 | 207.99 ± 119.90 | 0 |

17. INHIBITORY EFFECTS OF COMPOUND NO. 14 ON ARGININE UPTAKE AND NO OUTPUT OF PREVIOUSLY QUIESCENT VERSUS ACTIVATED CELLS

This section describes experiments that measure the concentration of Compound No. 14 needed to inhibit arginine uptake and NO output. The techniques employed were described in section 7.1 supra.

FIG. 13A shows the effects of Compound No. 14 on the output of NO by RAW 264.7 cells that have been continuously exposed to Compound No. 14 from one hour prior to γ-IFN/LPS stimulation until completion of the assay 18 hours after stimulation. The data show that Compound No. 14 was a inhibitor of NO output that was competitively antagonized by extracellular arginine. These data indicate that the $I.C._{50}$ for Compound No. 14 in this assay, at physiologic arginine concentrations (100 $\mu$M), was between 3 and 5 $\mu$M.

As shown in FIG. 6, the peak level of arginine uptake by RAW 264.7 cells occured at about 8 hours after γ-IFN/LPS stimulation. When RAW 264.7 cells were exposed to Compound No. 14 prior to stimulation, as in FIG. 13B, and the level of arginine uptake measured at 8 hours, the $I.C._{50}$ for arginine uptake of Compound No. 14 was very similar that observed for NO output, 7.5 $\mu$M (data not shown).

All effects of Compound No. 14 on macrophage NO output, however, could not be entirely attributed to an acute blockade of arginine transport. FIG. 15 shows the results observed when RAW 264.7 cells were γ-IFN/LPS-stimulated in the absence of any inhibitor and, 8 hours thereafter, the cells were exposed for 10 minutes to Compound No. 14, whereupon arginine uptake was measured. An I.C.$_{50}$=60±15 μM (mean±std. err., n=3) was measured when RAW 264.7 cells, that had been γ-IFN/LPS-stimulated 8 hours previously were exposed to Compound No. 14 in arginine-free buffer for 10 minutes prior to assay of arginine uptake. The results of these acute exposure experiments differed from the previously discussed, continuous exposure results in two ways. Firstly, approximately one third of the total arginine uptake occured through a Compound No. 14-independent mechanism which appeared to be present in unstimulated as well as stimulated RAW 264.7 cells. Secondly, the concentration of Compound No. 14 needed to 50% inhibit arginine uptake after γ-IFN/LPS-induced arginine transport has been established for a period of hours was greater than that needed to prevent 50% of the increased arginine uptake or NO output when Compound No. 14 was introduced prior to stimulation.

An intermediate level of sensitivity to Compound No. 14 was observed when γ-IFN/LPS-stimulated RAW 264.7 cells were exposed to inhibitor from 8 hours after the initial stimulation until the end of the experiment. In these experiments, NO output was measured during hours 12–24.

FIG. 16 demonstrates that under such experimental conditions an I.C.$_{50}$ of 20±2 μM (mean±std. err., n=3) was observed.

Together these data show that when RAW 264.7 cells were exposed to Compound No. 14 prior to activation by γ-IFN/LPS, NO output and inducible arginine uptake were equally sensitive to low levels of Compound No. 14, while the arginine uptake of unstimulated RAW 264.7 was insensitive to Compound No. 14. By contrast, the arginine uptake of RAW 264.7 cells, stimulated with γ-IFN/LPS, and exposed briefly to Compound No. 14 after a delay was less sensitive to of Compound No. 14 than when Compound No. 14 was given prior to stimulation. Likewise the NO output of cells treated with Compound No. 14 hours after stimulation was shown to be less sensitive to inhibition by Compound No. 14 than was the induction of NO production by previously quiescent cells.

These data indicate that higher levels of Compound No. 14 will be required, in vivo, to block the ongoing production of NO by activated macrophages than would be needed to prevent the initiation of NO production by non-activated macrophages and that Compound No. 14 will be more effective when chronically applied than when acutely applied to cells.

18. HIGH-PERFORMANCE LIQUID CHROMATOGRAPHY METHOID AND DETERMINATION OF PHARMACOKINETIC CONSTANTS THEREBY

A high-performance liquid chromatographic (HPLC) method has been developed for a series of aromatic guanylhydrazones that have demonstrated therapeutic potential as anti-inflammatory agents. The compounds were separated using octadecyl or diisopropyl-octyl reverse-phase columns, with an acetonitrile gradient in water containing heptane sulfonate, tetramethylammonium chloride, and phosphoric acid. The method was used to reliably quantify levels of analyte as low as 78.5 ng per injection, and the detector response was linear to at least 5000 ng per injection. The compounds could be extracted and concentrated from biological samples using octadecyl-silane solid-phase extraction columns. The assay system was used to determine the basic pharmacokinetics of a lead compound, Compound No. 14, from plasma concentrations following a single intravenous injection in rats.

18.1. Experimental Materials and Methods

Chemicals

Heptane sulfonate (HS), tetramethylammonium chloride (TMAC), and phosphoric acid were obtained from Aldrich (Milwaukee, Wis., USA), and pentamidine isethionate from May and Baker (now Rhone-Poulenc; Dagenham, UK). HPLC-grade acetonitrile was acquired from Fisher (Fairlawn, N.J., USA) and all water was filtered and deionised by a Picopure system (Hydro Service and Supplies; Research Triangle Park, N.C., USA). All guanylhydrazones were synthesized as described (Ulrich, P. & Cerami, A., 1984, J.Med.Chem. 27:35; Ulrich, P. et al., 1982, Drug Dev.Res. 2:219) and the purity confirmed by -elemental analysis, proton NMR, and melting point.

Chromatographic Conditions

A Hewlett-Packard model 1090 liquid chromatograph (Wilmington, Del., USA) equipped with an autosampler, photodiode array detector, and Chemstation operating software was used for all analyses. The columns used were either a Supelcosil LC-18 250×4.6 mm octadecylsilane column with 5 mm particle size (Supelco; Bellefonte, Pa., USA) or a Zorbax RX-C8 250×4.6 mm column with 5 mm particle size (Mac Mod Analyticals; Chadds Ford, Pa., USA) kept at room temperature. Buffer A was 10 mM HS/10 mM TMAC/4.2 mM $H_3PO_4/H_2O$ and buffer B 10 mM HS/10 mM TMAC/4.2 mM $H_3PO_4$/75% $CH_3CN$/25% $H_2O$. Using a flow rate of 1.5 ml/min, runs were initiated at 10%B and a linear gradient to 90%B was performed over 30 min. The column was then returned to 10%B over 7 min, followed by 3 min re-equilibration. The compounds were detected by absorbance at 265 nm, with 540 nm used as a reference wavelength.

Sample Preparation

The test compounds and the internal standard, pentamidine, were dissolved in distilled water to make 1 mg/ml stock solutions. To determine the relative retention times and peak shapes, a single test compound and the internal standard were diluted to 10 μg/ml in distilled water, and 100 μl injected onto the HPLC.

To extract the compounds, an equal volume of HPLC buffer A was added to the test sample (to which pentamidine had been added to 5 μg/ml) before being loaded onto conditioned Supelclean C-18 solid-phase extraction cartridges. The cartridges were then washed with 1.0 ml of distilled water and eluted with 1.0 ml of 10 mM HS/10 mM TMAC/4.2 mM $H_3PO_4$/95% $CH_3CN$/5% $H_2O$. In some experiments, 100 μl of this eluate was injected onto the HPLC, and, in others, the elution buffer was removed in vacuo and the pellet resuspended in HPLC buffer A before injection of 100 μl. Standard addition curves were constructed in distilled water, human urine, and mouse plasma by the addition of various amounts of test compound and 5 μg/ml pentamidine. These samples were either injected -directly or subjected to the solid-phase extraction system previously mentioned.

Pharmacokinetic Studies

Male Sprague-Dawley rats (Harlan Sprague Dawley, Indianapolis, Ind., USA) were anesthetized with ketamine and the right carotid artery cannulated with polyethylene tubing (PE-50). The animals were given 10 mg/kg of Compound No. 14 in a single intra-arterial injection of 380 μl. At 0, 5, 15, 30, 60, 90, 120, 180, 240, 300, 360 minutes 400 μl of blood was removed, stored at 4° C. for 4 hr, and then centrifuged at 15,000×g for 10 min, and the serum layer collected. Sodium azide was added to 0.01 v/v to prevent microbial growth and pentamidine was added to 5 μg/ml. Twenty-five Al of the resulting sample was analyzed by the HPLC method described.

18.2. Results

In designing a separation system for the aromatic guanylhydrazones, ion-pair buffers were chosen which contained 10 mM heptane sulfonate, 10 mM tetramethylammonium chloride, and 4.2 mM phosphoric acid, as these buffers had been used successfully to separate aromatic diamidines, B. J. Berger, et al., 1991, J. PHARMACOL. EXPER. THER. 256:883, which bear some structural similarity to the present compounds. Use of these buffers with a reverse-phase C-18 column was found to be ideal for the elution of Compound No. 14. Elimination of either of the ion-pair reagents from the buffer led to a complete retention of Compound No. 14 by the HPLC column (data not shown). Separation of Compound No. 14 and the internal standard, pentamidine, was performed with a Zorbax RX-C8 column.

While Compound No. 14 and pentamidine could easily be detected in raw serum samples, an extraction system was developed to allow for concentration of the analytes from samples containing trace amounts and also to minimise the amount of protein injected on the column. Using reverse-phase, solid-phase extraction columns (SPEC) and an elution buffer consisting of 10 mM TMAC/10 mM HS/4.2 mM $H_3PO_4$/95% $CH_3CN$, the recovery of Compound No. 14 and pentamidine was found to be 75.60% 13.77% and 92.27±6.52% respectively from C-18 SPEC (n=6). This recovery was superior to that found for the compounds on C-8, cyanopropyl, or phenyl SPEC (data not shown). In addition, to optimize recovery, it was found beneficial to add an equal volume of HPLC A buffer to the sample before loading onto the SPEC. This step led to a 20-fold increase in recovery from C-18 SPEC.

Further studies with Compound No. 14 and the solid-phase extraction system demonstrated that the limit of detection was 78.5 ng per injection, and that the compound could be efficiently extracted from urine and plasma samples (data not shown). The assay was found to be linear from the limit of detection up to at least 5000 ng per injection, and gave the following regression for a plot of Compound No. 14 peak area vs. amount injected: y=267.507x−45.251 ($r^2$=0.99). The method was also found to be accurate, with an intraday variation of 1.5% on samples of 1000 ng Compound No. 14 injected (n=4), and an interday variation of 9.5% on samples of 625 ng injected (n=3).

The HPLC method was applied towards estimating the pharmacokinetic parameters of Compound No. 14 in adult rats receiving a 10 mg/kg dose as a single intra-arterial injection. In these experiments, the solid-phase extraction step was omitted due to the small volume of each sample, and the relatively large amount of Compound No. 14 which was recovered. Typical serum decay curves were obtained (FIG. 17, solid line), and the method of residuals, Gibaldi, M., & Perrier, D., 1982, PHARMACOKINETICS (Marcel Dekker, New York) pp. 433–444, was used to calculate the pharmacokinetic parameters (FIG. 17, dashed lines). The distribution rate constant (α) was found to be 0.31±0.09 $min^{-1}$, the elimination rate constant (β) 0.0023±0.0000 $min^{-1}$, the initial distribution concentration (A) 63.01±43.78 mg/ml, the initial elimination concentration (B) 1.57±0.14 mg/ml, the distribution half-life ($t_{1/2}α$) 2.41±0.69 min, the elimination half-life ($t_{1/2}β$) 5.02±0.00 hr, the volume of -distribution ($V_d$) 2.45±0.21 L, and the total clearance ($C_L$) 5.62±0.47 ml/min (n=3 for all). These values show that the compound persists in the serum for some time after a single i.a. injection. Experiments performed via intraperitoneal or oral dosing routes indicate that the drug is not rapidly absorbed, and may have a low bioavailability (data not shown). The choice of a 10 mg/kg dose is applicable, as the compound was found to have an $LD_{50}$ of 50 mg/kg when given intraperitoneally and one that exceeds 1 g/kg when given orally.

The present invention is not to be limited in scope by the specific embodiments described which were intended as single illustrations of individual aspects of the invention, and functionally equivalent methods and components were within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for ameliorating cachexia in a subject in need of such amelioration which comprises administering a therapeutically effective amount of a compound or a pharmaceutically acceptable salts thereof, said compound having either one of the formula:

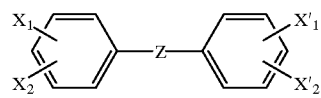

wherein:

$X_2$ is GhyCH—, GhyCCH$_3$— or H—;

$X_1$, X$_1$, and $X'_2$, independently are GhyCH— or GhyCCH$_3$—;

Z is —NH(CO)NH—, or —A—(CH$_2$)$_n$—A—, n is 2–10, which is unsubstituted, mono— or di-C-methyl substituted, or a mono— or di-unsaturated derivative thereof, and A is, independently, —(CO)NH—, —NH(CO)—, —NH(CO)NH—, —NH— or —O—; or

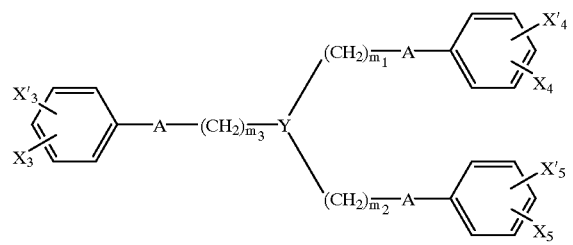

wherein:

$X_3$, $X_4$ and $X_5$, independently are GhyCH— or GhyCCH$_3$—;

$X'_3$, $X'_4$ and $X'_5$, independently are H, GhyCH— or GhyCCH$_3$—;

Y is (C$_6$H$_3$), when m$_1$, m$_2$, m$_3$ are 0, or Y is N, when, independently, m$_1$, m$_2$, m$_3$ are 2–6; and A is, independently, —(CO)NH—, —NH(CO)—, —NH(CO)NH—, —NH— or —O—.

2. The method of claim 1 wherein the compound is N,N'-bis(3,5 -diacetylphenyl)decanediamide tetrakis (amidinohydrazone) tetrahydrochloride.

3. The method of claim 1 wherein the compound is N-(4-acetylphenyl)-N'-(3,5-diacetylphenyl)urea tris (amidinohydrazone) trihydrochloride.

* * * * *

UNITED STATES PATENT AND TRADEMARK OFFICE
CERTIFICATE OF CORRECTION

PATENT NO.     : 6,248,787 B1
DATED          : June 19, 2001
INVENTOR(S)    : Marina Bianchi et al.

It is certified that error appears in the above-identified patent and that said Letters Patent is hereby corrected as shown below:

Drawings,
Drawing sheet FIG.7H should be replaced with attached drawings sheet FIG. 7H.

Signed and Sealed this

Third Day of December, 2002

JAMES E. ROGAN
*Director of the United States Patent and Trademark Office*